United States Patent
Jackson et al.

(10) Patent No.: US 10,568,794 B2
(45) Date of Patent: Feb. 25, 2020

(54) SURGICAL TABLE WITH PATIENT SUPPORT HAVING FLEXIBLE INNER FRAME SUPPORTED ON RIGID OUTER FRAME

(71) Applicant: WARSAW ORTHOPEDIC, INC., Warsaw, IN (US)

(72) Inventors: Roger P. Jackson, Prairie Village, KS (US); Lawrence E. Guerra, Mission, KS (US); Trevor A. Waggoner, Kansas City, KS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 332 days.

(21) Appl. No.: 15/483,063

(22) Filed: Apr. 10, 2017

(65) Prior Publication Data
US 2017/0209325 A1 Jul. 27, 2017

Related U.S. Application Data

(62) Division of application No. 14/793,050, filed on Jul. 7, 2015, now Pat. No. 9,629,766.
(Continued)

(51) Int. Cl.
*A61G 13/04* (2006.01)
*A61G 7/015* (2006.01)
(Continued)

(52) U.S. Cl.
CPC ............ *A61G 13/04* (2013.01); *A61B 6/0407* (2013.01); *A61G 7/015* (2013.01); *A61G 13/02* (2013.01);
(Continued)

(58) Field of Classification Search
CPC .... A61G 13/04; A61G 13/123; A61G 13/122; A61G 13/06; A61G 13/104; A61G 13/08;
(Continued)

(56) References Cited

U.S. PATENT DOCUMENTS 3,814,414 A * 6/1974 Chapa ...................... A61B 6/04
128/873
6,260,220 B1 * 7/2001 Lamb ...................... A61G 13/02
5/601
(Continued)

OTHER PUBLICATIONS

U.S. Appl. No. 15/631,911, filed Jun. 23, 2017, Jackson.
(Continued)

*Primary Examiner* — Nicholas F Polito
*Assistant Examiner* — Myles A Throop

(57) ABSTRACT

A surgical table comprising a base and a patient support supported between opposed ends of the base, each opposed end including a pitch/roll assembly. The base is configured such that the patient support can be rolled and pitched relative to the opposed ends via the pitch/roll assemblies such that the roll axis of each pitch/roll assembly remains coaxial regardless of how the patient support is pitched or rolled relative to the base. The patient support includes an outer frame and an inner frame supported on, and displaceable relative to, the outer frame. The inner frame is further articulating about, and relative to, itself. The outer frame is rigid in that it does not change configurations.

23 Claims, 71 Drawing Sheets

Related U.S. Application Data

(60) Provisional application No. 62/021,481, filed on Jul. 7, 2014, provisional application No. 62/118,282, filed on Feb. 19, 2015, provisional application No. 62/118,305, filed on Feb. 19, 2015, provisional application No. 62/021,630, filed on Jul. 7, 2014, provisional application No. 62/021,643, filed on Jul. 7, 2014, provisional application No. 62/021,595, filed on Jul. 7, 2014.

(51) Int. Cl.
*A61G 13/06* (2006.01)
*A61G 13/10* (2006.01)
*A61G 13/12* (2006.01)
*A61G 13/02* (2006.01)
*A61B 6/04* (2006.01)
*A61G 13/08* (2006.01)
*E05D 9/00* (2006.01)
*E05D 11/00* (2006.01)

(52) U.S. Cl.
CPC .............. *A61G 13/06* (2013.01); *A61G 13/08* (2013.01); *A61G 13/10* (2013.01); *A61G 13/104* (2013.01); *A61G 13/122* (2013.01); *A61G 13/123* (2013.01); *E05D 9/00* (2013.01); *E05D 11/0054* (2013.01); *A61G 2200/327* (2013.01); *E05D 2011/0072* (2013.01)

(58) Field of Classification Search
CPC ........ A61G 13/02; A61G 13/10; A61G 7/015; A61G 2200/327; A61G 13/054; A61G 13/1295; E05D 11/0054; E05D 9/00; E05D 2011/0072; A61B 6/0407
See application file for complete search history.

(56) References Cited

U.S. PATENT DOCUMENTS

| | | | |
|---|---|---|---|
| 8,826,474 B2 | 9/2014 | Jackson | |
| 8,826,475 B2 | 9/2014 | Jackson | |
| 8,839,471 B2 | 9/2014 | Jackson | |
| 8,856,986 B2 | 10/2014 | Jackson | |
| 8,938,826 B2 | 1/2015 | Jackson | |
| 8,978,180 B2 | 3/2015 | Jackson | |
| 9,180,062 B2 | 11/2015 | Jackson | |
| 9,186,291 B2 | 11/2015 | Jackson et al. | |
| 9,198,817 B2 | 12/2015 | Jackson | |
| 9,205,013 B2 | 12/2015 | Jackson | |
| 9,211,223 B2 | 12/2015 | Jackson | |
| 9,226,865 B2 | 1/2016 | Jackson et al. | |
| 9,265,679 B2 | 2/2016 | Jackson | |
| 9,289,342 B2 | 3/2016 | Jackson | |
| 9,295,433 B2 | 3/2016 | Jackson et al. | |
| 9,301,897 B2 | 4/2016 | Jackson | |
| 9,308,145 B2 | 4/2016 | Jackson | |
| 9,339,430 B2 | 5/2016 | Jackson et al. | |
| 9,358,170 B2 | 6/2016 | Jackson | |
| 9,364,380 B2 | 6/2016 | Jackson | |
| 9,402,775 B2 * | 8/2016 | Jackson | A61G 13/02 |
| 9,414,982 B2 | 8/2016 | Jackson | |
| 9,456,945 B2 | 10/2016 | Jackson | |
| 9,468,576 B2 | 10/2016 | Jackson | |
| 9,504,622 B2 | 11/2016 | Jackson | |
| 9,510,987 B2 | 12/2016 | Jackson et al. | |
| 9,549,863 B2 * | 1/2017 | Jackson | A61G 13/06 |
| 9,561,145 B2 | 2/2017 | Jackson et al. | |
| 9,572,734 B2 | 2/2017 | Jackson et al. | |
| 9,610,206 B2 | 4/2017 | Jackson | |
| 9,622,928 B2 | 4/2017 | Jackson et al. | |
| 9,629,766 B2 | 4/2017 | Jackson et al. | |
| 9,636,266 B2 | 5/2017 | Jackson et al. | |
| 9,642,760 B2 | 5/2017 | Jackson et al. | |
| 9,687,399 B2 | 6/2017 | Jackson et al. | |
| 9,744,087 B2 | 8/2017 | Jackson | |
| 9,744,089 B2 | 8/2017 | Jackson | |
| 9,757,300 B2 | 9/2017 | Jackson | |
| 2011/0107516 A1 * | 5/2011 | Jackson | A61G 13/04 5/608 |
| 2011/0119940 A1 * | 5/2011 | Zerhusen | A61G 7/015 33/333 |
| 2013/0111666 A1 | 5/2013 | Jackson | |
| 2013/0133137 A1 | 5/2013 | Jackson | |
| 2013/0269710 A1 * | 10/2013 | Hight | A61G 13/04 128/845 |
| 2014/0109316 A1 * | 4/2014 | Jackson | A61G 13/0036 5/601 |
| 2014/0201914 A1 | 7/2014 | Jackson | |
| 2014/0317847 A1 | 10/2014 | Jackson | |
| 2015/0059094 A1 | 3/2015 | Jackson | |
| 2015/0150743 A1 | 6/2015 | Jackson | |
| 2016/0000627 A1 * | 1/2016 | Jackson | A61G 13/02 5/608 |
| 2016/0038364 A1 | 2/2016 | Jackson | |
| 2016/0213542 A1 | 7/2016 | Jackson | |
| 2016/0317373 A1 | 11/2016 | Jackson et al. | |
| 2016/0346148 A1 | 12/2016 | Jackson et al. | |
| 2016/0346149 A1 | 12/2016 | Jackson et al. | |
| 2017/0071809 A1 | 3/2017 | Jackson et al. | |
| 2017/0151115 A1 | 6/2017 | Jackson | |
| 2017/0181908 A1 | 6/2017 | Jackson et al. | |
| 2017/0189254 A1 | 7/2017 | Jackson et al. | |
| 2017/0202523 A1 | 7/2017 | Jackson | |

OTHER PUBLICATIONS

U.S. Appl. No. 15/660,336, filed Jul. 26, 2017, Jackson.
U.S. Appl. No. 15/661,261, filed Jul. 27, 2017, Jackson.
U.S. Appl. No. 15/723,972, filed Oct. 3, 2017, Jackson.

* cited by examiner

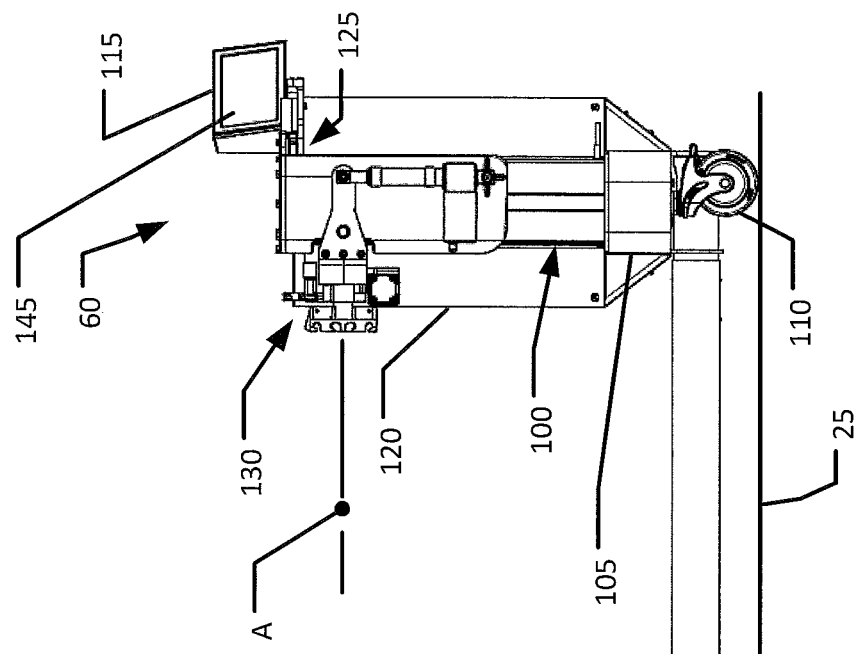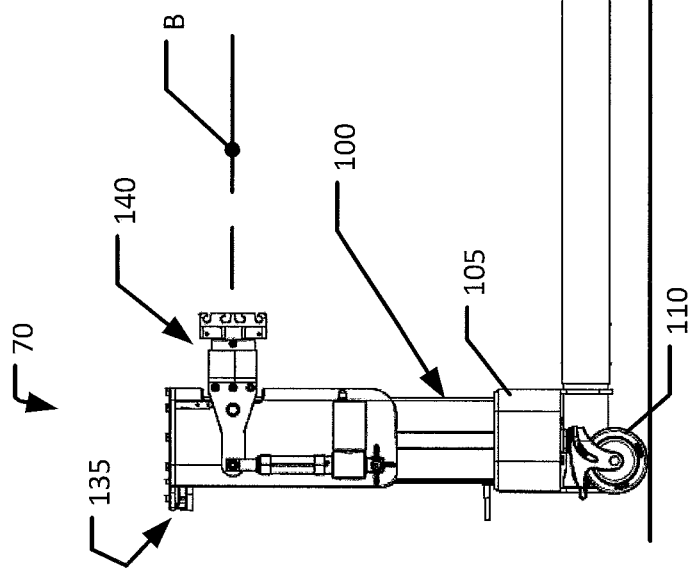
FIG. 7

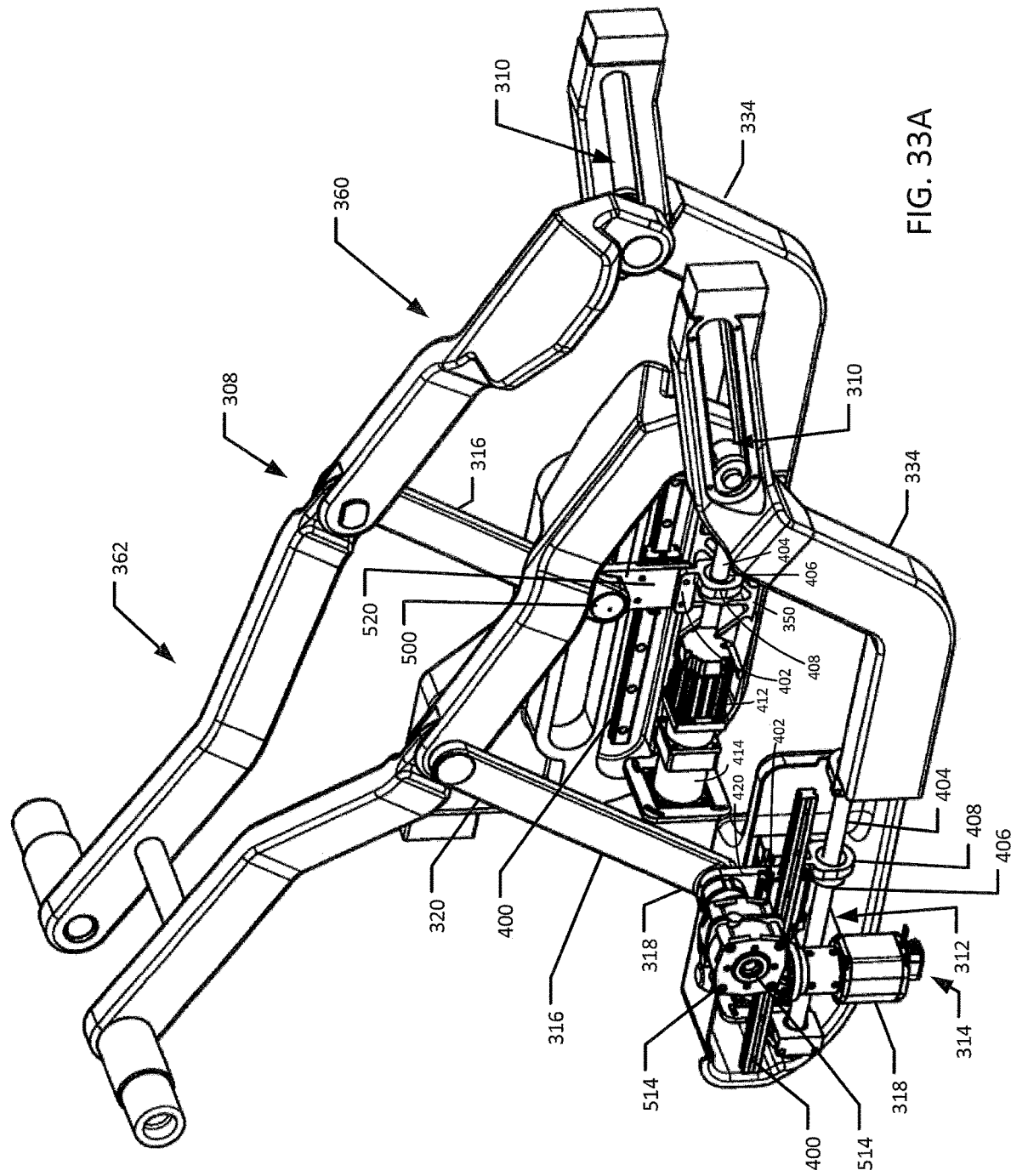

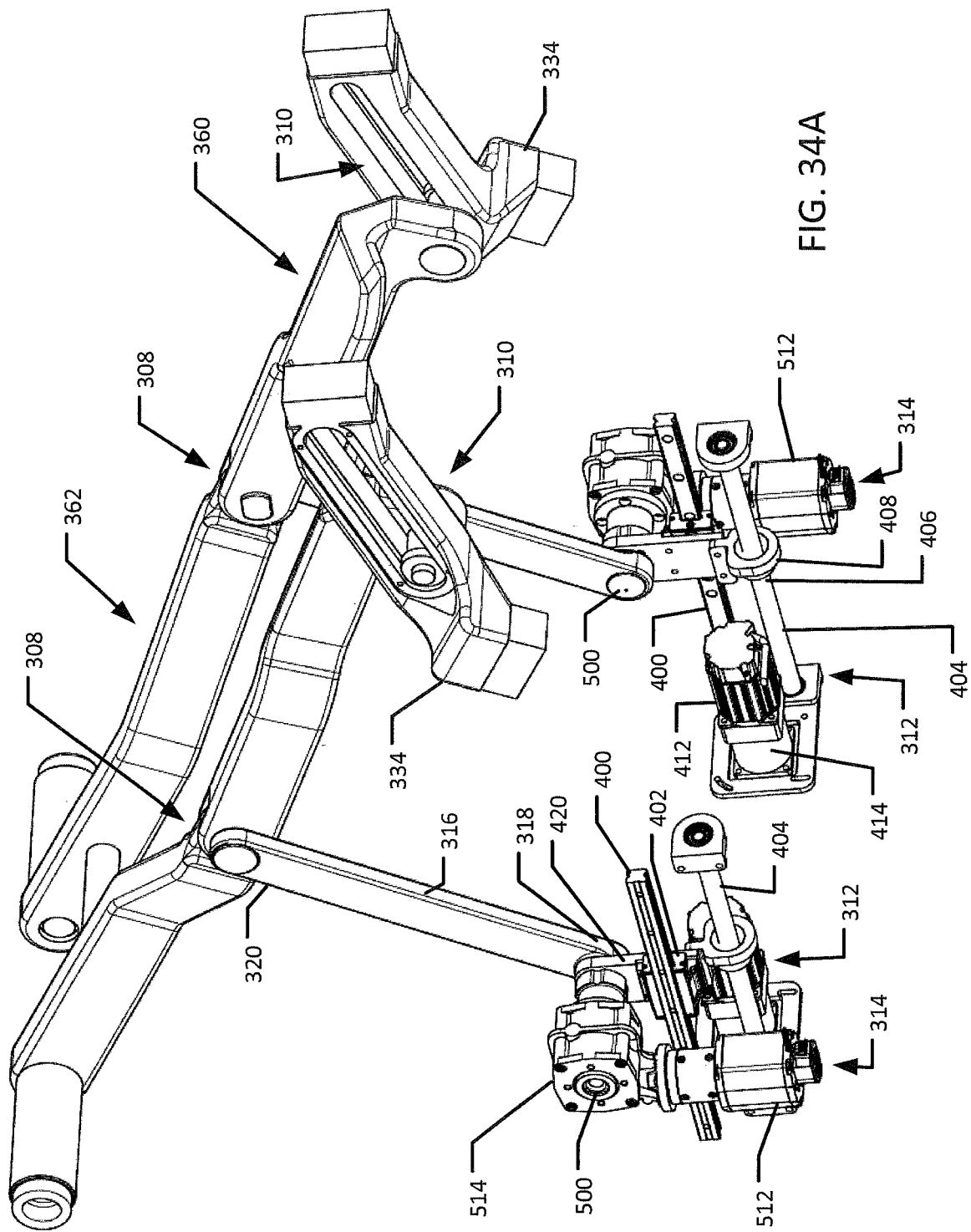

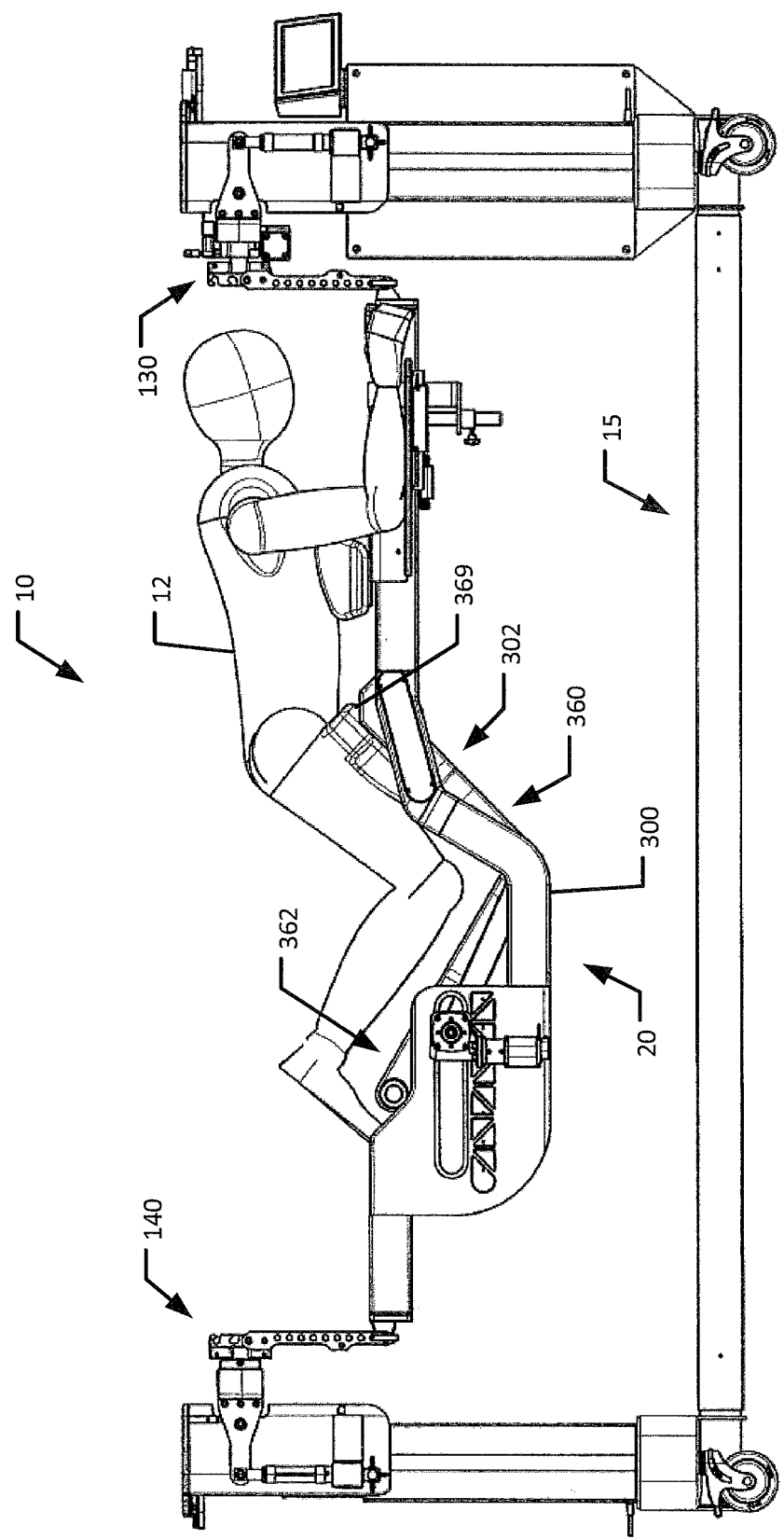

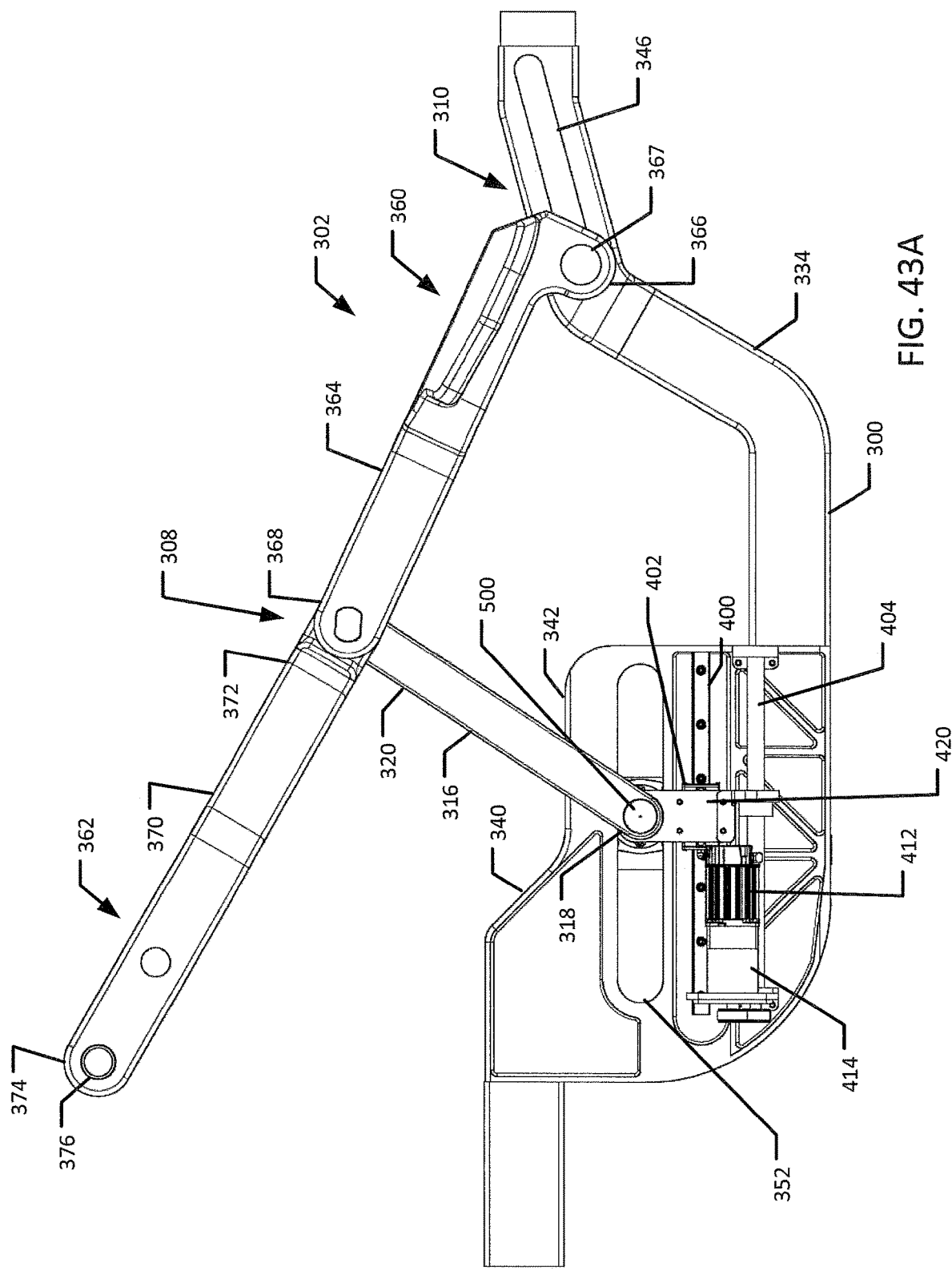

SURGICAL TABLE WITH PATIENT SUPPORT HAVING FLEXIBLE INNER FRAME SUPPORTED ON RIGID OUTER FRAME

CROSS-REFERENCE TO RELATED APPLICATIONS

This application is a divisional application of U.S. patent application Ser. No. 14/793,050, filed Jul. 7, 2015, which is hereby incorporated by reference in its entirety into the present application.

U.S. patent application Ser. No. 14/793,050 claims priority under 35 U.S.C. § 119 to U.S. Provisional Patent Application No. 62/021,481, filed on Jul. 7, 2014, titled "RADIOLUCENT HINGE FOR A SURGICAL TABLE", which is hereby incorporated by reference in its entirety into the present application.

U.S. patent application Ser. No. 14/793,050 claims priority under 35 U.S.C. § 119 to U.S. Provisional Patent Application No. 62/118,282, filed on Feb. 19, 2015, titled "RADIOLUCENT HINGE FOR A SURGICAL TABLE", which is hereby incorporated by reference in its entirety into the present application.

U.S. patent application Ser. No. 14/793,050 claims priority under 35 U.S.C. § 119 to U.S. Provisional Patent Application No. 62/118,305, filed on Feb. 19, 2015, titled "SINGLE COLUMN PATIENT POSITIONING AND SUPPORT STRUCTURE", which is hereby incorporated by reference in its entirety into the present application.

U.S. patent application Ser. No. 14/793,050 claims priority under 35 U.S.C. § 119 to U.S. Provisional Patent Application No. 62/021,630, filed on Jul. 7, 2014, titled "SURGICAL TABLE WITH PATIENT SUPPORT HAVING FLEXIBLE INNER FRAME SUPPORTED ON RIGID OUTER FRAME", which is hereby incorporated by reference in its entirety into the present application.

U.S. patent application Ser. No. 14/793,050 claims priority under 35 U.S.C. § 119 to U.S. Provisional Patent Application No. 62/021,643, filed on Jul. 7, 2014, titled "SINGLE COLUMN PATIENT POSITIONING SUPPORT STRUCTURE", which is hereby incorporated by reference in its entirety into the present application.

U.S. patent application Ser. No. 14/793,050 claims priority under 35 U.S.C. § 119 to U.S. Provisional Patent Application No. 62/021,595, filed on Jul. 7, 2014, titled "PATIENT SUPPORT STRUCTURE WITH PIVOTING AND TRANSLATING HINGE", which is hereby incorporated by reference in its entirety into the present application.

TECHNICAL FIELD

The present disclosure generally relates to surgical tables and associated methods. More specifically, the present disclosure relates to patient positionable surgical tables and associated methods.

BACKGROUND OF THE INVENTION

Current surgical approaches often utilize surgical procedures involving multiple access angles to a surgical site. For example, some surgical procedures move the patient to different positions (e.g. Trendelenburg, reverse Trendelenburg, supine, prone, lateral-decibitus, etc.) throughout the procedure to access the surgical site from different angles. Further, some surgical procedures, such as spinal surgery, may involve access through more than one surgical site. Because these sites may not be in the same plane or anatomical location, the patient needs to be moved to and supported in different positions throughout the procedure. However, many conventional tables providing adjustable positions have excessive movement of the table base and are overly large with respect to floor space. Further, many conventional tables have complex and expensive mechanical arrangements.

It is with these observations in mind, among others, that various aspects of the present disclosure were conceived and developed.

SUMMARY OF THE INVENTION

Disclosed herein is a surgical table comprising a base and a patient support supported between opposed ends of the base, each opposed end including a pitch/roll assembly. The base is configured such that the patient support can be rolled and pitched relative to the opposed ends via the pitch/roll assemblies such that the roll axis of each pitch/roll assembly remains coaxial regardless of how the patient support is pitched or rolled relative to the base. The patient support includes an outer frame and an inner frame supported on, and displaceable relative to, the outer frame. The inner frame is further articulating about, and relative to, itself. The outer frame is rigid in that it does not change configurations.

Aspects of the present disclosure involve a surgical table for supporting and positioning a patient above a floor. The surgical table may include a base and a patient support. The base may be supported on the floor and may include a first end support and a second end support opposite the first end support. The patient support may include a longitudinal axis, an outer frame, and an inner frame movably coupled with the outer frame at a hinge having an axis of rotation that is transverse to the longitudinal axis. The outer frame may include a first end operably coupled with the first end support and a second end operably coupled with the second end support. The axis of rotation may be configured to displace in a direction of the longitudinal axis between the first end and the second end when the inner frame articulates relative to the outer frame.

Aspects of the present disclosure may also involve a surgical table for supporting and positioning a patient above a floor. The surgical table may include a base and a patient support. The base may be supported on the floor and may include a first end support and a second end support opposite the first end support. The patient support may include a longitudinal axis, an outer frame, an inner frame movably coupled with the outer frame at a hinge having an axis of rotation that is transverse to the longitudinal axis, and a drive assembly. The outer frame may include a first end operably coupled with the first end support and a second end operably coupled with the second end support. The inner frame may include an upper leg member coupled with a lower leg member at an articulating joint. The drive assembly may include at least one motor configured to displace the inner frame relative to the outer frame and articulate the upper leg member relative to the lower leg member.

Aspects of the present disclosure may also involve a base for a surgical table for supporting and positioning a patient above a floor. The base may include a first end support and a second end support opposing the first end support. A patient support structure may be coupled with the first end support via a first connection assembly that includes a first roll assembly and a first pitch assembly. The patient support may be coupled with the second end support via a second connection assembly that includes a second roll assembly and a second pitch assembly. The patient support may be configured to roll about a roll axis via the first and second roll assemblies. The pitch assemblies may be configured to actively maintain coaxial alignment of the first and second roll assemblies by pitching or angling the first and second roll assemblies upward or downward when the first or second end supports change elevation relative to each other. Each of the pitch assemblies may include at least one linear drive to actively maintain the coaxial alignment.

BRIEF DESCRIPTION OF THE DRAWINGS

The above and further features, advantages and benefits of the invention will be apparent upon consideration of the descriptions herein taken in conjunction with the accompanying drawings, in which:

FIG. 7 is a right side elevation of the base of FIG. 5;

FIG. 33A is the same view as FIG. 31, except in an assembled state;

FIGS. 34A-34C illustrate same respective conditions and essentially the same components as FIGS. 33A-33C, except from a lower perspective;

FIGS. 38A-38B are of the same view as FIG. 3, except, instead of the inner frame being in a neutral position as depicted in FIG. 3, the inner frame is in an elevated position and a lowered position, respectively;

FIGS. 43A-43C are right side elevation views of the left recessed region of the outer frame and corresponding left drive assembly, link arm, and inner frame components, the inner frame depicted in the elevated position, the neutral position and the lower position, respectively;

DETAILED DESCRIPTION OF THE PREFERRED EMBODIMENTS

Disclosed herein is a surgical table 10 comprising a base 15 and a patient support 20 supported between opposed ends of the base, each opposed end including a pitch/roll assembly. The base is configured such that the patient support can be rolled and pitched relative to the opposed ends via the pitch/roll assemblies such that the roll axis of each pitch/roll assembly remains coaxial regardless of how the patient support is pitched or rolled relative to the base. The patient support includes an outer frame and an inner frame supported on, and displaceable relative to, the outer frame. The inner frame is further articulating about, and relative to, itself. The outer frame is rigid in that it does not change configurations. The surgical table 10 is advantageous for a number of reasons, including, but not limited to, having decreased floor space requirements, being less expensive to build, and providing a wide range of patient positions and the ability to transition between those positions while maintaining the surgical site steady.

Figure 1:
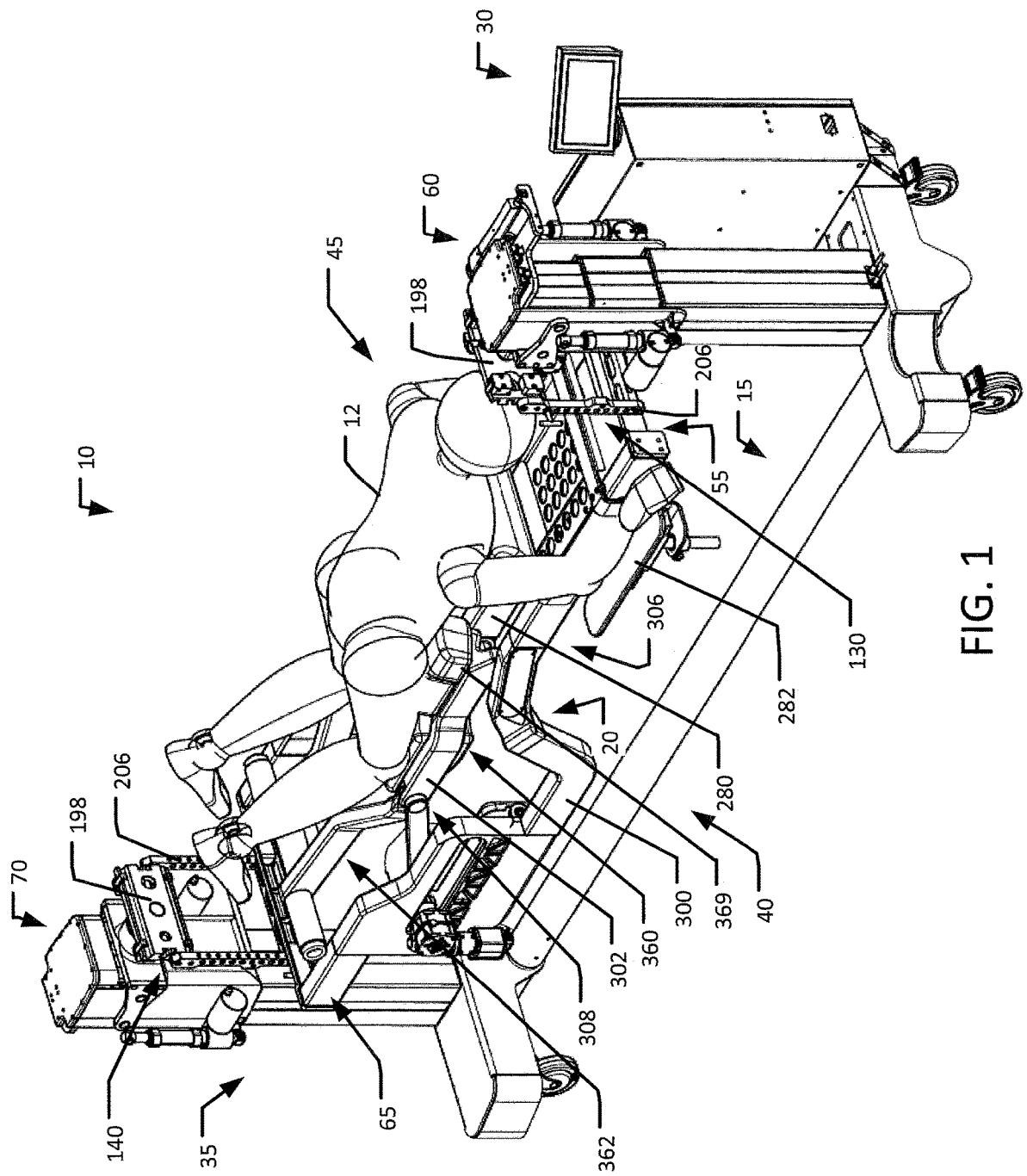
FIG. 1 is an isometric view from a right side and head end perspective of an embodiment of a surgical table with a patient supported thereon in a prone position and an inner frame of the patient support in a neutral position.
Figure 2:
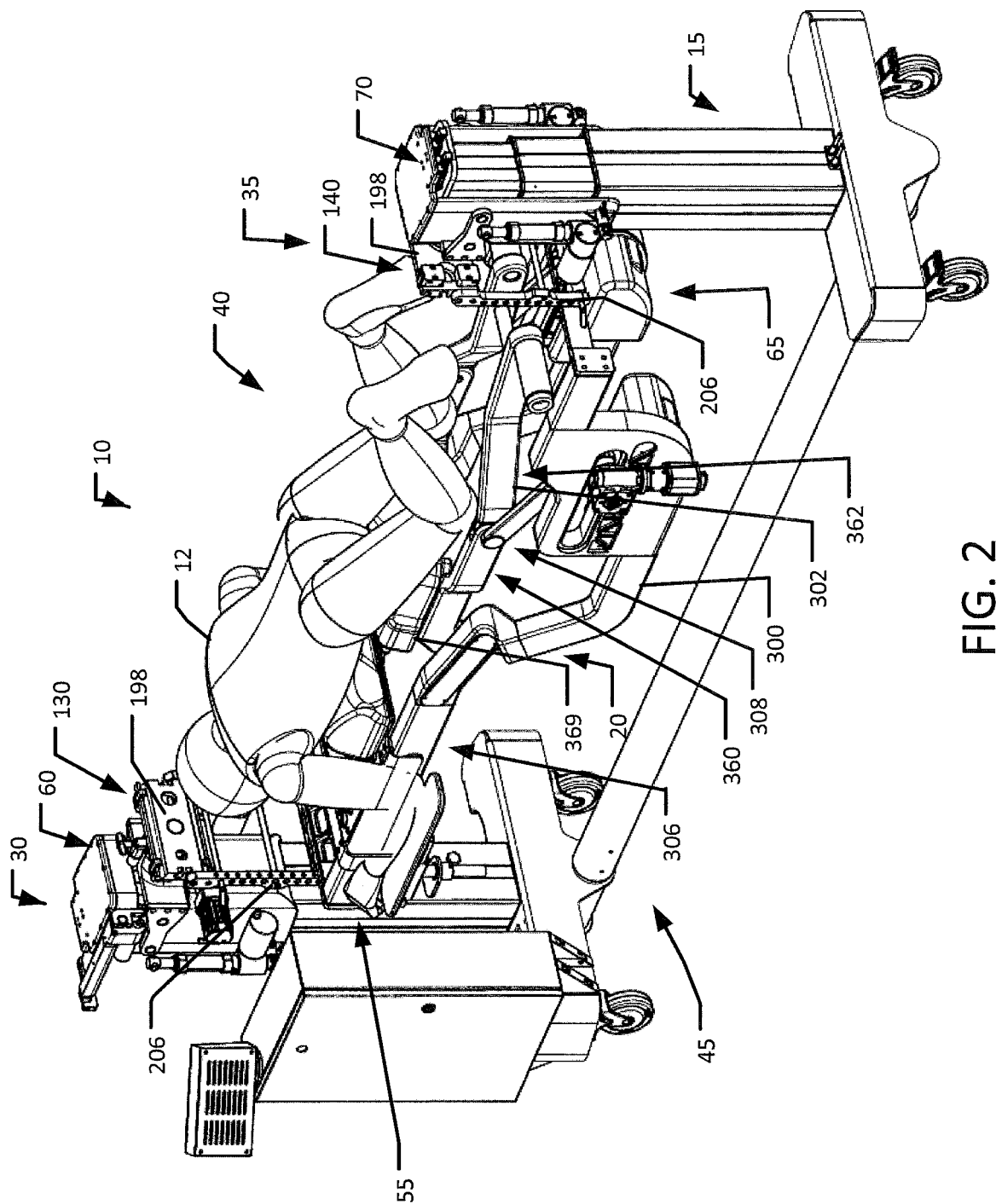
FIG. 2 is an isometric view from a left side and foot end perspective of the surgical table and patient of FIG. 1.
Figure 3:
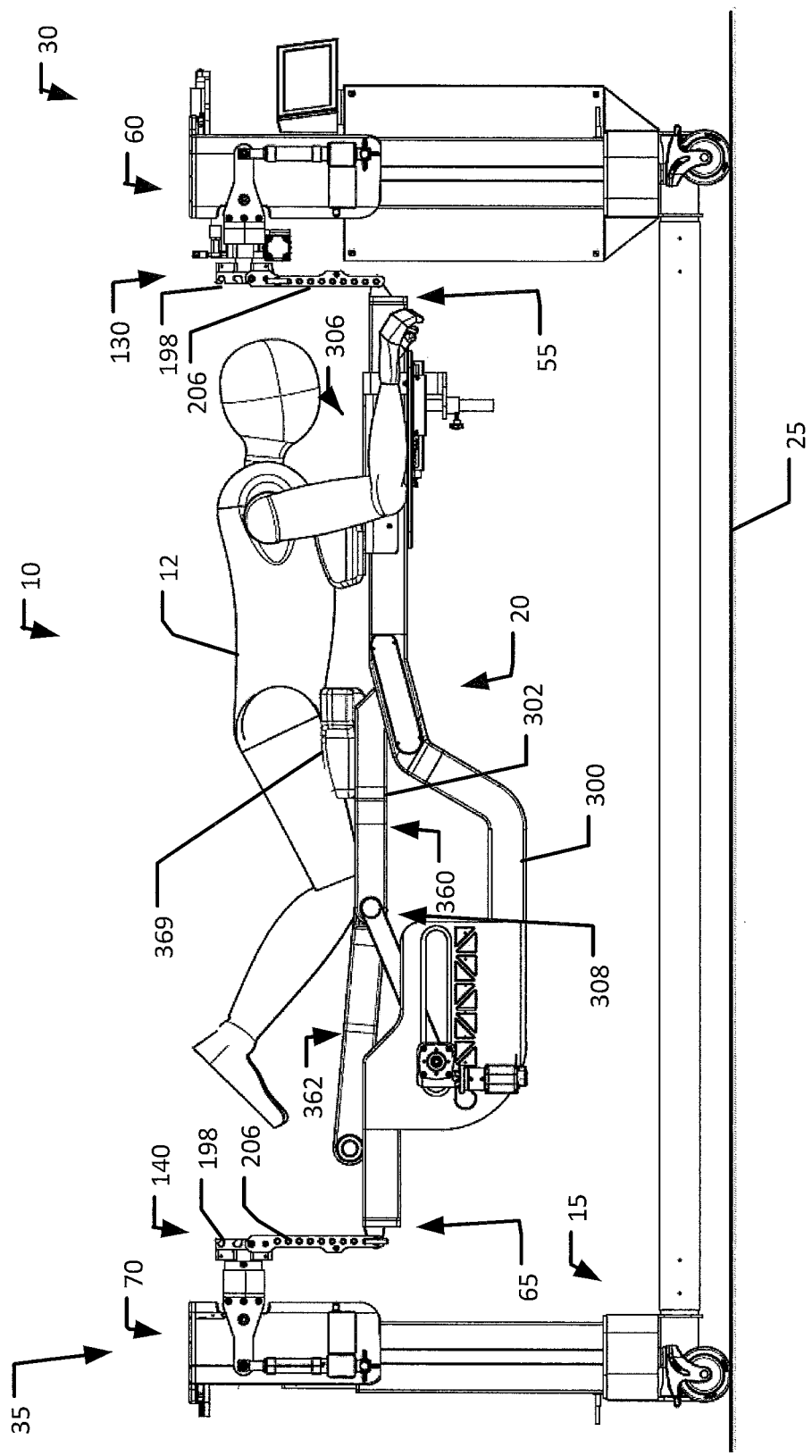
FIG. 3 is a right side elevation of the surgical table and patient of FIG. 1.
Figure 4:
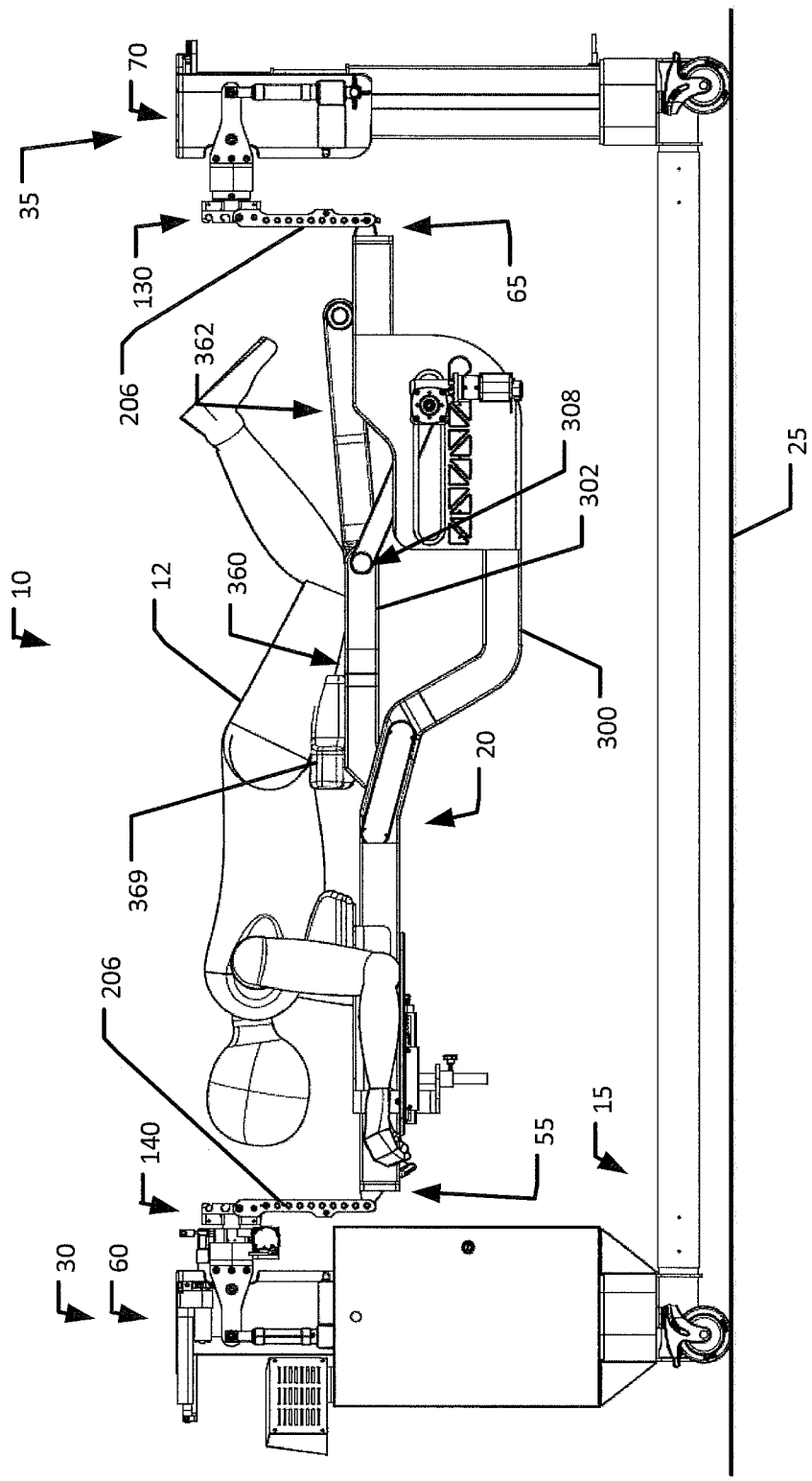
FIG. 4 is a left side elevation of the surgical table and patient of FIG. 1.

To begin the detailed discussion of an embodiment of the surgical table 10, reference is made to FIGS. 1-4. FIG. 1 is an isometric view from a right side and head end perspective of an embodiment of the surgical table 10 with a patient 12 supported thereon in a prone position. FIG. 2 is an isometric view from a left side and foot end perspective of the surgical table 10 and patient 12 of FIG. 1. FIGS. 3 and 4 are, respectively, a right side elevation and a left side elevation of the surgical table 10 and patient 12 of FIG. 1.

As shown in FIGS. 1-4, the table 10 includes a base 15 and a patient support 20. The base 15 supports the patient support 20 above a floor surface 25 on which the base 15 rests. The table 10 includes a head end 30, foot end 35, a right patient side 40 and a left patient side 45, each patient side 40, 45 of the table 10 corresponding to an adjacent side of the patient 12 when the patient 12 is laying prone on the patient support 20, as can be understood from FIGS. 1-4. The designations of the sides 40, 45 as being right or left have no meaning other than for purposes of facilitating the discussion herein.

As illustrated in FIGS. 1-4, a head end 55 of the patient support 20 is coupled to a head end 60 of the base 15, and a foot end 65 of the patient support 20 is coupled to a foot end 70 of the base 15. Thus, the patient support 20 extends lengthwise between the head and foot ends 60, 70 of the base 15. Further, the patient support 20 and base 15 are configured such that the patient support can both roll and pitch between the head and foot ends 60, 70 of the base 15, as discussed in detail below.

I. The Base

Figure 5:
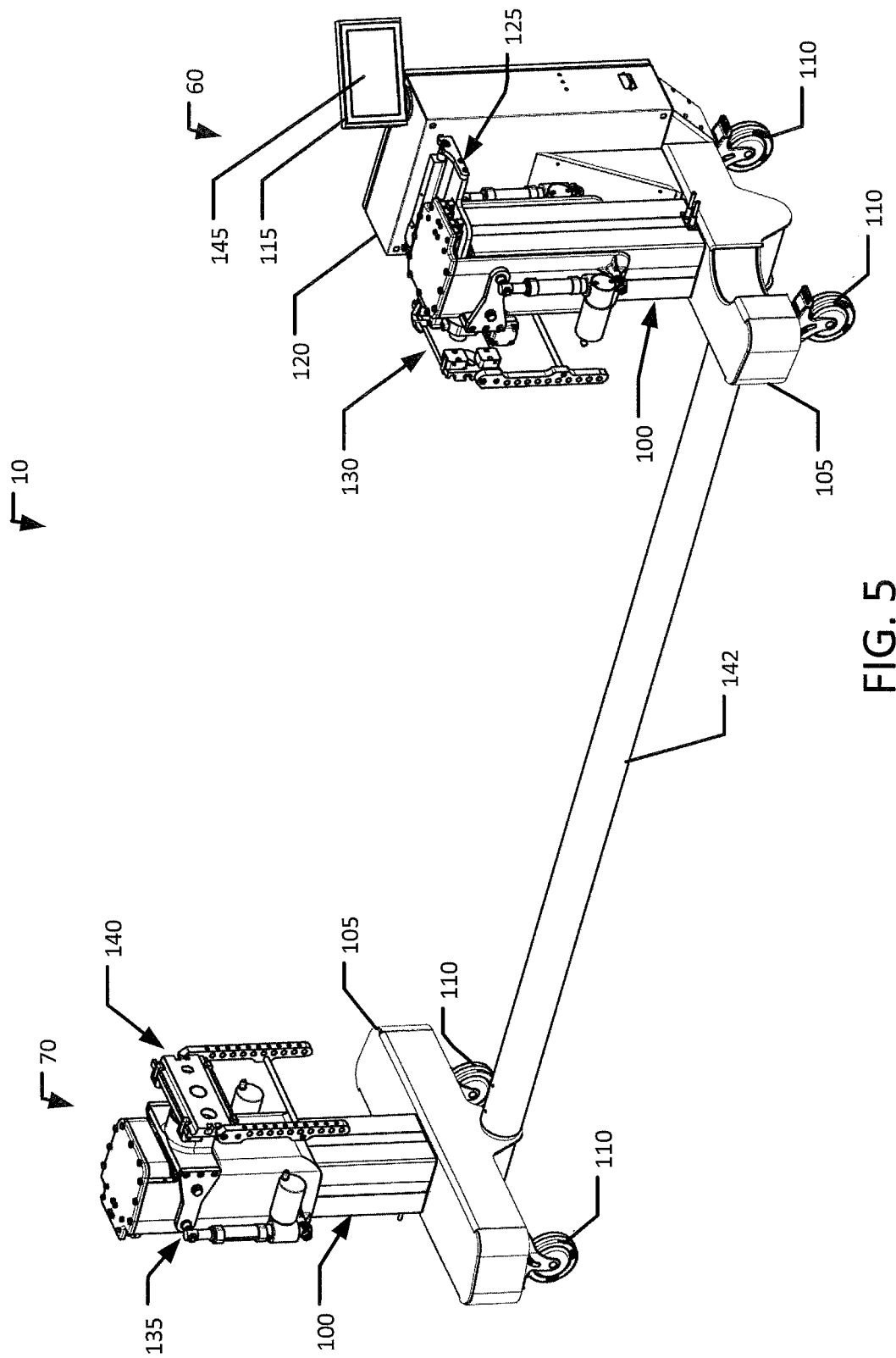
FIG. 5 is an isometric view from a right side and head end perspective of the base of the surgical table of FIG. 1.
Figure 6:
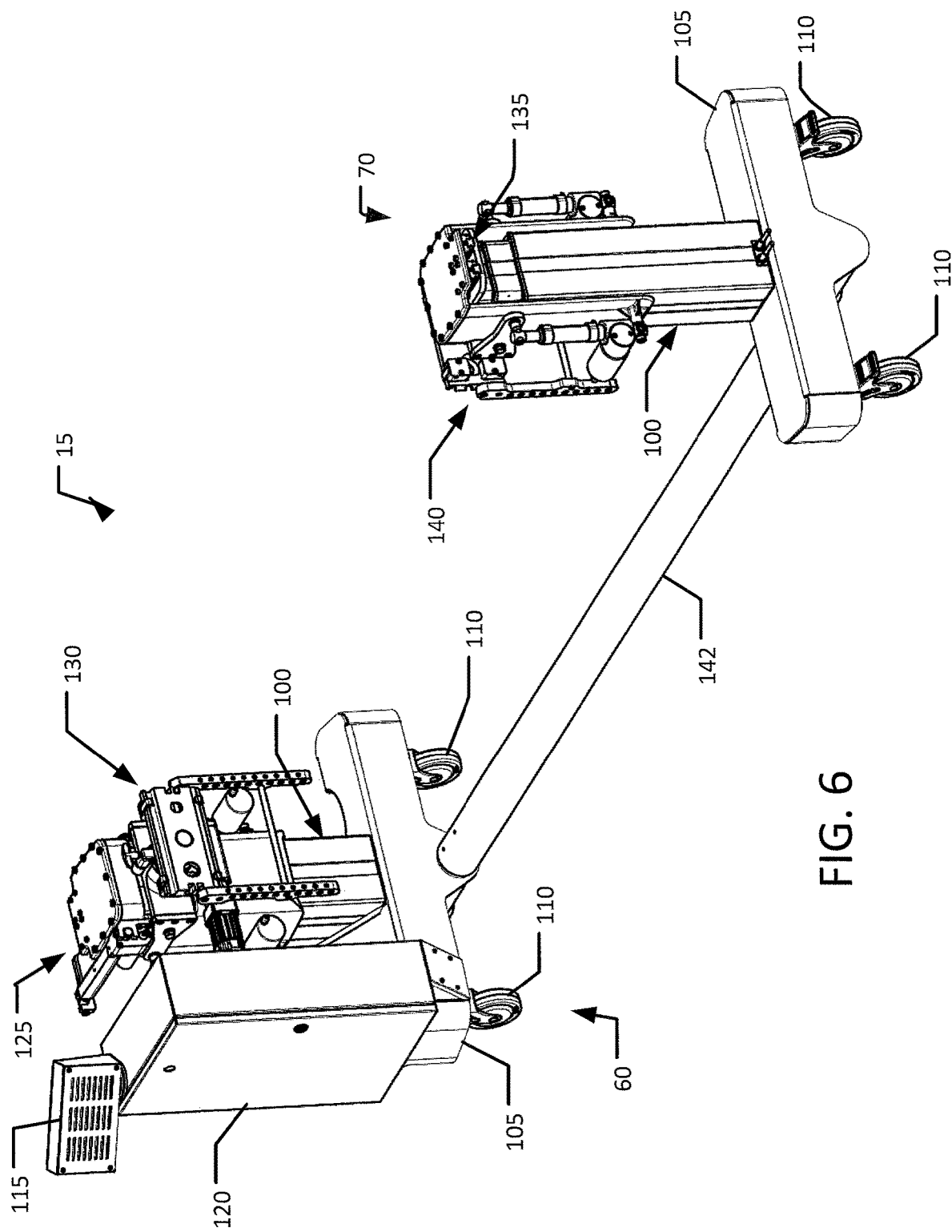
FIG. 6 is an isometric view from a left side and foot end perspective of the base of FIG. 5.

To begin the detailed discussion of the base 15, reference is made to FIGS. 5-7, wherein FIG. 5 is an isometric view from a right side and head end perspective of the base 15 of the surgical table 10 of FIG. 1, FIG. 6 is an isometric view from a left side and foot end perspective of the base 15 of FIG. 5, and FIG. 7 is a right side elevation of the base 15 of FIG. 5. As shown in FIGS. 5-7, the base head end 60 includes a vertical support or column 100, a wheeled base 105 with castors 110, a computer 115, a control box 120, a head end translation assembly 125, and a head end pitch/roll assembly 130. Similarly, the base foot end 70 includes a vertical support 100, a wheeled base 105 with castors 110, a foot end translation assembly 135, and a foot end pitch/roll assembly 140.

As illustrated in FIG. 7, the wheeled bases 105 are supported above the floor surface 25 via their respective castors 110. The castors 110 facilitate the base 15 being rolled along the floor surface 25 and may be of a lockable variety thereby allowing the base 15 to be fixedly located on the floor surface 25.

As depicted in FIGS. 5-7, the wheeled bases 105 are coupled together via a base frame member 142 that extends longitudinally between the opposed wheeled bases 105. The base frame member 142 may be tubular or any other structural shape. Depending on the embodiment, the base frame member 142 may be permanently fixed with respect to its overall length or the base frame member 142 may be adjustable relative to its overall length to allow the opposed wheeled bases 105 to be moved closer together to facilitate a reduced floor footprint of the base 15, thereby facilitating the storage of the base 15. In such an adjustable embodiment, the base frame member 142 may be telescopically configured to allow the opposed wheeled bases 105 to move towards each other for storage of the base 15. Depending on the embodiment, the adjustable base frame member 142 may be manually adjusted or may be equipped with a powered drive mechanism for adjusting the base frame member 142 with respect to its length.

While the base frame member 142 may or may not be adjustable, it should be noted that the base 15 and the patient support 20 used therewith are configured such that the patient may be pitched head down (Trendelenburg), pitched head up (reverse Trendelenburg), rolled right or left, placed in a neutral position, flexed, extended or any combination of the aforementioned positions without the opposed wheeled bases 105 and their associated vertical supports 100 displacing relative to each other. In other words, when the patient is moved through a range of positions on the surgical table 10, the vertical supports 100 will remain fixed relative to each other whatever that range of positions may be. The mechanical arrangements for facilitating such patient displacement while maintaining the vertical supports 100 fixed relative to each other are discussed in detail below.

As indicated in FIGS. 5-7, each vertical support or end support 100 extends vertically upward from its respective wheeled support 105. As discussed in greater detail below, each vertical support 100 is vertically adjustable in height and may be actuated to evenly displace together or displace differing amounts and/or directions relative to each other at the same time or during individual times.

The control box 120 extends vertically upward from the wheeled base 105, and the computer 115 is supported on a top surface of the control box 120. The control box 120 contains electrical wiring, junctions, and other related electrical circuitry associated with the operation and control of the surgical table function directed by the software and central processing unit of the computer according to operator inputs entered into the computer 115 via its user interface, which may be in the form of a touch screen 145 of the computer 115.

The head end pitch/roll assembly 130 and the foot end pitch/roll assembly 140 are movably attached to their respective vertical supports 100 so as to facilitate both pitch and roll of the patient support 20 as described in detail below. As can be understood from FIG. 7, the head end pitch/roll assembly 130 includes a roll axis A, and the foot end pitch/roll assembly 140 includes a roll axis B. As described in detail below, through a combination of mechanical, electrical and software arrangements, these axes A, B may be automatically maintained coaxial with each other through the range of possible patient displacements provided for by the mechanical arrangement of the pitch/roll assemblies 130, 140, the vertical supports 100, and the patient support 20.

As described in detail below, the head end translation assembly 125 and foot end translation assembly 135 are each configured to provide for longitudinal displacement of the respective pitch/roll assembly 130, 140 along the longitudinal axis of the base 15 and relative to the respective vertical support 100 on which the pitch/roll assembly is mounted. In other words, this longitudinal displacement via the head end translation assembly 125 causes the head end pitch/roll assembly 130 to move relative to its vertical support 100 closer or further away from the vertical support 100 of the foot end 70. Similarly, this longitudinal displacement via the foot end translation assembly 135 causes the foot end pitch/roll assembly 140 to move relative to its vertical support 100 closer or further away from the vertical support 100 of the head end 60. Thus, as further described below, the translation assemblies 125, 135 work together to compensate for the change in effective distance between the pitch/roll assemblies 130, 140 brought about by a rigid exterior frame 300 of the patient support 20 changing slope from a horizontal orientation between the opposed vertical supports 100 and a sloped orientation between the opposed vertical supports 100 and vice versa. Because the translation assemblies 125, 135 compensate for such movement of the rigid exterior frame 300, the opposed columns 100 can remain a fixed distance from each other while the exterior rigid frame transitions between horizontal and varying degree of slope, and vice versa.

As will be discussed below in detail, the mechanical configurations of the table 10, namely, the rotation/pitch assemblies 130, 140 and the translation assemblies 125, 135 of the base 15, plus the displacements capability of the inner frame 302 relative to the outer frame 300 of the patient platform 20, combine to make possible articulations and displacements of the patient that keep the surgical field (e.g., the lumbar spine) stable in relation to the floor 25 such that the surgical field does not move up or down or cephalad or caudad in relation to the floor during the articulations or displacements unless the operator purposely intends the surgical field to move up or down or cephalad or caudad in relation to the floor during the articulations or displacements. The coordinated actuation and movement of the mechanical configurations of the base 15 and patient support 20 that allow the patient to be rolled, pitched, flexed, extended, held neutral, etc. while maintaining a stable surgical field are facilitated by software driving the servomotors of the various mechanical arrangements of the table, these servomotors being software synchronized and linked with position and limit-stop sensors.

a. The Head End of the Base

Figure 8:
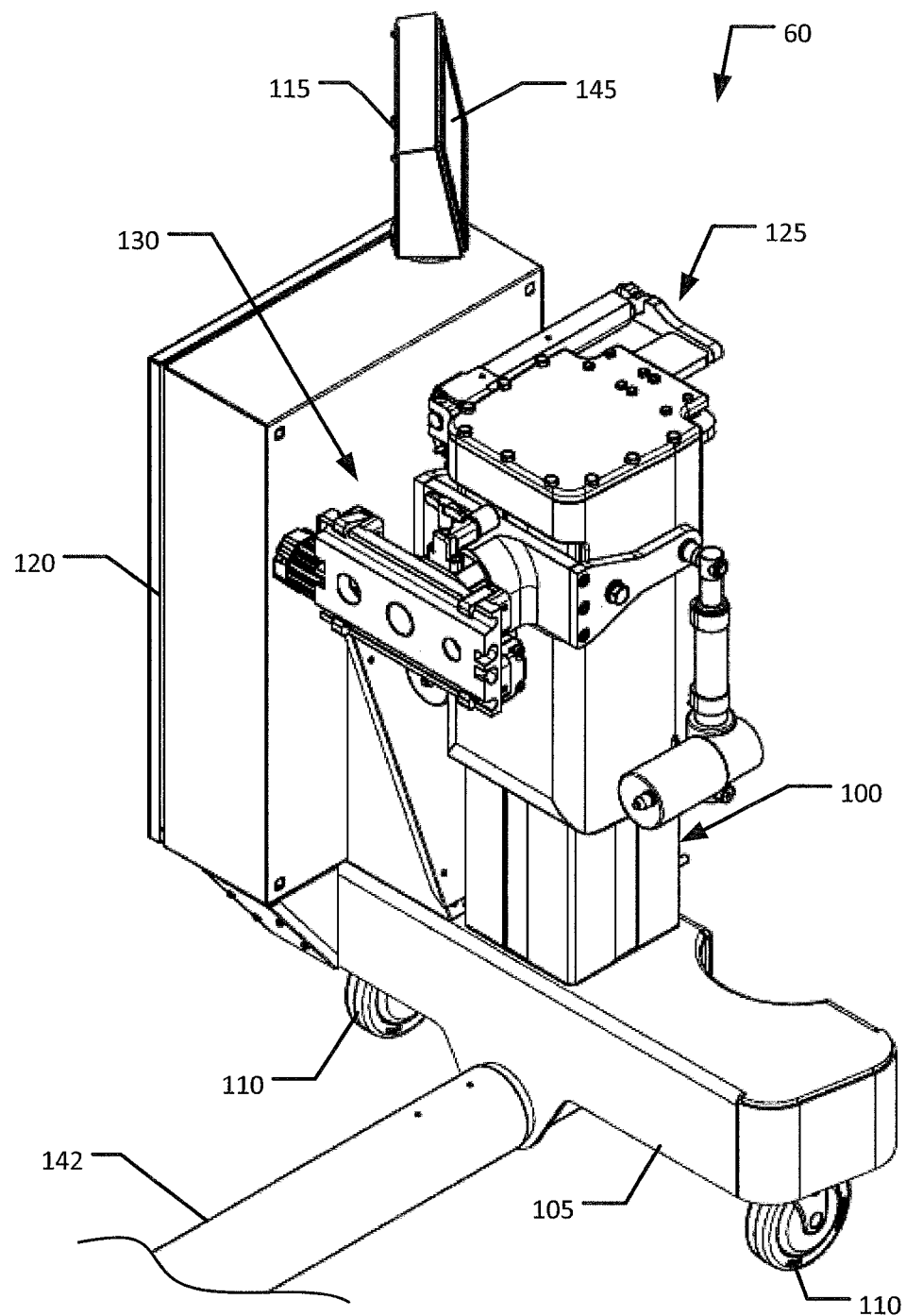
FIG. 8 is a right side isometric view of a front region of the head end of the base of FIG. 1.
Figure 9:
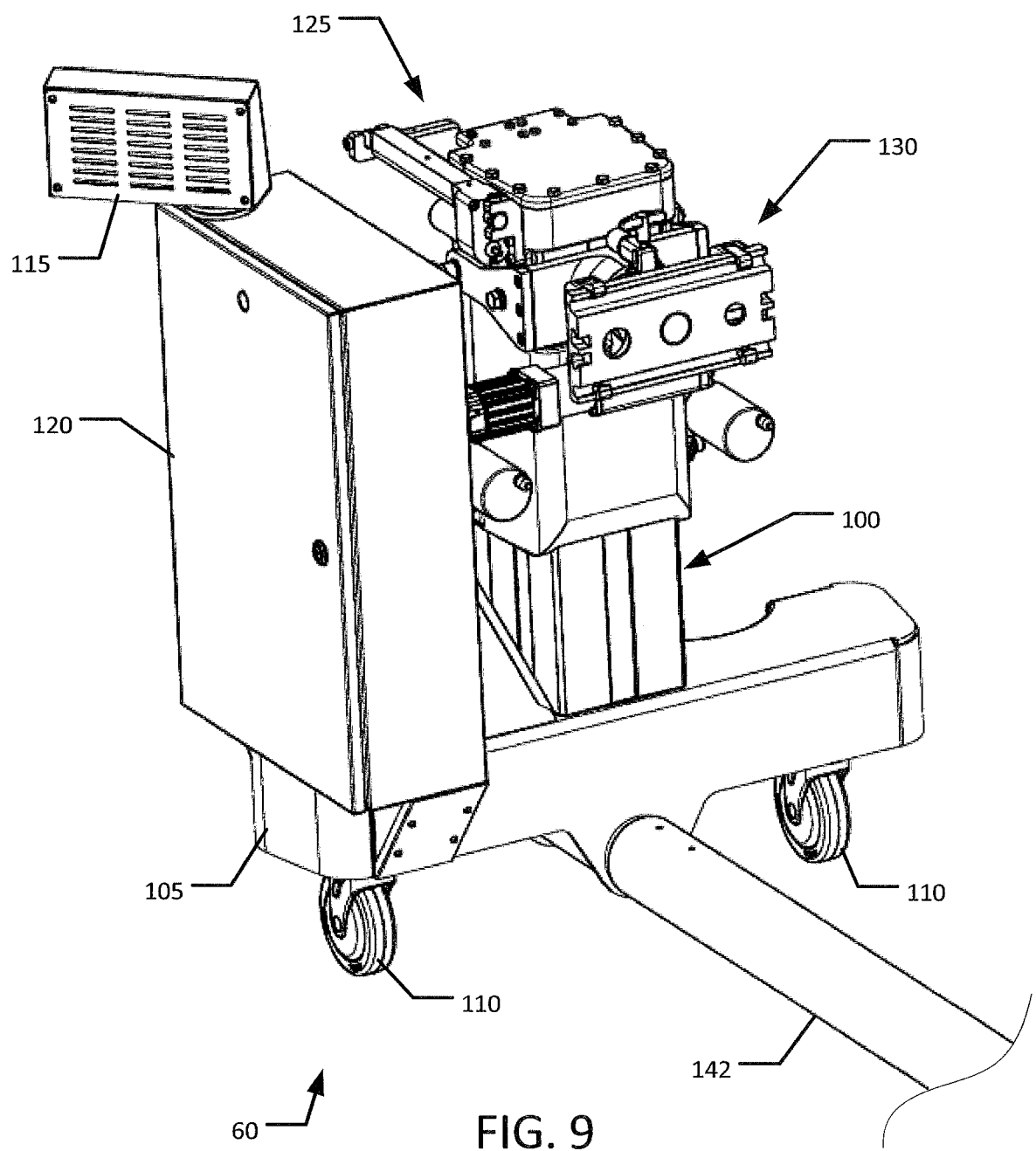
FIG. 9 is a left side isometric view of the front region of the head end of FIG. 8.
Figure 10:
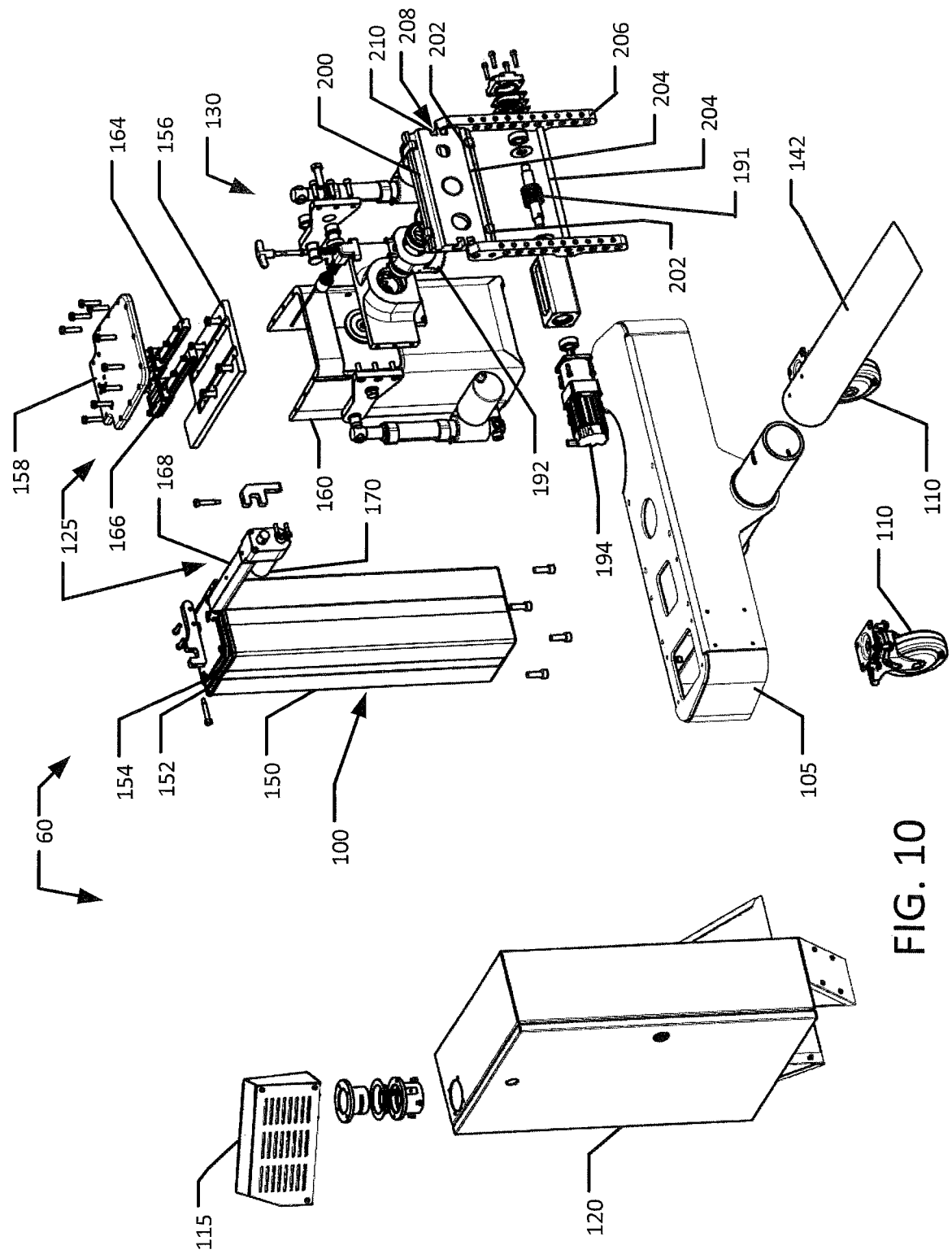
FIG. 10 is an exploded left side isometric view of the front region of the head end of FIG. 8.

To begin the detailed discussion of the head end 60 of the base 15, reference is made to FIGS. 8-10, wherein FIGS. 8-10 are, respectively, a right side isometric view, a left side isometric view, and an exploded left side isometric view of a front region of the head end 60 of the base 15 of FIG. 1. The designations of the head end 60 having front and rear regions have no meaning other than for purposes of facilitating the discussion herein.

As mentioned above and further shown in FIGS. 8-10, the base head end 60 includes the vertical support 100, the wheeled base 105 with castors 110, the computer 115, the control box 120, the head end translation assembly 125, and the head end pitch/roll assembly 130. The head end vertical support 100 of the base 15 extends vertically upward from the wheeled base 105 and is generally centered right-to-left on the wheeled base 105 and centered right-to-left relative to the base frame member 142. The control box 120 also extends vertically upward from the wheeled based 105 and is to the left of the head end vertical support 100. The computer 115 is supported on the control box 120. The head end translation assembly 125 and the head end pitch/roll assembly 130 are found near the top of the head end vertical support 100.

1. The Head End Vertical Support

Figure 11:
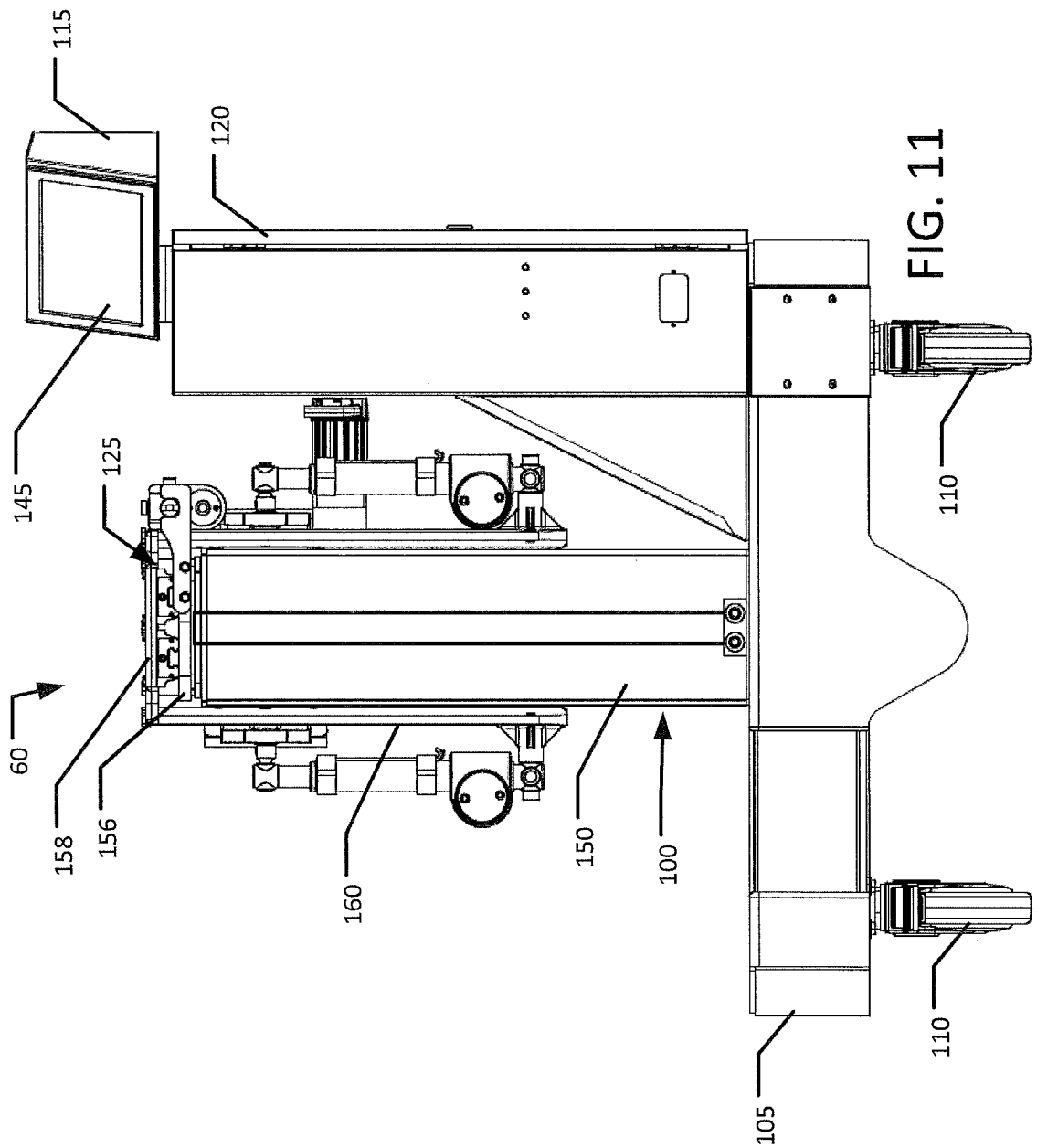
FIG. 11 is an elevation view of a rear region of the head end of FIG. 8.
Figure 12:
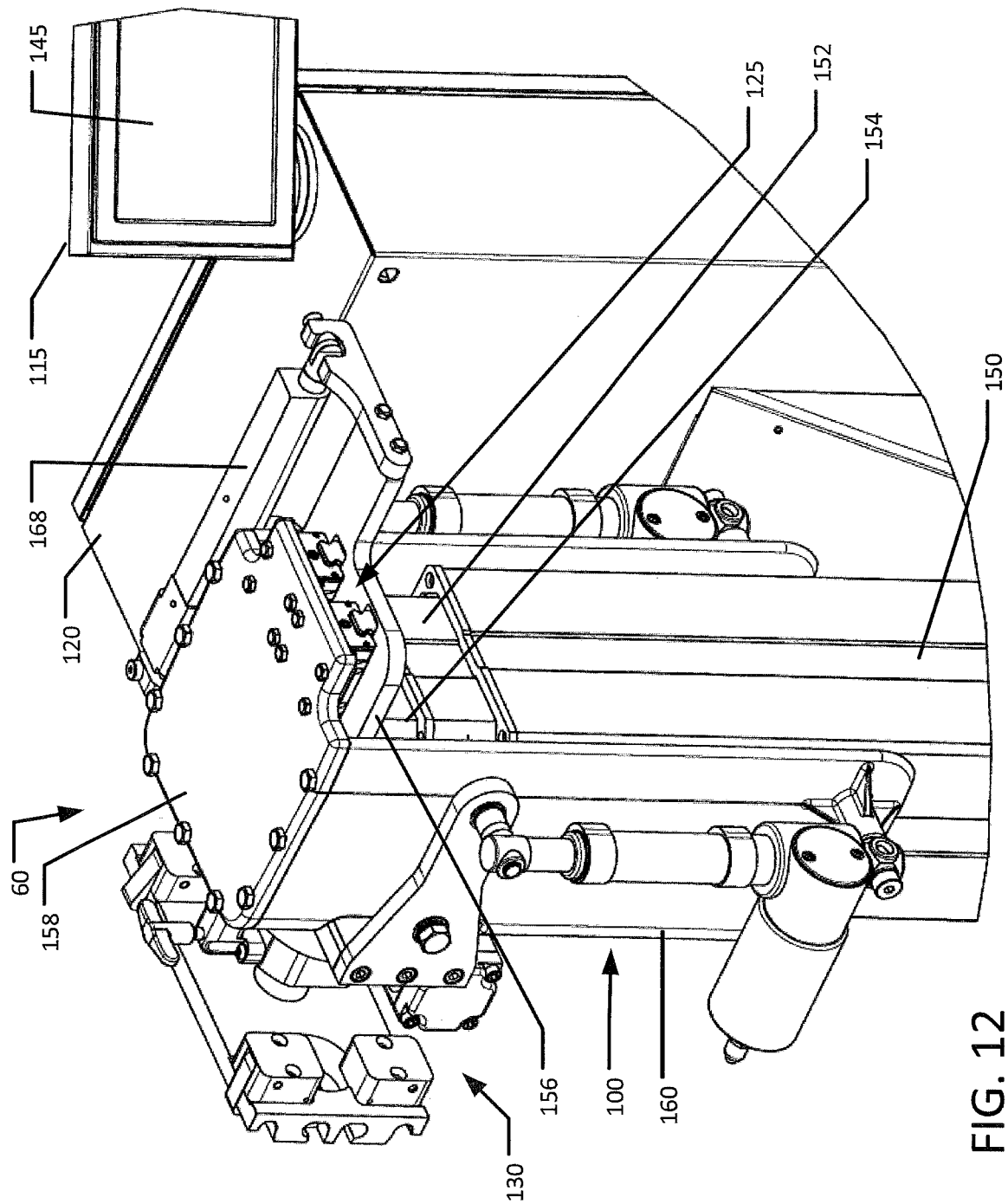
FIG. 12 is a right side isometric view of an upper rear region of the head end of FIG. 11.
Figure 13:
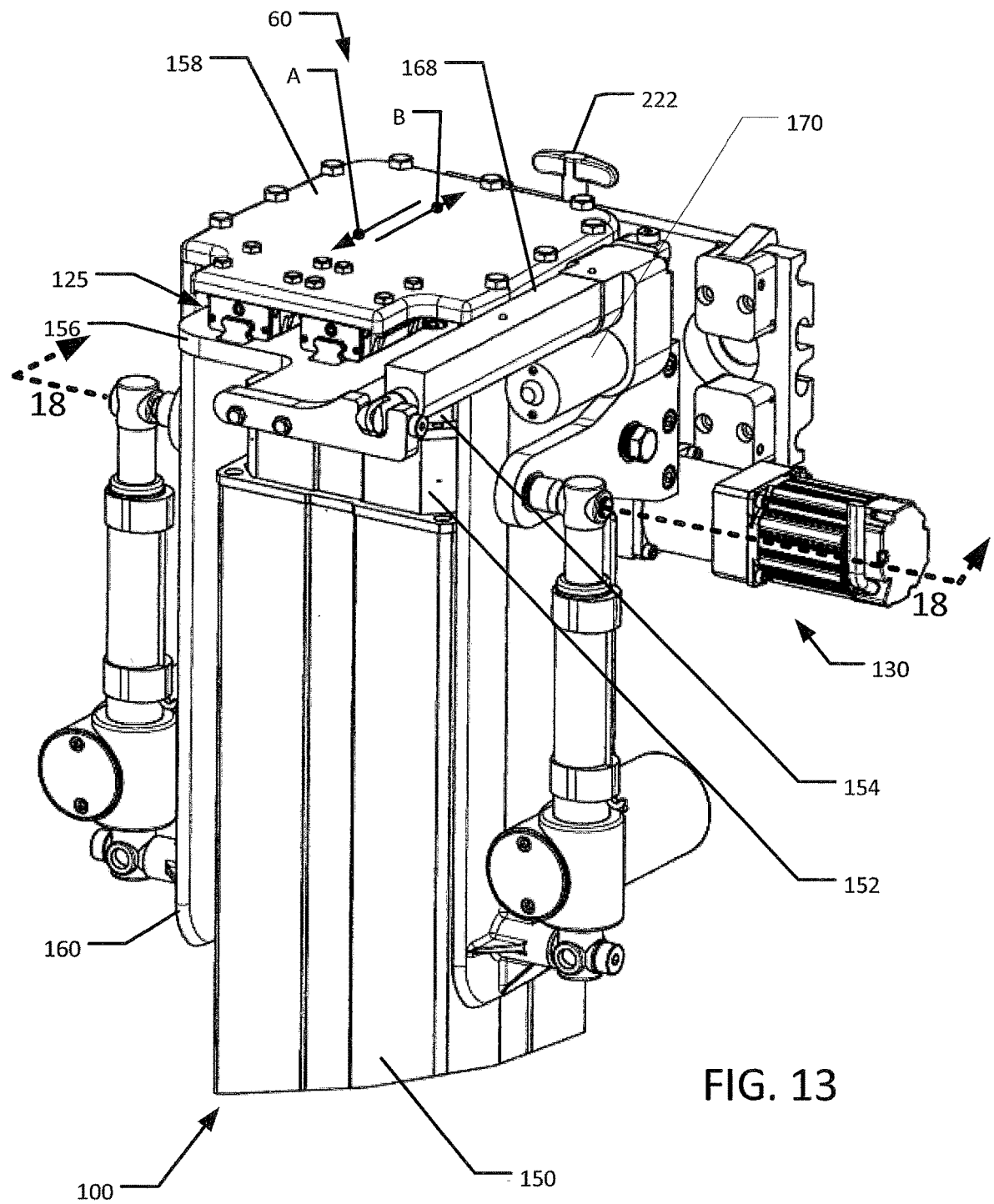
FIG. 13 is a left side isometric view of the upper rear region of the head end of FIG. 11.

FIGS. 11-13 are, respectively, a rear elevation view, a right side isometric view, and a left side isometric view of a rear region of the vertical support 100 of the head end 60 of the base 15. As can be understood from FIGS. 7 and 11-13, in one embodiment, the head end vertical support 100 includes a telescopic arrangement of an outer segment 150, an intermediate segment 152 within the outer segment 150, and an inner segment 154 within the intermediate segment 152. The bottom end of the outer segment 150 is fixedly connected to the wheel base 105, the intermediate segment 152 is vertically displaceable along the outer segment 150, and the inner segment 154 is vertically displaceable along the intermediate segment 152. A top end of the inner segment 154 is fixedly connected to a base plate 156 of the head end translation assembly 125, and the head end translation assembly 125 is fixedly connected to a top plate 158 of a mount 160 supporting the head end pitch/roll assembly 130. In other words, the head end translation assembly 125 is sandwiched between the top end of the head end vertical support 100 and the mount 160 supporting the head end pitch/roll assembly 130 thereby facilitating the front/rear displacement of the head end pitch/roll assembly 130 along the longitudinal axis of the base 15 relative to the head end vertical support 100, as described in greater detail below. Also, since the top end of the inner segment 154 is coupled to the head end pitch/roll assembly 130 via the sandwiched arrangement of the top plate 158, head end translation assembly 125 and mount 160, the head end pitch/roll assembly 130 is vertically displaceable via the head end vertical support 100 relative to the head end wheeled base 105.

The vertical displacement of the intermediate segment 152 and the inner segment 154 may be brought about by a variety of mechanical arrangements acting on the segments including, but not limited to, screw driven linear actuators, rack and pinion arrangements, hydraulic or pneumatic rams, etc. While the segments 150, 152, 154 are depicted as being telescopically arranged, the segments may have other configurations so long as the segments facilitate the head end vertical support 100 vertically adjusting so as to be adjustable in its overall height. In one embodiment, the head end vertical support 100 may be height adjustable up to approximately 37 inches in total adjustment. In one embodiment, the height adjustment may be infinitely adjustable such that the adjustments are not incremental. In other embodiments, the height adjustment may be incrementally adjustable such that the height adjustments are divided over a set number of increments. In some embodiments, the height adjustment may be selectively available as either infinitely adjustable or incrementally adjustable as a function of software operation and selections made by an operator of the table at the computer interface screen 145.

2. The Head End Translation Assembly

Figure 14:
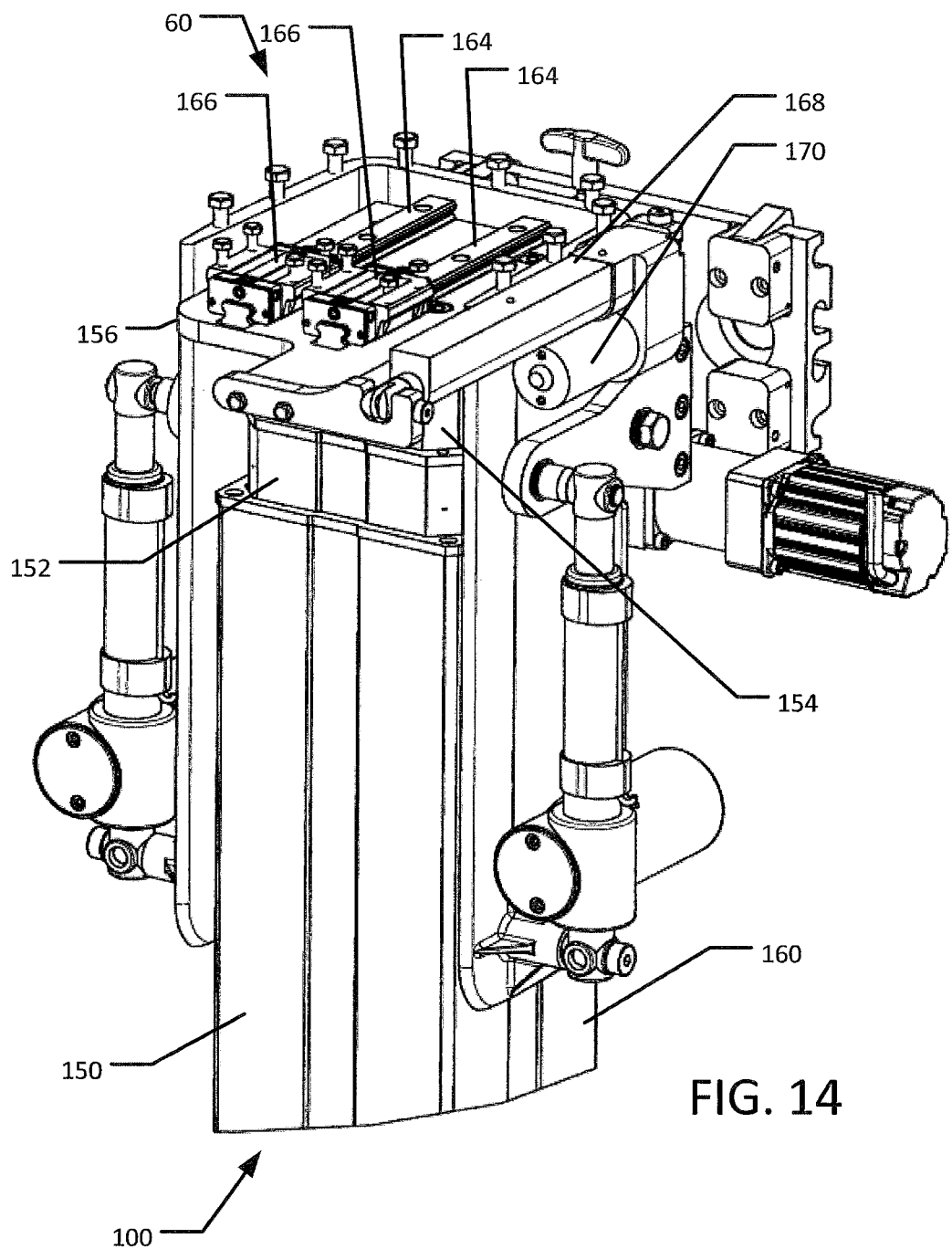
FIG. 14 is the same view as FIG. 13, except the top plate of the mount supporting the head end pitch/roll assembly has been hidden to more clearly depict components of the head end translation assembly.

As indicated in FIG. 14, which is the same view as FIG. 13, except with the top plate 158 of the mount 160 supporting the head end pitch/roll assembly 130 removed to more clearly depict components of the head end translation assembly 125, the assembly 125 includes the base plate 156, rails 164, slotted blocks 166, and a linear actuator 168. The rails 164 are fixedly connected to the base plate 156, which is fixedly connected to the top end of the inner segment 154 of the head end vertical support 100. The slotted blocks 166 are each coupled to a respective rail 164 in a sliding arrangement such that each slotted block 166 slides along its respective rail 164. The slotted blocks are also fixedly connected to the bottom surface of the top plate 158 of the mount 160 supporting the head end pitch/roll assembly 130. Thus, the sliding block/rail arrangement of the head end translation assembly 125 is sandwiched between the base plate 156 (which is fixedly connected to the top end of the head end vertical support 100) and the top plate 158 of the mount 160 supporting the head end pitch/roll assembly 130 thereby facilitating the front/rear displacement of the head end pitch/roll assembly 130 along the longitudinal axis of the base 15 relative to the head end vertical support 100. In one embodiment, this displacement is mechanized via a linear actuator 168 that driven by a motor 170 and acts between the base plate 156 of the head end translation assembly 125 and the mount 160 supporting the head end pitch/roll assembly 130.

The translation assemblies 125, 135 work together to compensate for the change in effective distance between the pitch/roll assemblies 130, 140 brought about by the rigid exterior frame 300 of the patient support 20 changing slope from a horizontal orientation between the opposed vertical supports 100 and a sloped orientation between the opposed vertical supports 100 and vice versa. Because the translation assemblies 125, 135 compensate for such movement of the exterior rigid frame, the opposed columns 100 can remain a fixed distance from each other while the rigid exterior frame 300 transitions between horizontal and varying degree of slope, and vice versa.

In other words, because the length of the rigid exterior frame 300 of the patient support 20 is fixed, when the exterior rigid frame is horizontal as shown in FIG. 3, the pitch/roll assemblies 130, 140 will be at their further distance apart, the slotted blocks 166 of the respective translation assemblies 125, 135 having displaced their greatest extent apart along their rails 164. Thus, the top plates 158 of the mounts 160 supporting the respective pitch/roll assemblies 130/140 will move away from each other (i.e., diverge) as indicated by arrows A in FIGS. 13 and 24.

Figure 44:
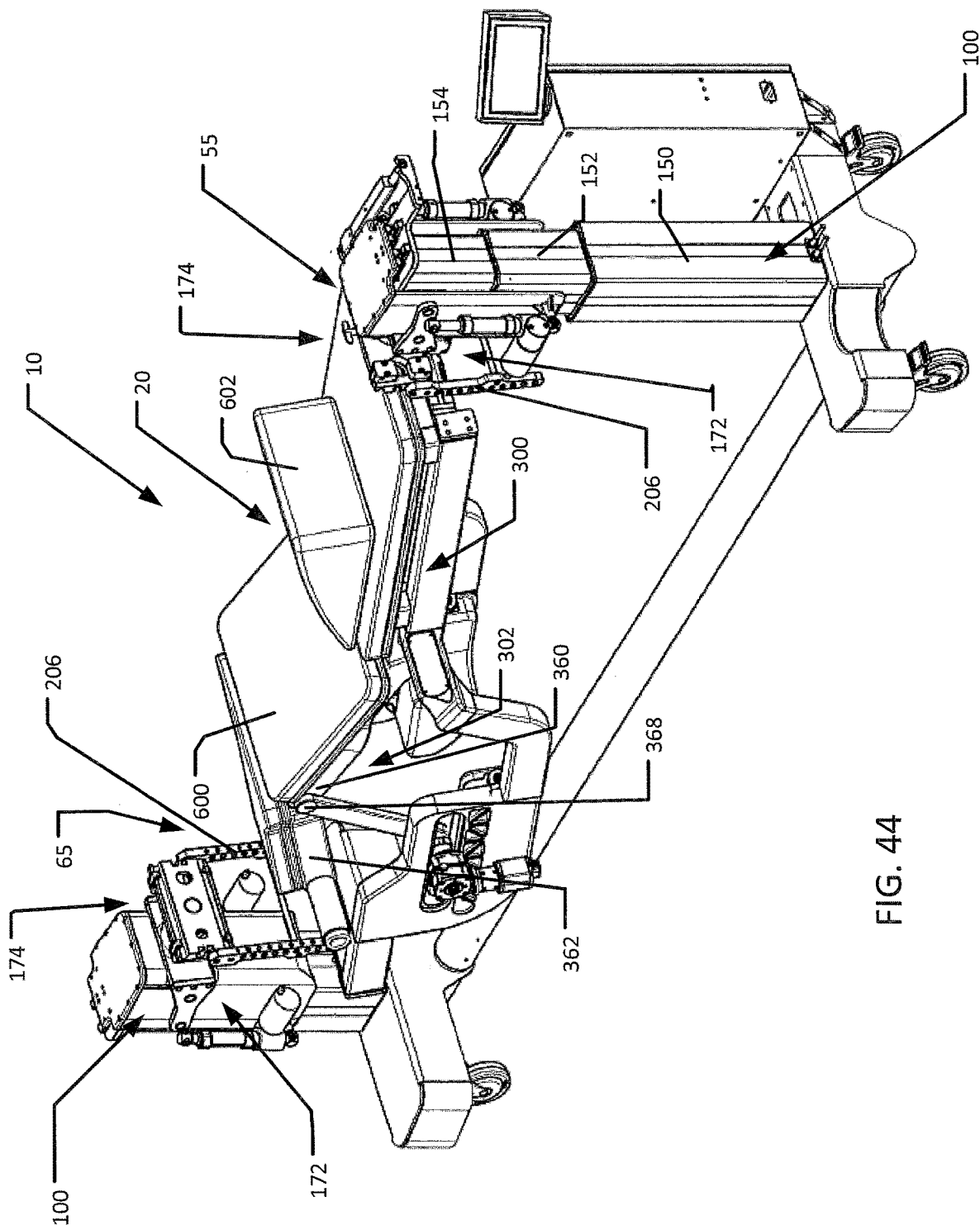
FIG. 44 is an isometric view from a right side and head end perspective of an embodiment of the surgical table with the patient support positioned with flat-top pads to position a patient in a seated position.
Figure 45:
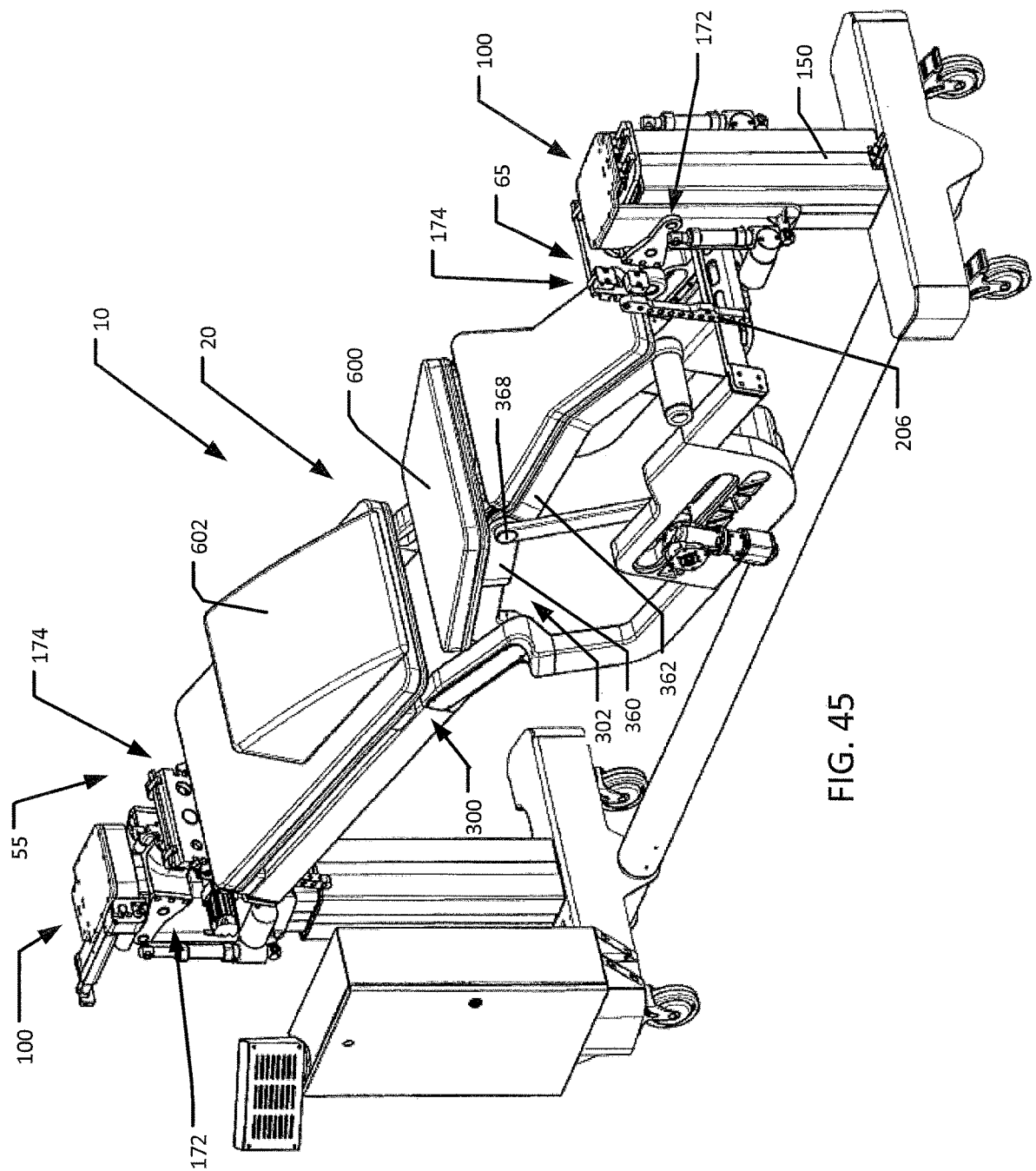
FIG. 45 is an isometric view from a left side and foot end perspective of the surgical table as shown in FIG. 44.
Figure 46:
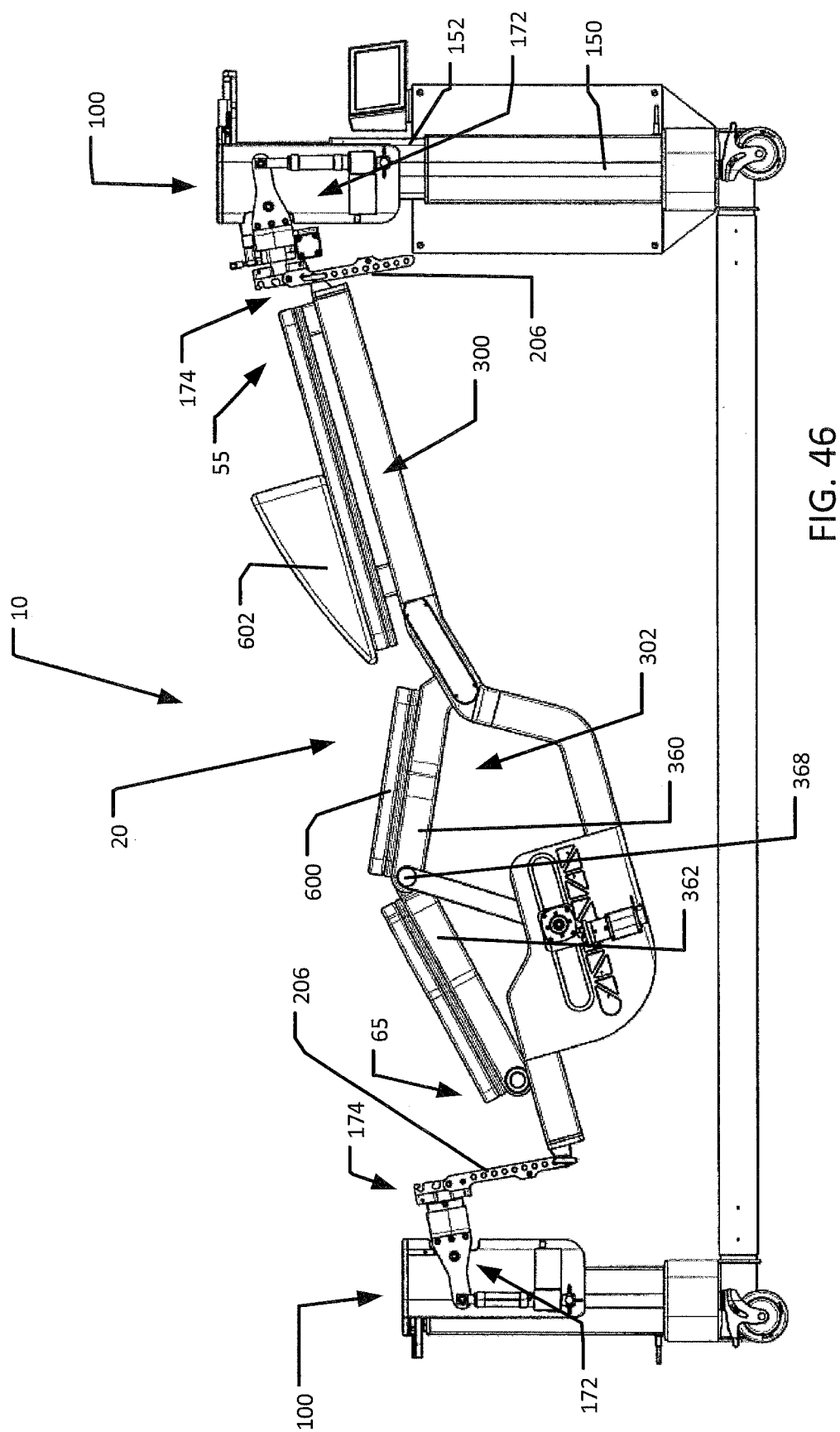
FIG. 46 is a right side view of the surgical table as shown in FIG. 44.

As the rigid exterior frame 300 of the patient support 20 transitions to an increasingly sloped orientation (e.g., as depicted in FIGS. 44-46), the distance between the pitch/roll assemblies 130, 140 will have to decrease as the sloped length of the exterior rigid frame is a hypotenuse of a triangle and the horizontal distance between the pitch/roll assemblies is a base of the triangle and, as a result, less than the hypotenuse. Thus, when the rigid exterior frame 300 of the patient support 20 is at its maximum slope, the pitch/roll assemblies 130, 140 will be at their smallest distance apart, the slotted blocks 166 of the respective translation assemblies 125, 135 having displaced towards each other to the greatest extent along their rails 164. Thus, the top plates 158 of the mounts 160 supporting the respective pitch/roll assemblies 130/140 will move towards each other (i.e., converge) as indicated by arrows B in FIGS. 13 and 24.

The head end translation assembly 125 is also present and configured to facilitate the surgical field being held stable during the various manipulations of the surgical field by the patient support 20 being displaced relative to the base 15 and/or the patient 12 being flexed, extended or placed neutral by the deflection of the patient support inner frame 302 relative to the patient support outer frame 300, as discussed below. The head end and foot end translation assemblies 125, 135 are coordinated in this function by software driving the servomotors of the translation assemblies 125, 135.

3. The Head End Pitch/Roll Assembly

Figure 15:
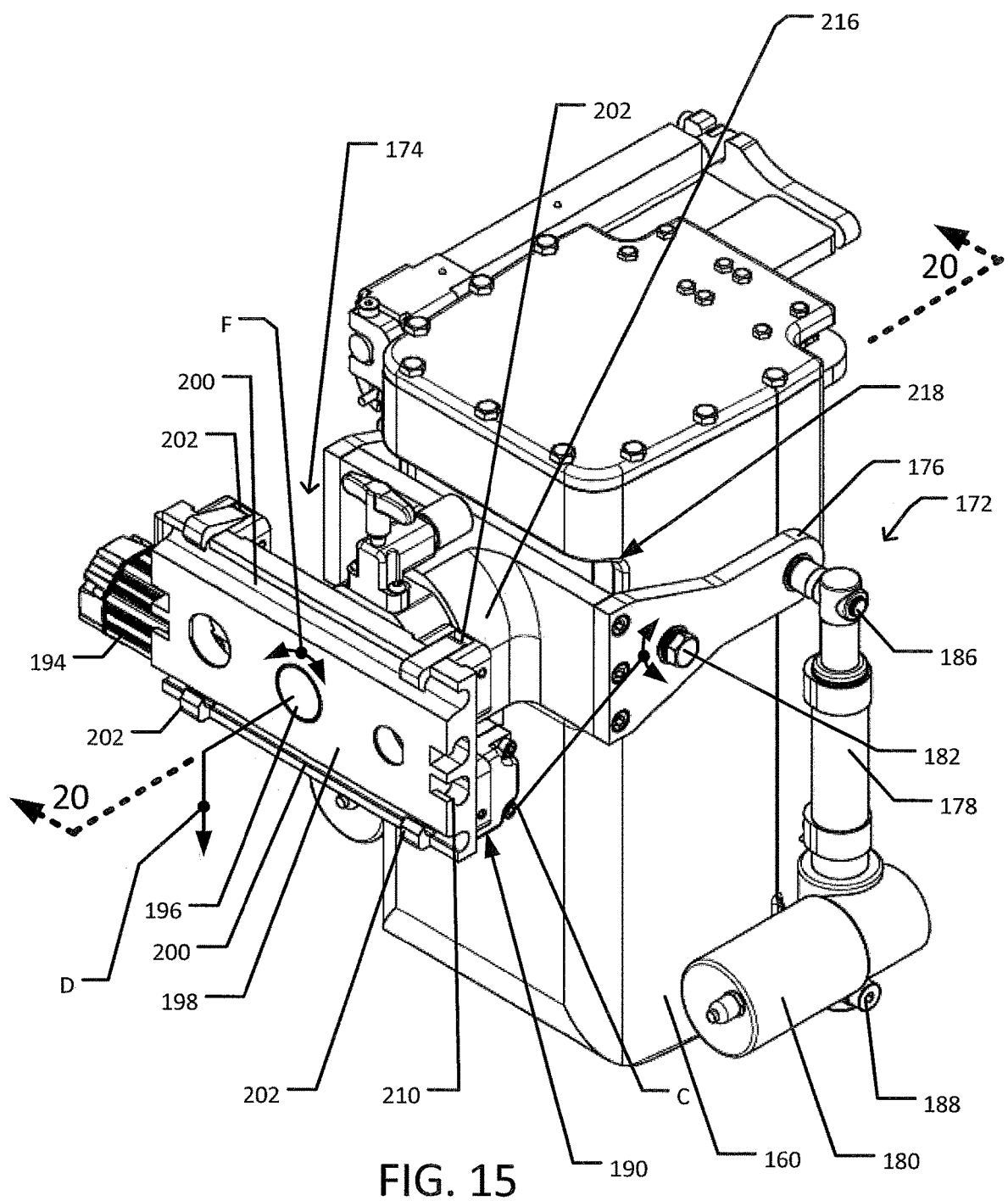
FIG. 15 is a right side isometric view of a front region of the head end pitch/roll assembly of the base of FIG. 1.
Figure 16:
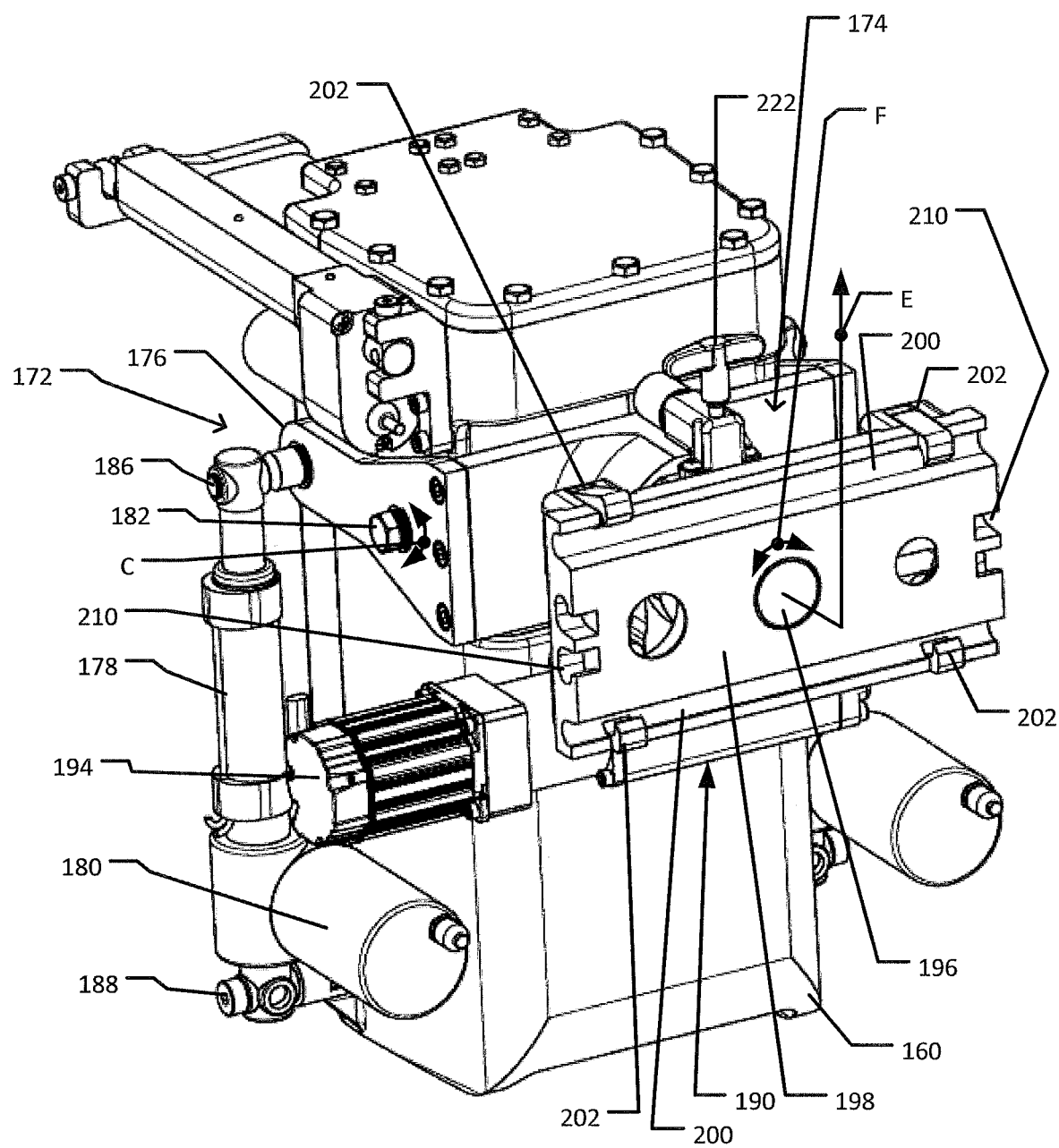
FIG. 16 is a left side isometric view of the front region of the head end pitch/roll assembly of FIG. 15.
Figure 17:
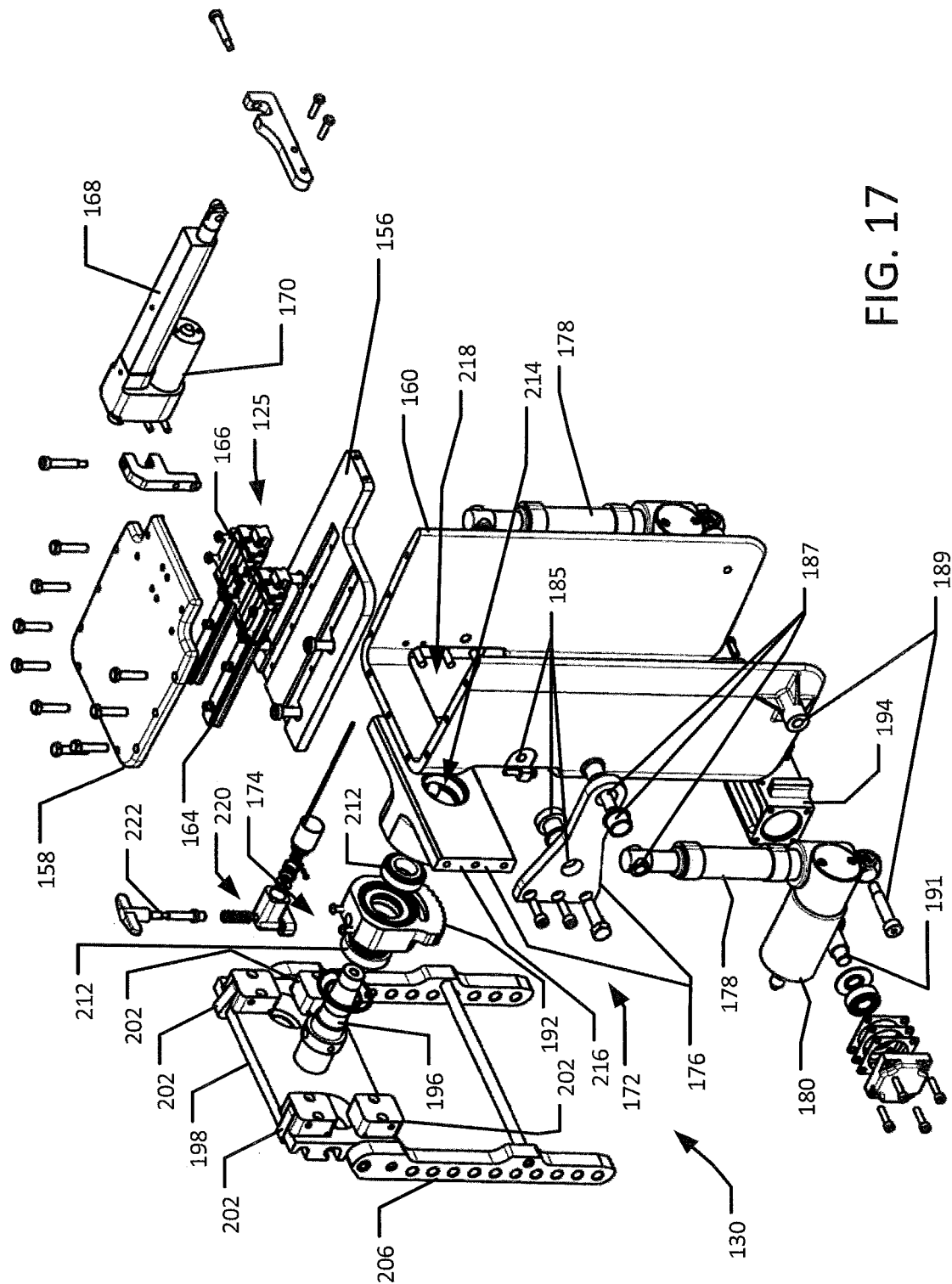
FIG. 17 is an exploded right side isometric view of the rear region of the head end pitch/roll assembly and the head end translation assembly.

To begin a detailed discussion of the head end pitch/roll assembly 130 of the base 15 of FIG. 1, reference is made to FIGS. 15-17. The head end pitch/roll assembly 130 may also be called a first connection assembly. FIGS. 15-16 are, respectively, right and left side isometric views of the front region of the head end pitch/roll assembly 130 of the base 15 of FIG. 1. FIG. 17 is an exploded right side isometric view of the rear region of the head end pitch/roll assembly 130 and the head end translation assembly 125. As can be understood from FIGS. 10 and 15-17, the head end pitch/roll assembly 130 includes a pitch assembly 172 pivotally connected to the mount 160 and a roll assembly 174 pivotally coupled to an arm or yoke 176 of the pitch assembly 172.

Figure 18:
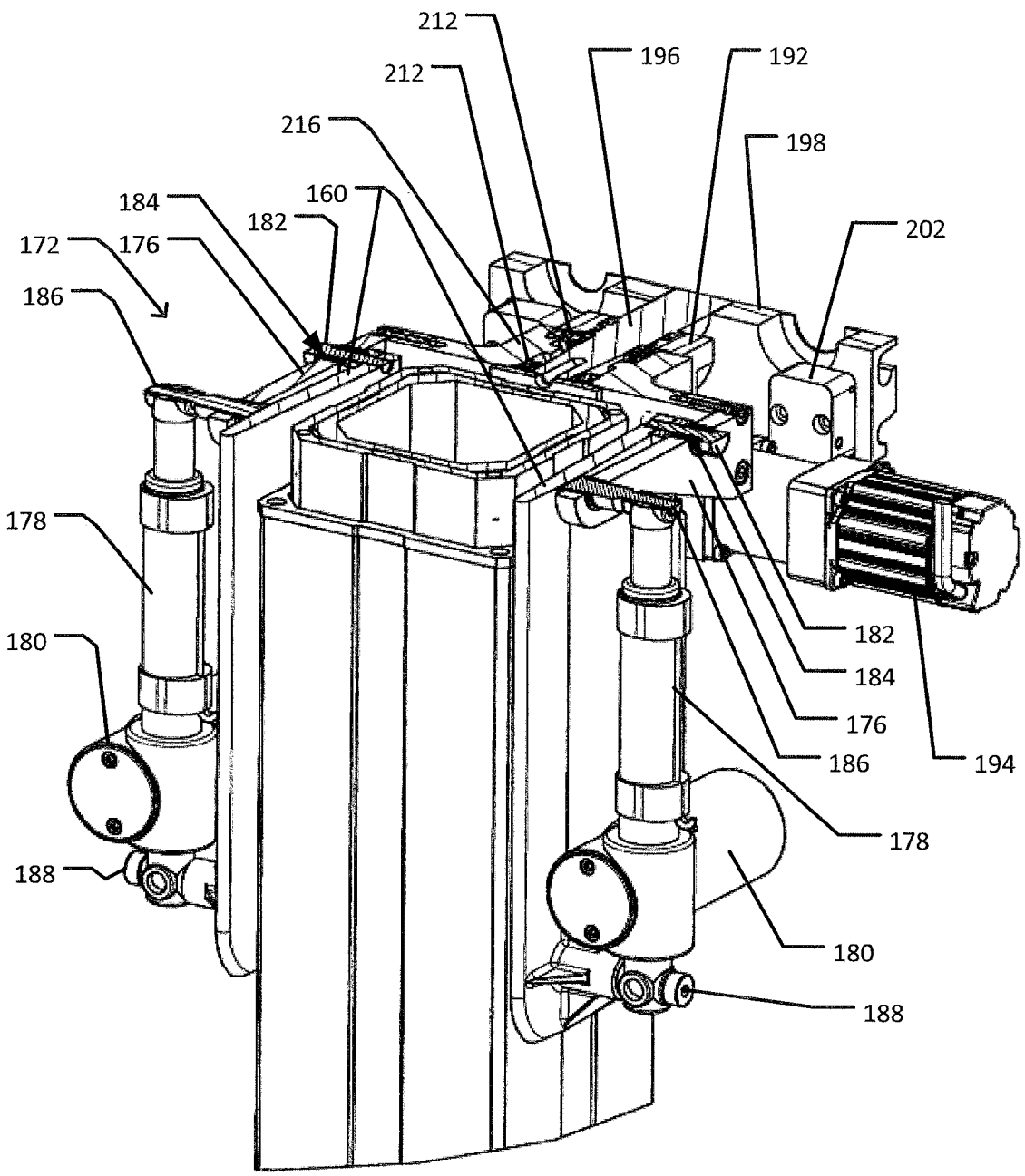
FIG. 18 is a horizontal cross section focusing on the pivot assembly as taken along section line 18-18 in FIG. 13.

The pitch assembly 172 includes the pitch arm 176 and a linear drive 178 having a motor 180. As indicated in FIG. 18, which is a horizontal cross section focused on the pitch assembly 172 as taken along section line 18-18 in FIG. 13, forward or fulcrum pins 182 extend from the right and left sides of the mount 160 to be pivotally received by pivot holes 184 in the right and left sides of the pitch arm 176 to combine together as fulcrums or pivots 185 (see FIG. 17) about which the pitch arm 176 pivots relative to the mount 160, as indicated by arrows C in FIGS. 15 and 16.

Rearward or lever arm pins 186 extend from the right and left sides of the pitch arm 176 rearward of the fulcrum pins 182 to be pivotally received by the upper ends of the linear drives 178, thereby forming lever points 187 (see FIG. 17) to act about the fulcrums 185. Bottom ends of the linear drives 178 are pinned via anchor pins 188 to a bottom region of each respective side of the mount 160, thereby forming anchor points 189 (see FIG. 17).

Thus, when the linear drives 178 act between their respective anchor pins 188 (or anchor points 189) and lever arm pins 186 (or lever points 187) such that the linear drive 178 extends, the pitch arm 176 is caused to pitch downward about the fulcrum pins 182 (or fulcrums 185), thereby driving the roll assembly 174 to pitch downward as indicated by arrow D in FIG. 15. Similarly, when the linear drives 178 act between their respective anchor pins 188 (or anchor points 189) and lever arm pins 186 (or lever points 187) such that the linear drive 178 retracts, the pitch arm 176 is caused to pitch upward about the fulcrum pins 182 (or fulcrums 185), thereby driving the roll assembly 174 to pitch upwardly as indicated by arrow E in FIG. 16.

As can be understood from FIGS. 10 and 15-17, the roll assembly 174 includes a worm drive 190 including a worm 191 and a worm gear 192, the worm drive being driven by a motor 194. The roll assembly 174 further includes an axel 196 that extends rearward from a center of a ladder attachment assembly 198. The ladder attachment assembly 198 includes upper and lower horizontal slots 200, each such slot including a pair of spaced-apart hooked attachment mechanisms 202 that retain a horizontal bar 204 of an H-frame 206 received in the respective slot 200, as can be understood from FIG. 10.

The H-frame 206 is used to suspend the head end 55 of the patient platform 20 from the head end 60 of the base 15, as can be understood from FIGS. 3 and 4. The H-frame 206 by the head end 60 may be referred to as a first frame member. The H-frame 206 by the foot end 70 may be referred to as a second frame member. More specifically, the H-frame 206 is used to link the head end 55 of the platform 20 to the ladder attachment assembly 198 of the roll assembly 174 of the head end 60 of the base 15. The upper of the two horizontal bars 204 of the H-frame 206 is received in the lower of the two horizontal slots 200 of the ladder attachment assembly 198 and fixedly retained therein by the corresponding spaced-apart hooked attachments mechanism 202 and the interaction of tabs 208 of the H-frame 206 received in corresponding notches 210 in the ladder attachment assembly 198, as can be understood from FIGS. 10 and 15-17. As discussed below, the head end 55 of the platform 20 is pivotally coupled to the lower of the two horizontal bars 204 of the H-frame 206 such that the head end 55 of the platform 20 can pivot about the lower of the two horizontal bars 204 of the H-frame 206 when the platform 20 transitions between different pitches.

An upper H-frame 206 (not shown in drawings) can be attached to the upper of the two horizontal slots 200 similar, but oppositely, as shown in the drawings for the lower H-frame 206. The presence of both an upper and lower H-frame 206 extending, respectively, upwardly and downwardly from the ladder attachment assembly 198 of each end 60, 70 of the frame 15 can be used to support an upper patient platform (not shown in drawings) and a lower patient platform 20 for to sandwich the patient 12 there between for different procedures, positions, and movements, including tilting or even rolling of the patient 12.

Figure 19:
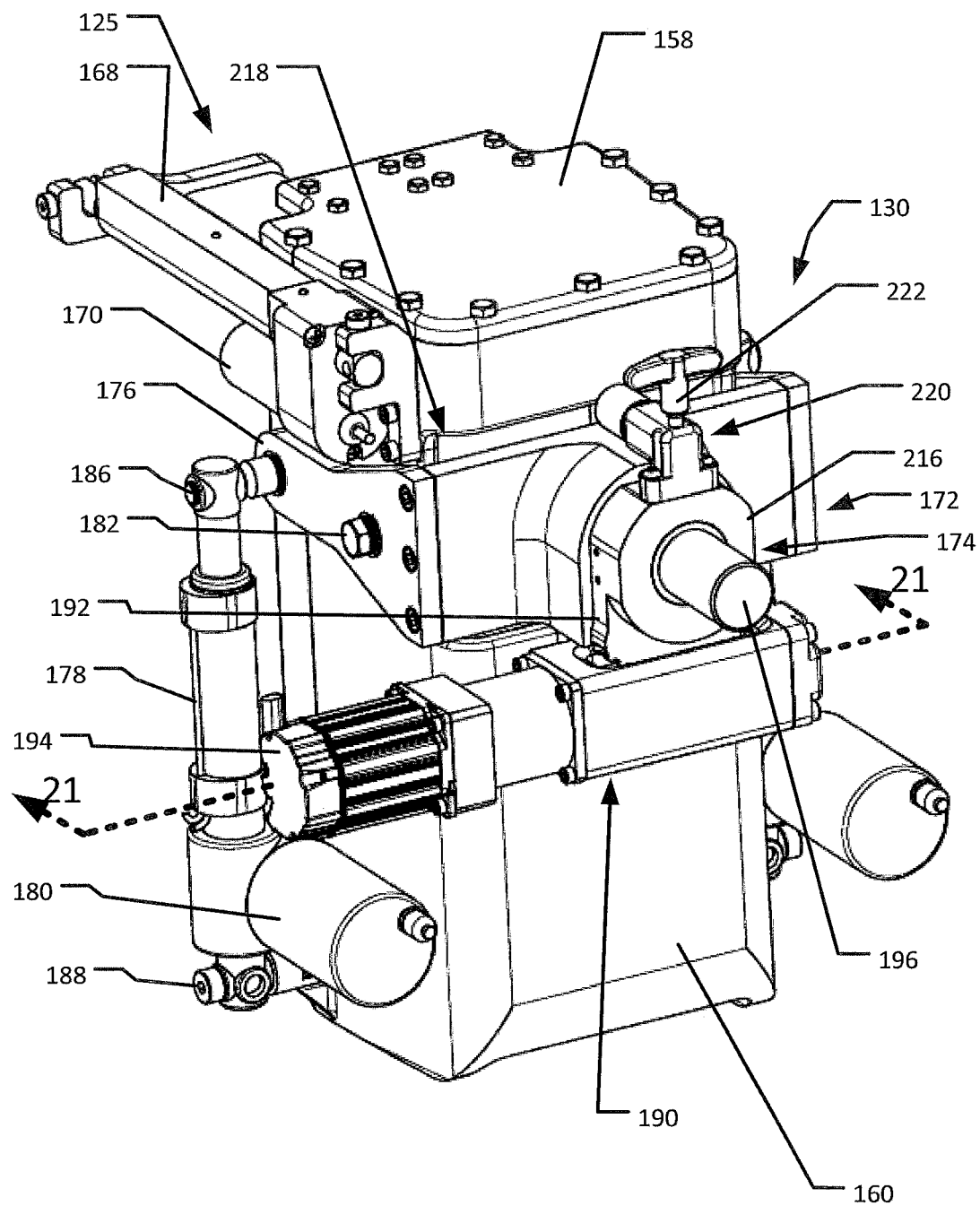
FIG. 19 is the same isometric view as FIG. 16, except the ladder attachment assembly has been removed from about the axel.
Figure 20:
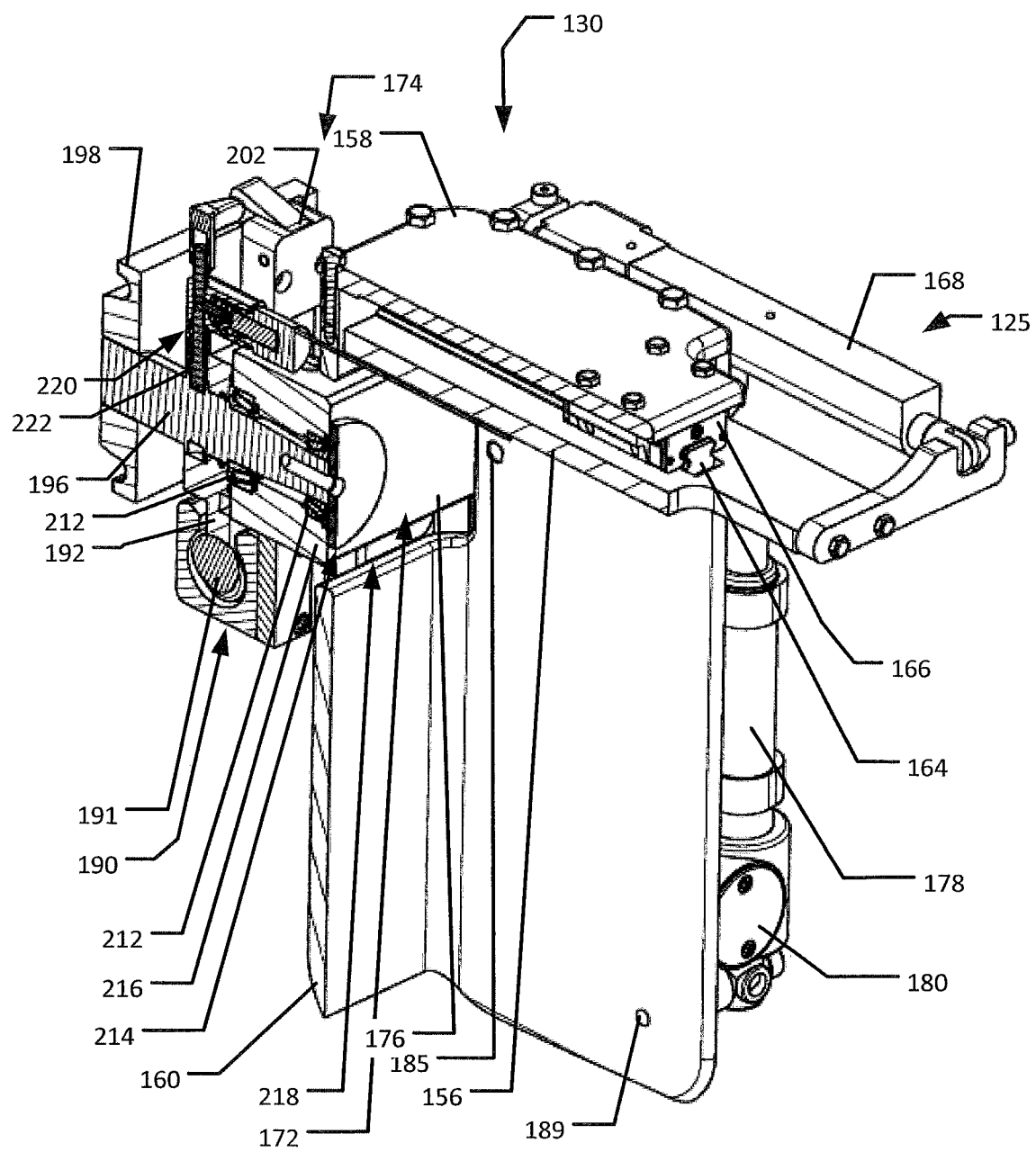
FIG. 20 is a cross sectional isometric elevation focusing on the roll assembly as taken along section line 20-20 in FIG. 15.

FIG. 19 is the same isometric view as FIG. 16, except the ladder attachment assembly 198 has been removed from about the axel 196. FIG. 20 is a cross sectional isometric elevation focused on the roll assembly 174 as taken along section line 20-20 in FIG. 15. As can be understood from FIGS. 10 and 17-20, the axel 196 extends rearward from a center of the ladder attachment assembly 198 such that a rearward half of the axel 196 is pivotally supported by front and rear bearing rings 212 in a cylindrical opening 214 of a front portion 216 of the pitch arm 176. Thus, the axel 196 is pivotally supported in, and relative to, the front portion 216 of the pitch arm 176. The ladder attachment assembly 198 is fixed to the front end of the axel 196 and, as a result, is pivotal relative to the front portion 216 of the pitch arm 176.

Figure 21:
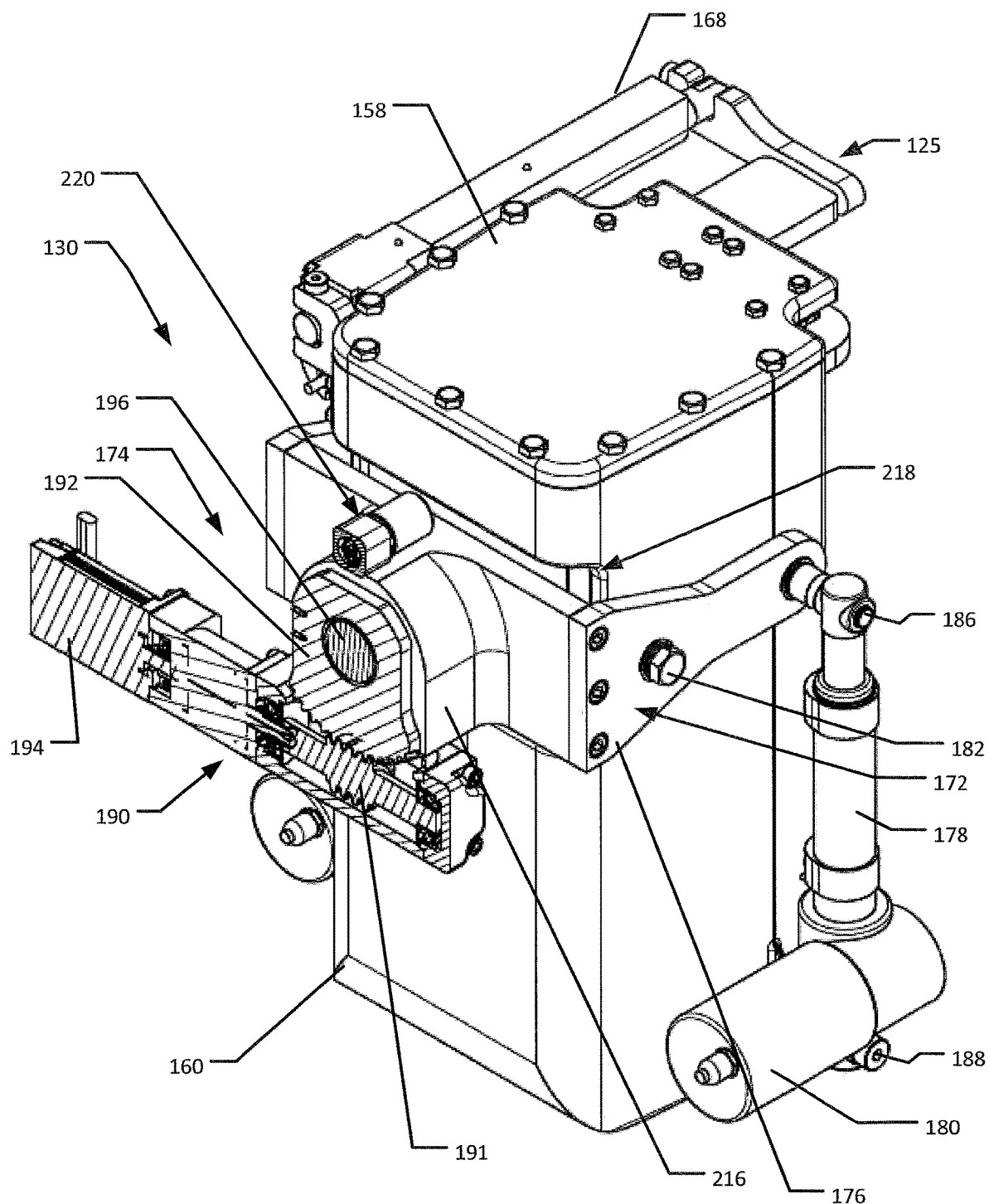
FIG. 21 is a cross sectional isometric elevation focusing on the worm drive assembly as taken along section line 21-21 in FIG. 19.

FIG. 21 is a cross sectional isometric elevation focused on the worm drive 190 as taken along section line 21-21 in FIG. 19. As can be understood from FIGS. 17-21, the worm gear 192 is fixed to and extends radially outward from the axel 196 to interface with the worm 191. Thus, the motor 194 of the worm drive 190 can drive the worm 191 in a first direction to cause the worm gear 192 and the axel 196 to displace in a first rotation to cause the ladder attachment assembly 198 and the patient platform 20 to pivot in a first roll direction. Similarly but oppositely the motor 194 of the worm drive 190 can drive the worm 191 in a second direction to cause the worm gear 192 and the axel 196 to displace in a second rotation to cause the ladder attachment assembly 198 and the patient platform 20 to pivot in a second roll direction. The resulting first and second roll directions can be understood from arrow F in FIGS. 15 and 16. Depending on the embodiment, the mechanical arrangement may allow for powered roll in either direction of approximately 25 degrees (plus or minus five degrees) for a total of 50 degrees (plus or minus 10 degrees) of roll range right to left.

As shown in FIGS. 15-21, a window 218 is defined in the upper front region of the mount 160 to facilitate pitch clearance for the front portion 216 of the pitch arm 176 as the pitch arm is cause to pitch up and down.

As can be understood from FIGS. 15-21, a roll lock assembly 220 including a lock pin 222 can be received in one of a series of holes about the circumference of the axel 196 to lock the axel 196 and, as a result, the patient support 20 in a desired roll orientation. Depending on the embodiment, the roll lock assembly 220 may be configured for automated or manual actuation of the lock pin 222. While the roll assembly is configured for a total roll range right-to-left of approximately 50 degrees via power applied via the motor 194, the lock pin 222 can be disengaged to allow the patient platform 20 to be rolled 180 degrees or even 360 degrees on the roll assemblies by surgical room staff physically and manually grasping the patient platform and rolling it relative to the base 15 to perform a sandwich and roll operation with the patient on the patient platform. Once the sandwich and roll operation is complete, the lock pin 222 can be re-engaged with the roll assembly to allow the roll assembly to be power driven again by the motor 194. Depending on the embodiment, the lock pin 222 may be located at only one of the ends of the base or at both ends of the base.

b. The Foot End of the Base

Figure 22:
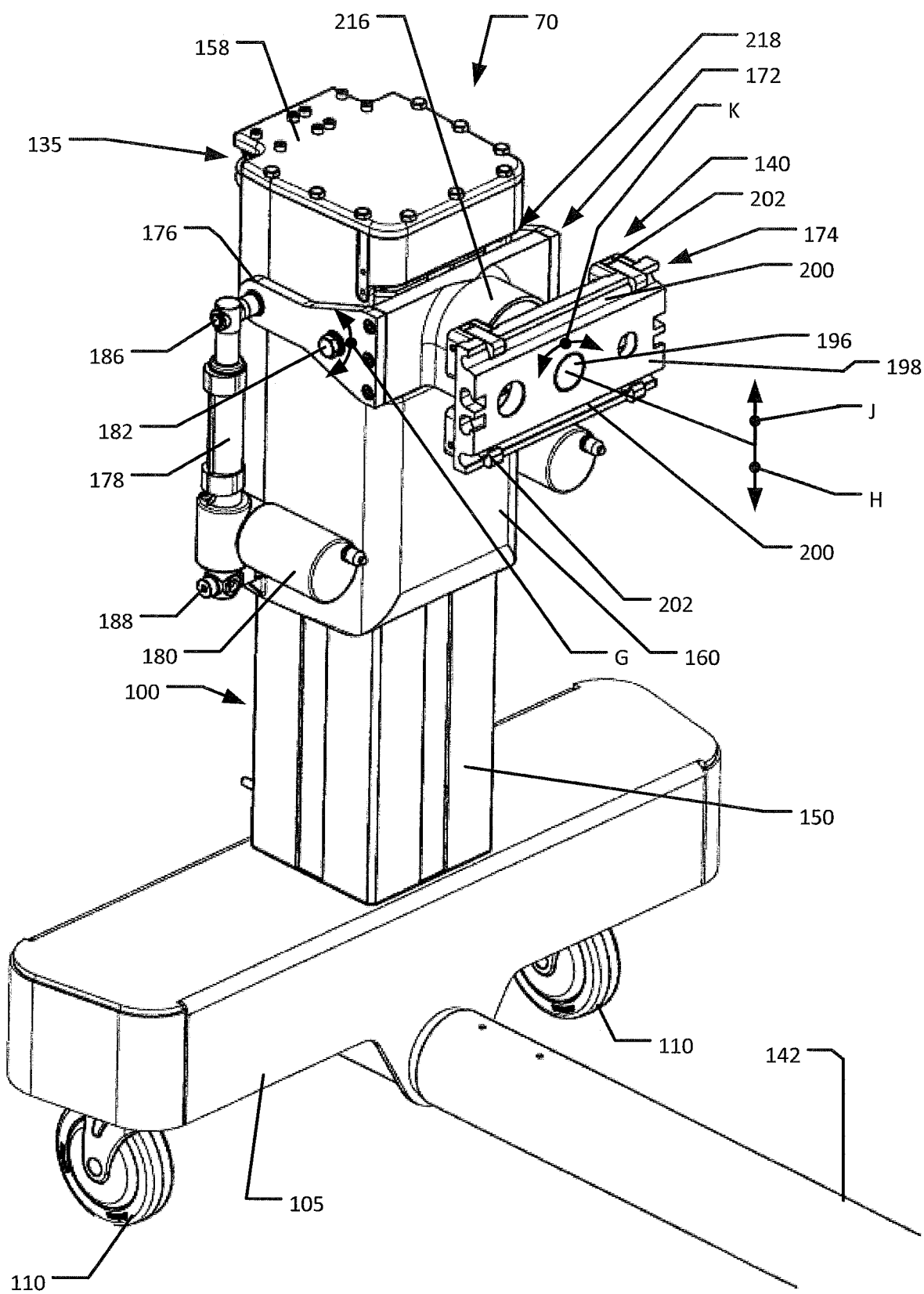
FIG. 22 is a right side isometric view of a front region of the foot end of the base 15 of FIG. 1.
Figure 23:
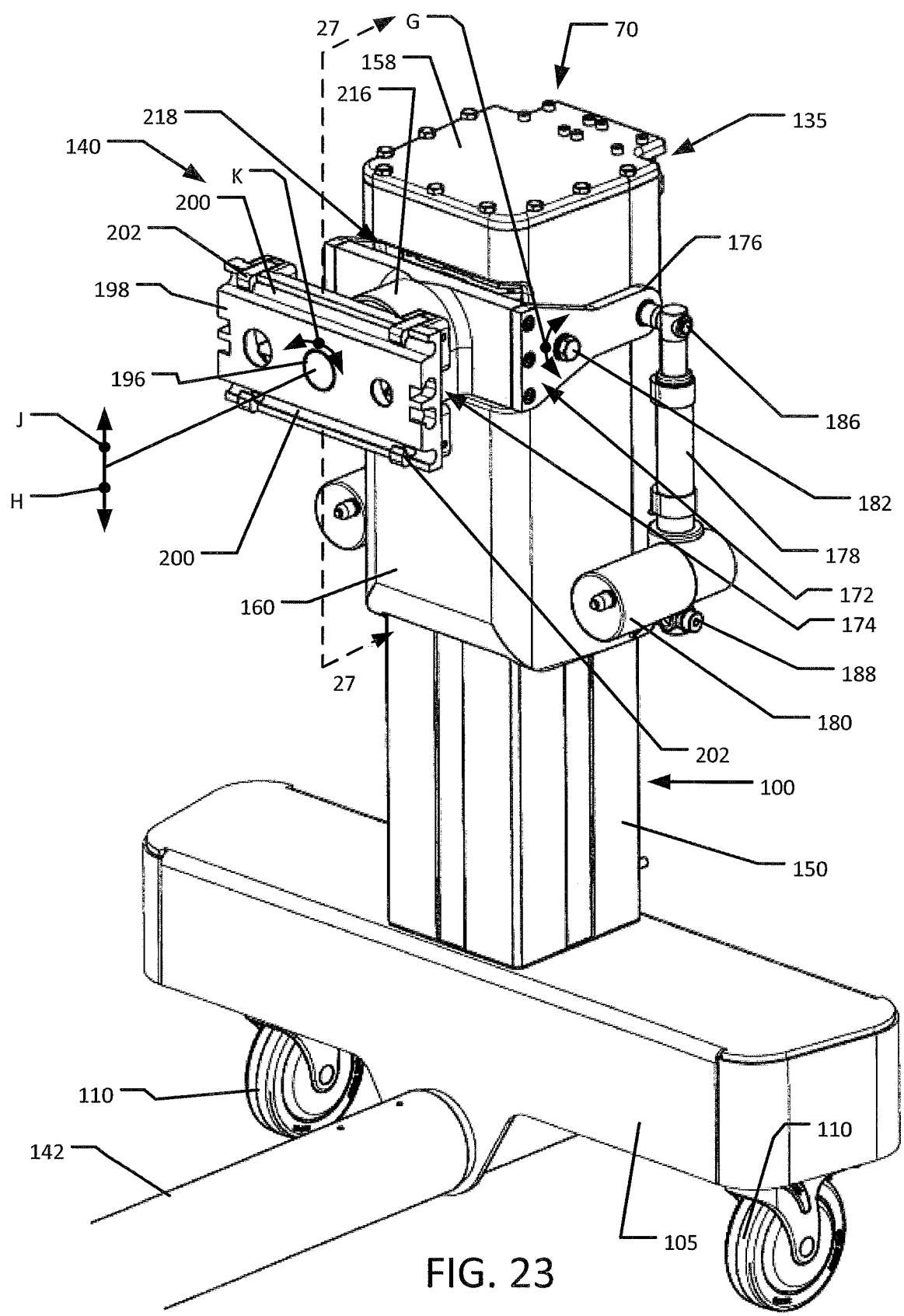
FIG. 23 is a left side isometric view of a front region of the foot end of FIG. 22.

To begin the detailed discussion of the foot end 70 of the base 15, reference is made to FIGS. 22-23, wherein FIGS. 22-23 are, respectively, a right side isometric view and a left side isometric view of a front region of the foot end 70 of the base 15 of FIG. 1. The designations of the foot end 70 having front and rear regions have no meaning other than for purposes of facilitating the discussion herein.

As mentioned above and further shown in FIGS. 22-23, the base foot end 70 includes the vertical support 100, the wheeled base 105 with castors 110, the foot end translation assembly 135, and the foot end pitch/roll assembly 140. The foot end vertical support 100 of the base 15 extends vertically upward from the wheeled base 105 and is generally centered right-to-left on the wheeled base 105 and centered right-to-left relative to the base frame member 142. The foot end translation assembly 135 and the foot end pitch/roll assembly 140 are found near the top of the foot end vertical support 100.

1. The Foot End Vertical Support

Figure 24:
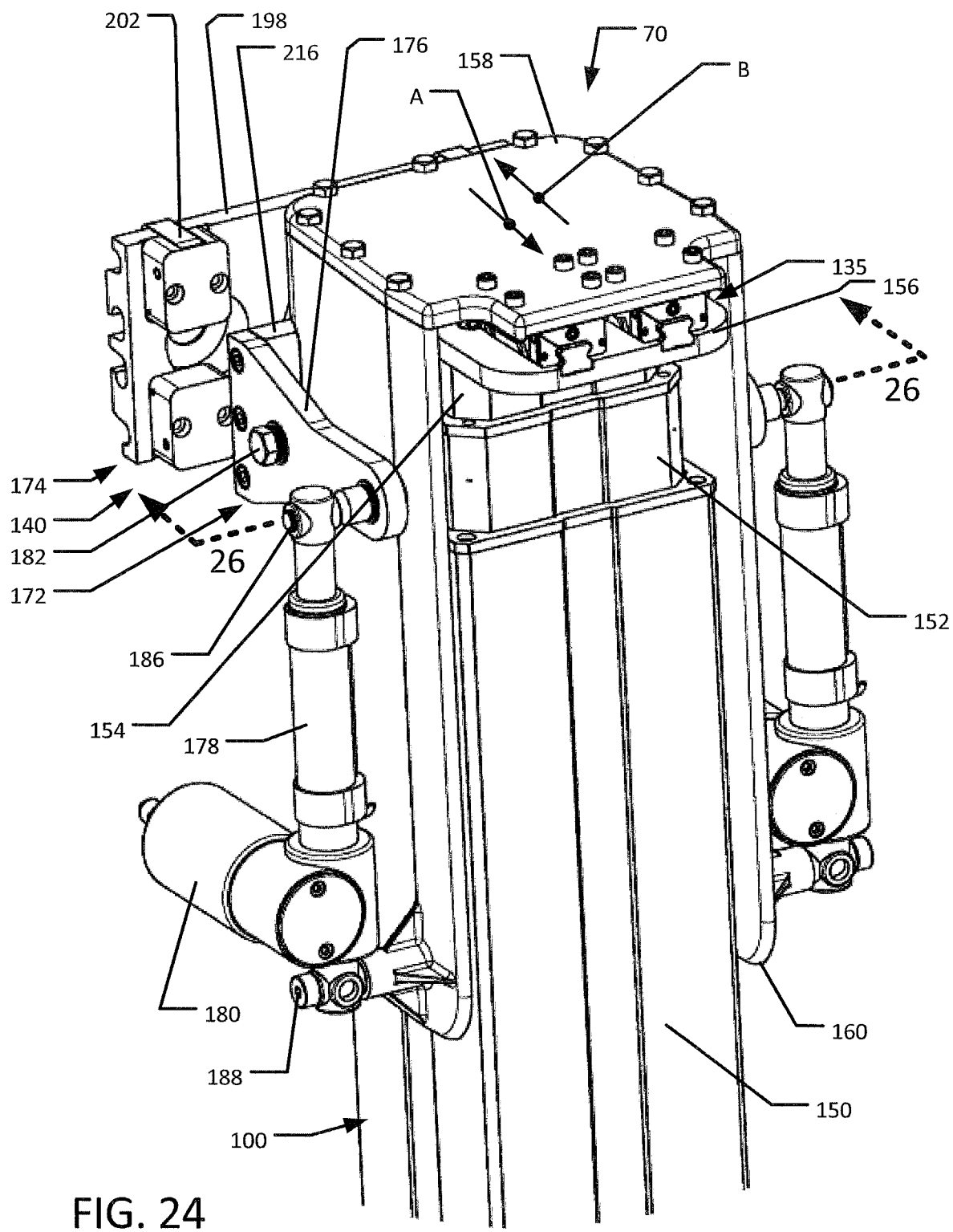
FIG. 24 is a left side isometric view of a rear region of the vertical support of the foot end of the base.

FIG. 24 is a left side isometric view of a rear region of the vertical support 100 of the foot end 70 of the base 15. As can be understood from FIGS. 22-24, the vertical support 100 of the foot end 70 is substantially similar to the vertical support 100 of the head end 60 discussed above with respect to FIGS. 7 and 11-13.

As can be understood from FIGS. 22-24, in one embodiment, the foot end vertical support 100 includes a telescopic arrangement of an outer segment 150, an intermediate segment 152 within the outer segment 150, and an inner segment 154 within the intermediate segment 152. The bottom end of the outer segment 150 is fixedly connected to the wheel base 105, the intermediate segment 152 is vertically displaceable along the outer segment 150, and the inner segment 154 is vertically displaceable along the intermediate segment 152. A top end of the inner segment 154 is fixedly connected to a base plate 156 of the foot end translation assembly 135, and the foot end translation assembly 135 is fixedly connected to a top plate 158 of a mount 160 supporting the foot end pitch/roll assembly 140. In other words, the foot end translation assembly 135 is sandwiched between the top end of the foot end vertical support 100 and the mount 160 supporting the foot end pitch/roll assembly 140 thereby facilitating the front/rear displacement of the foot end pitch/roll assembly 140 along the longitudinal axis of the base 15 relative to the foot end vertical support 100, as described in greater detail below. Also, since the top end of the inner segment 154 is coupled to the foot end pitch/roll assembly 140 via the sandwiched arrangement of the top plate 158, foot end translation assembly 135 and mount 160, the foot end pitch/roll assembly 140 is vertically displaceable via the foot end vertical support 100 relative to the foot end wheeled base 105.

The vertical displacement of the intermediate segment 152 and the inner segment 154 may be brought about by a variety of mechanical arrangements acting on the segments including, but not limited to, screw driven linear actuators, rack and pinion arrangements, hydraulic or pneumatic rams, etc. While the segments 150, 152, 154 are depicted as being telescopically arranged, the segments may have other configurations so long as the segments facilitate the foot end vertical support 100 vertically adjusting so as to be adjustable in its overall height. In one embodiment, the foot end vertical support 100 may be height adjustable up to approximately 37 inches in total adjustment. In one embodiment, the height adjustment may be infinitely adjustable such that the adjustments are not incremental. In other embodiments, the height adjustment may be incrementally adjustable such that the height adjustments are divided over a set number of increments. In some embodiments, the height adjustment may be selectively available as either infinitely adjustable or incrementally adjustable as a function of software operation and selections made by an operator of the table at the computer interface screen 145.

2. The Foot End Translation Assembly

Figure 25:
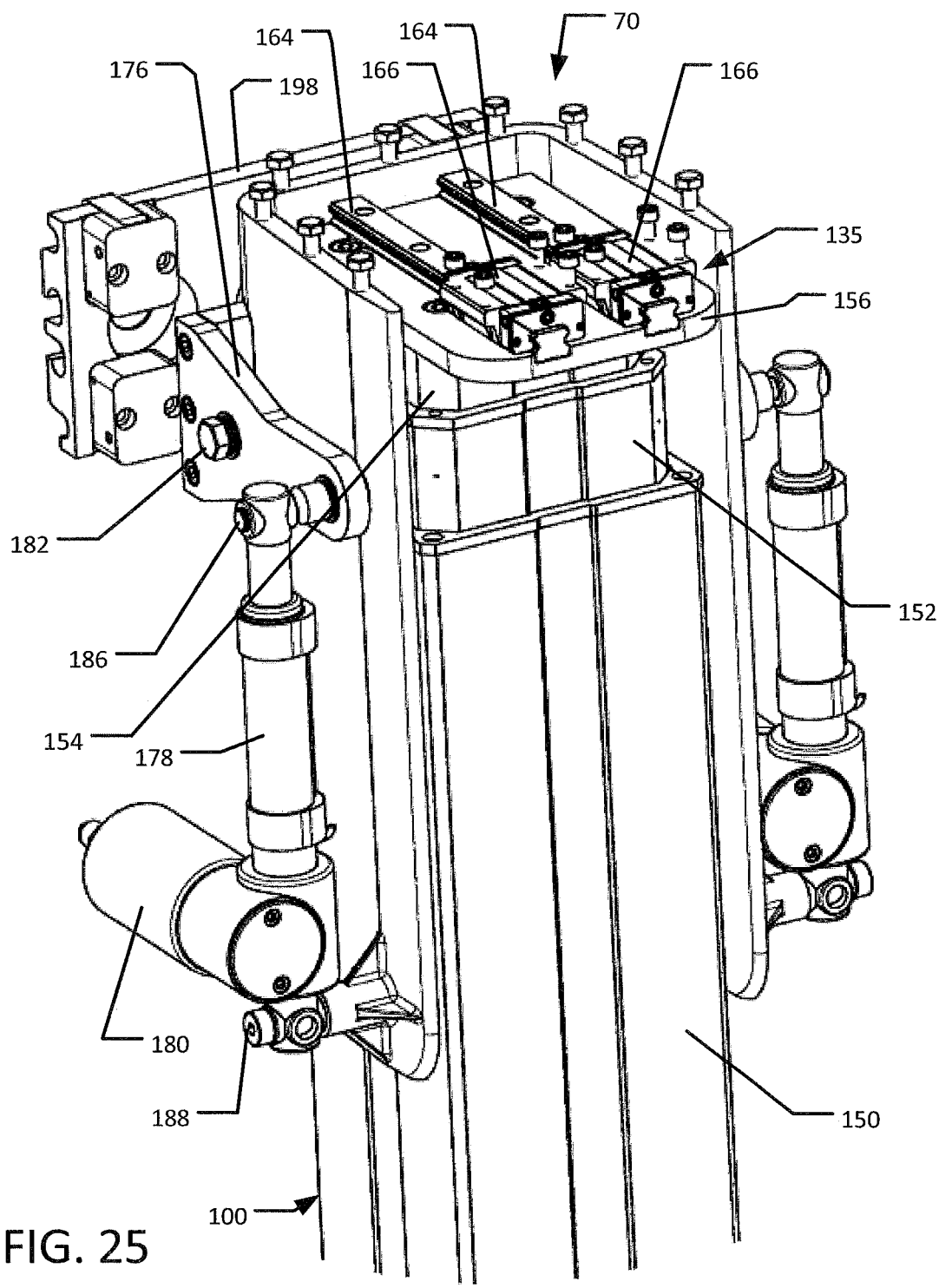
FIG. 25 is the same view as FIG. 24, except with the top plate of the mount supporting the foot end pitch/roll assembly removed to more clearly depict components of the foot end translation assembly.

FIG. 25 is the same view as FIG. 24, except with the top plate 158 of the mount 160 supporting the foot end pitch/roll assembly 140 removed to more clearly depict components of the foot end translation assembly 135. As can be understood from FIGS. 24-25, the foot end translation assembly 135 is similar to that of the head end translation assembly 125 discussed above with respect to FIGS. 13-14, except the embodiment of the foot end translation assembly shown in FIGS. 24-25 may be passive in that it is not directly actuated by a linear actuator but instead relies on forces transmitted through the patient platform 20 from the linear actuator 168 of the head end translation assembly 125 or by the displacement of the patient platform 20 itself to bring about displacement in the foot end translation assembly 135. In other embodiments, the foot end translation assembly 135 may be generally identical to that of the head end translation assembly 125 such that the foot end translation assembly 125 is actively displaced via its own linear translator.

As indicated in FIGS. 24-25, the passive version of the foot end translation assembly 135 includes the base plate 156, rails 164, and slotted blocks 166. The rails 164 are fixedly connected to the base plate 156, which is fixedly connected to the top end of the inner segment 154 of the foot end vertical support 100. The slotted blocks 166 are each coupled to a respective rail 164 in a sliding arrangement such that each slotted block 166 slides along its respective rail 164. The slotted blocks are also fixedly connected to the bottom surface of the top plate 158 of the mount 160 supporting the foot end pitch/roll assembly 140. Thus, the sliding block/rail arrangement of the foot end translation assembly 135 is sandwiched between the base plate 156 (which is fixedly connected to the top end of the foot end vertical support 100) and the top plate 158 of the mount 160 supporting the foot end pitch/roll assembly 140 thereby facilitating the front/rear displacement of the foot end pitch/roll assembly 140 along the longitudinal axis of the base 15 relative to the foot end vertical support 100.

As stated above, the translation assemblies 125, 135 work together to compensate for the change in effective distance between the pitch/roll assemblies 130, 140 brought about by the rigid exterior frame 300 of the patient support 20 changing slope from a horizontal orientation between the opposed vertical supports 100 and a sloped orientation between the opposed vertical supports 100 and vice versa. Because the translation assemblies 125, 135 compensate for such movement of the rigid exterior frame 300, the opposed columns 100 can remain a fixed distance from each other while the exterior rigid frame transitions between horizontal and varying degree of slope, and vice versa.

In other words, because the length of the rigid exterior frame 300 of the patient support 20 is fixed, when the exterior rigid frame is horizontal as shown in FIG. 3, the pitch/roll assemblies 130, 140 will be at their further distance apart, the slotted blocks 166 of the respective translation assemblies 125, 135 having displaced their greatest extent apart along their rails 164. Thus, the top plates 158 of the mounts 160 supporting the respective pitch/roll assemblies 130, 140 will move away from each other (i.e., diverge) as indicated by arrows A in FIGS. 13 and 24.

As the rigid exterior frame 300 of the patient support 20 transitions to an increasingly sloped orientation (e.g., as depicted in FIG. FIGS. 44-46), the distance between the pitch/roll assemblies 130, 140 will have to decrease as the sloped length of the exterior rigid frame is a hypotenuse of a triangle and the horizontal distance between the pitch/roll assemblies is a base of the triangle and, as a result, less than the hypotenuse. Thus, when the rigid exterior frame 300 of the patient support 20 is at its maximum slope, the pitch/roll assemblies 130, 140 will be at their smallest distance apart, the slotted blocks 166 of the respective translation assemblies 125, 135 having displaced towards each other to the greatest extent along their rails 164. Thus, the top plates 158 of the mounts 160 supporting the respective pitch/roll assemblies 130, 140 will move towards each other (i.e., converge) as indicated by arrows B in FIGS. 13 and 24.

The foot end translation assembly 135 is also present and configured to facilitate the surgical field being held stable during the various manipulations of the surgical field by the patient support 20 being displaced relative to the base 15 and/or the patient 12 being flexed, extended or placed neutral by the deflection of the patient support inner frame 302 relative to the patient support outer frame 300, as discussed below. The head end and foot end translation assemblies 125, 135 are coordinated in this function by software driving the servomotors of the translation assemblies 125, 135.

3. The Foot End Pitch/Roll Assembly

Figure 26:
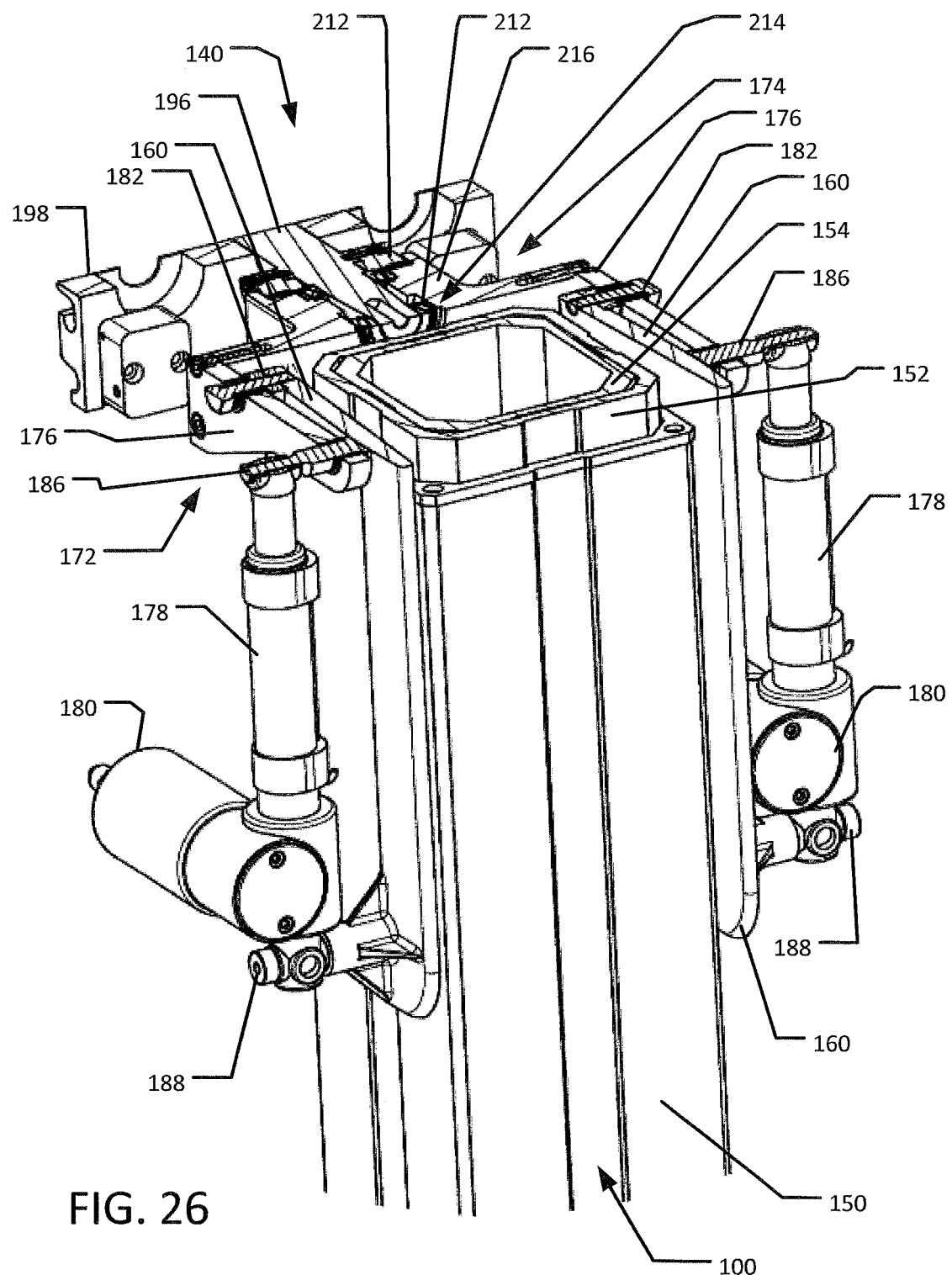
FIG. 26 is a horizontal cross section focused on the pitch assembly as taken along section line 26-26 in FIG. 24.
Figure 27:
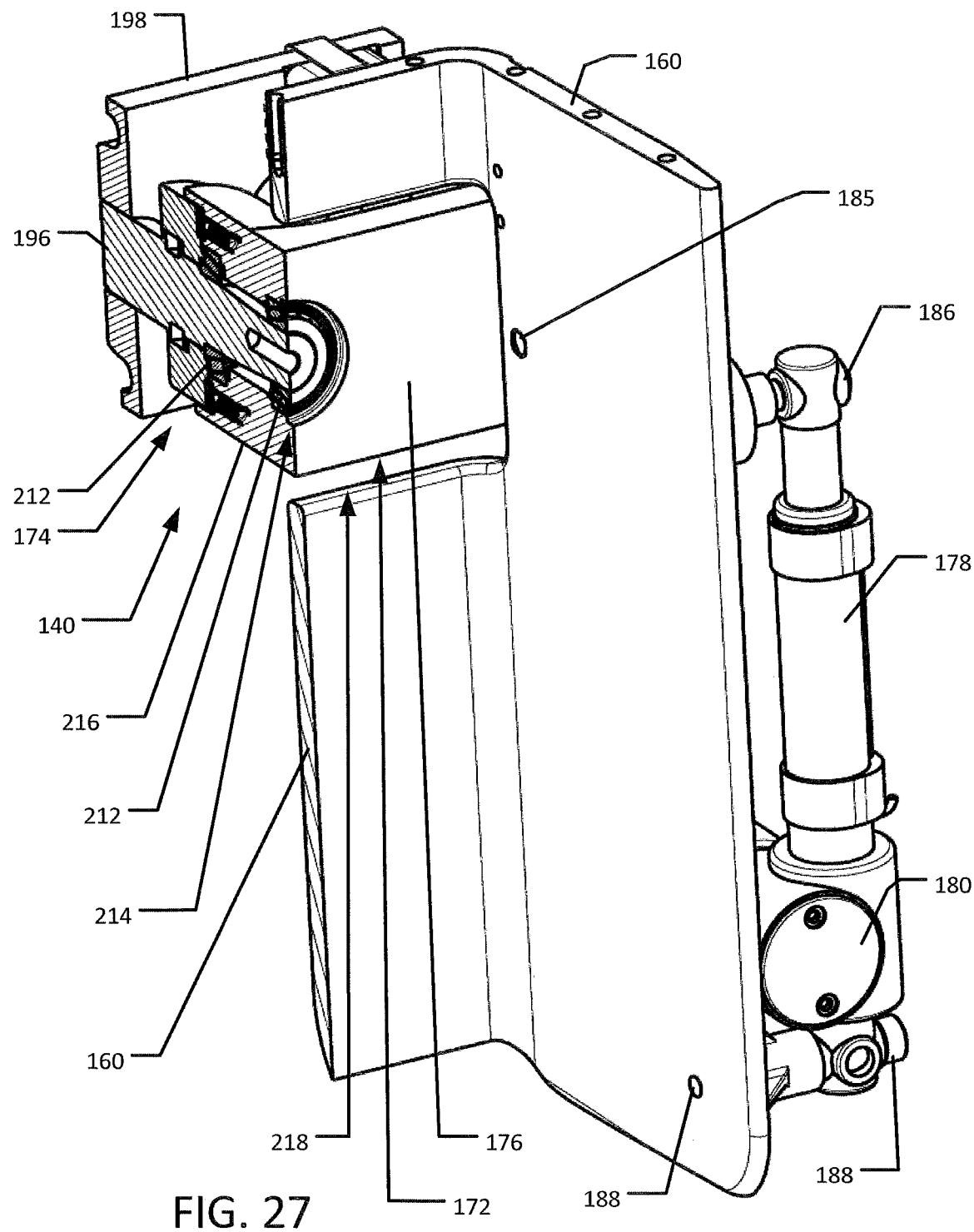
FIG. 27 is a cross sectional isometric elevation focused on the roll assembly as taken along section line 27-27 in FIG. 23.

To begin a detailed discussion of the foot end pitch/roll assembly 140 of the base 15 of FIG. 1, reference is made to FIGS. 22-24 and 26-27. The foot end pitch/roll assembly 140 may also be called a second connection assembly. FIG. 26 is a horizontal cross section focused on the pitch assembly 172 as taken along section line 26-26 in FIG. 24. FIG. 27 is a cross sectional isometric elevation focused on the roll assembly 174 as taken along section line 27-27 in FIG. 23.

As can be understood from FIGS. 22-24 and 26-27, the foot end pitch/roll assembly 140 is similar to that of the head end pitch/roll assembly 130 discussed above with respect to FIGS. 10 and 15-21, except the embodiment of the roll assembly 174 of the foot end pitch/roll assembly 140 shown in FIGS. 22-24 and 26-27 may be passive in that it is not directly actuated by a motor driven worm drive but instead relies on forces transmitted through the patient platform 20 from the motor driven worm drive 190 of the roll assembly 174 of the head end pitch/roll assembly 130 to bring about displacement in the roll assembly 174 of the foot end pitch/roll assembly 140. In other embodiments, the roll assembly 174 of the foot end pitch/roll assembly 140 may be generally identical to that of the roll assembly 174 of the head end pitch/roll assembly 130 such that the roll assembly 174 of the foot end pitch/roll assembly 140 is actively displaced via its own motor driven worm drive or other active drive mechanism.

As can be understood from FIGS. 22-24 and 26-27, the foot end pitch/roll assembly 140 includes a pitch assembly 172 pivotally connected to the mount 160 and a roll assembly 174 pivotally coupled to an arm or yoke 176 of the pitch assembly 172. The pitch assembly 172 includes the pitch arm 176 and a linear drive 178 having a motor 180. Forward or fulcrum pins 182 extend from the right and left sides of the mount 160 to be pivotally received by pivot holes 185 in the right and left sides of the pitch arm 176 to combine together as fulcrums or pivots about which the pitch arm 176 pivots relative to the mount 160, as indicated by arrows G in FIGS. 22 and 23.

As seen in FIGS. 3, 38A-38B, 46, 49, and 52, among others, the pitch assemblies 172 on the head end and foot ends function to maintain a substantially parallel alignment of the H-frames 206, or the first and the second frame members, and the ladder attachment assemblies 198 with each other during pitching or angling of the patient support 20 about an axis transverse to a longitudinal axis of the patient support 20. Additionally, the pitch assemblies 172 are configured to actively maintain the roll assemblies 174 in a coaxial alignment with each other during angling or pitching of the patient support 20 (more particularly, the outer frame 300) relative to the vertical supports 100. Thus, during pitching or angling of the outer frame 300 of the patient support 20 relative to the vertical supports 100, the axels 196 of the roll assemblies 174 are coaxial aligned such that the roll axis extends through the axels 196 of the roll assemblies 174. The roll assemblies 174 and, thus, the roll axes A, B as shown in FIG. 7, remain coaxially aligned because the pitch assemblies 172 or, more particularly, the linear drives 178 act between their respective anchor pins 188 and lever arm pins 186 to cause the roll assemblies 174 to angle or pitch upward or downward in response to the actuation of the linear drives 178.

This type of powered pitching or angling of the roll assemblies 174 at the support columns 100 such that the roll axes A, B remain coaxially aligned substantially reduces or eliminates binding of the various connections between the patient support 20 and the support columns 100. Without maintaining coaxial alignment of the roll axes, a full roll (i.e., 360 degrees) may not be possible. Conventional tables may align the roll axes when the patient support 20 is in a neutral position (i.e., parallel to the floor). But, often a patient must be in a non-neutral position (e.g., Trendelenburg, reverse Trendelenburg) and partially rolled. Thus, there is a need for a surgical table that can roll the patient support in non-neutral positions while actively maintaining the roll axes in coaxial alignment.

The coaxial alignment of the roll assemblies 174 is maintained by the pitch assemblies 172 when, for example, the head end 55 of the patient support 20 is at a different vertical elevation than the foot end 65 of the patient support 65, via the vertical supports 100 of the head and foot end being extended different vertical heights. In this example orientation of the patient support 20, among others, the pitch assemblies 172 are actuated to position the ladder attachment assemblies 198 generally parallel to each other and the roll assemblies 174 in-line such that a longitudinal axis of the axels 196 are coaxial.

Rearward or lever arm pins 186 extend from the right and left sides of the pitch arm 176 rearward of the fulcrum pins 182 to be pivotally received by the upper ends of the linear drives 178, thereby forming lever points to act about the fulcrums. Bottom ends of the linear drives 178 are pinned via anchor pins 188 to a bottom region of each respective side of the mount 160, thereby forming anchor points.

Thus, when the linear drives 178 act between their respective anchor pins 188 and lever arm pins 186 such that the linear drive 178 extends, the pitch arm 176 is caused to pitch downward about the fulcrum pins 182, thereby driving the roll assembly 174 to pitch downward as indicated by arrow H in FIG. 22. Similarly, when the linear drives 178 act between their respective anchor pins 188 and lever arm pins 186 such that the linear drive 178 retracts, the pitch arm 176 is caused to pitch upward about the fulcrum pins 182, thereby driving the roll assembly 174 to pitch upwardly as indicated by arrow J in FIG. 22.

As can be understood from FIGS. 22-24 and 26-27, the roll assembly 174 includes an axel 196 that extends rearward from a center of a ladder attachment assembly 198. The ladder attachment assembly 198 includes upper and lower horizontal slots 200, each such slot including a pair of spaced-apart hooked attachment mechanisms 202 that retain a horizontal bar 204 of an H-frame 206, or the second frame member, received in the respective slot 200, as was discussed above with respect to FIG. 10. The H-frame 206 of the foot end 70 is identically configured and used with the foot end ladder attachment assembly 198 as discussed above in the discussion of the head end pitch/roll assembly in Subsection I(b)(3) of this Detailed Description of the Preferred Embodiments.

As can be understood from FIGS. 22-24 and 26-27, the axel 196 extends rearward from a center of the ladder attachment assembly 198 such that a rearward half of the axel 196 is pivotally supported by front and rear bearing rings 212 in a cylindrical opening 214 of a front portion 216 of the pitch arm 176. Thus, the axel 196 is pivotally supported in, and relative to, the front portion 216 of the pitch arm 176. The ladder attachment assembly 198 is fixed to the front end of the axel 196 and, as a result, is pivotal relative to the front portion 216 of the pitch arm 176.

As already mentioned, actuation of the worm drive 190 of the roll assembly 174 of the head end pitch/roll assembly 130 causes the patient platform 20 to roll or displace about the axes A, B shown in FIG. 7, thereby causing the axel 196 of the roll assembly 174 of the foot end pitch/roll assembly 140 to pivot relative to the front portion 216 of the pitch arm 176 of the foot end pitch/roll assembly 140. The resulting first and second roll directions can be understood from arrow K in FIG. 22.

As shown in FIGS. 22-24 and 26-27, a window 218 is defined in the upper front region of the mount 160 to facilitate pitch clearance for the front portion 216 of the pitch arm 176 as the pitch arm is cause to pitch up and down.

While the above-described base 15 is advantageous when used with the below-described patient platform 20, it should be noted that embodiments of the above-described base could be employed with other patient platforms of the applicants' development with little or no modifications to either the base or the patient platforms. Similarly, while the below-described patient platform 20 is advantageous when used with the above-described base 15, it should be noted that embodiments of the below-described patient platform could be employed with other bases of the applicants' development with little or no modifications to either the patient platform or bases. Accordingly, the disclosures of Applicants' prior US provisional and nonprovisional applications are incorporated into this present disclosure in their entireties.

II. The Patient Platform

To begin the detailed discussion of the patient support 20, reference is made to FIGS. 1-4 where it can be understood that the patient support 20 is supported above the floor surface 25 by the base 15. More specifically, as can be understood from FIGS. 1-4, 10 and 17, the head end 55 of the patient support 20 is pivotally coupled to a bottom horizontal bar 204 of the H-frame 206 extending from the ladder attachment assembly 198 of the head end 60 of the base 15. Similarly, the foot end 65 of the patient support 20 is pivotally coupled to a bottom horizontal bar 204 of the H-frame 206 extending from the ladder attachment assembly 198 of the foot end 70 of the base 15. The patient support 20 includes an outer frame 300 and an inner frame 302, which in addition to being capable of articulating relative to itself, is supported off of and displaceable relative to the outer frame 300.

Figure 28:
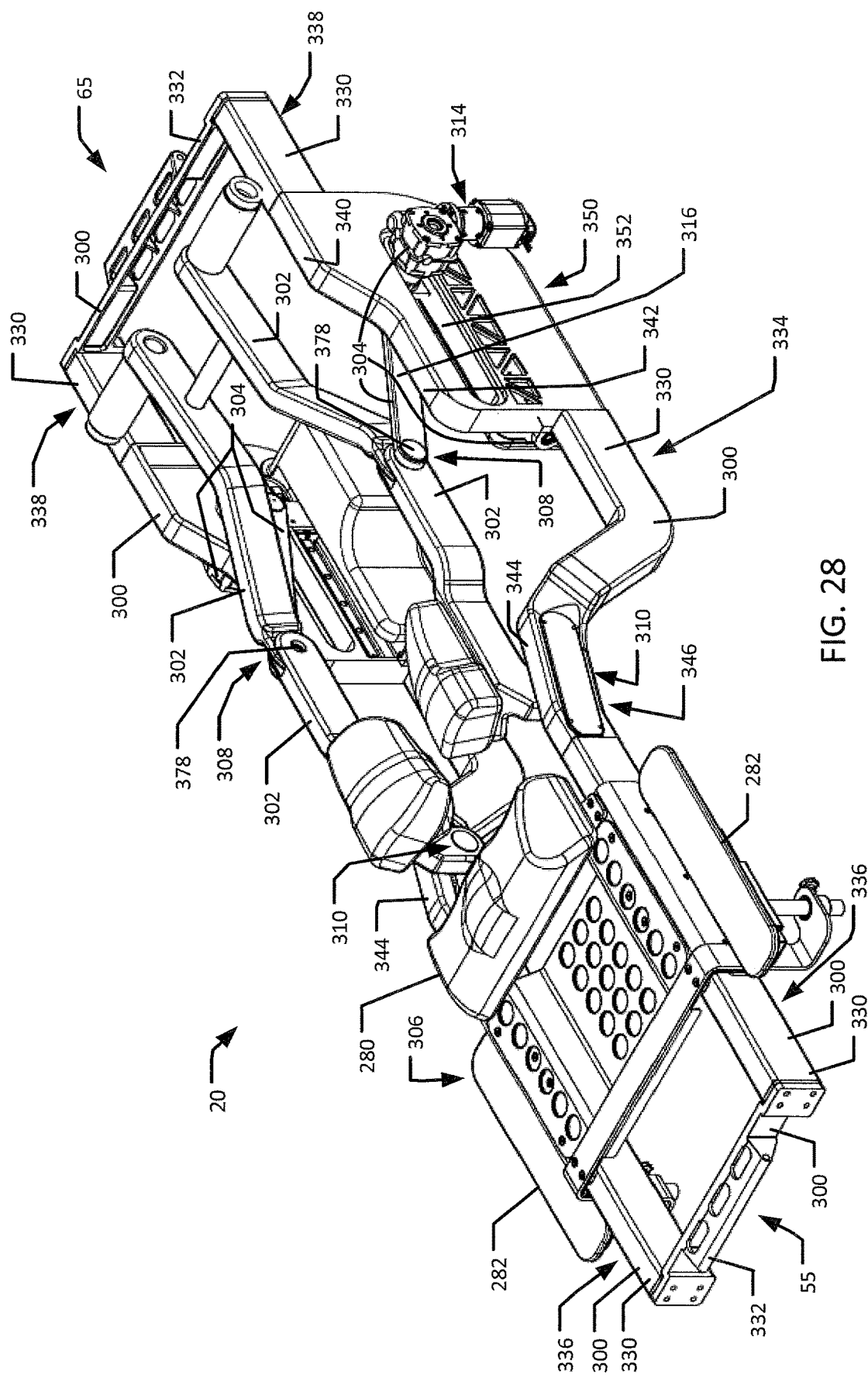
FIG. 28 is an isometric view from a left side and head end perspective of a patient support of the table of FIGS. 1-4, wherein the inner frame is in a neutral position relative to the outer frame.
Figure 29:
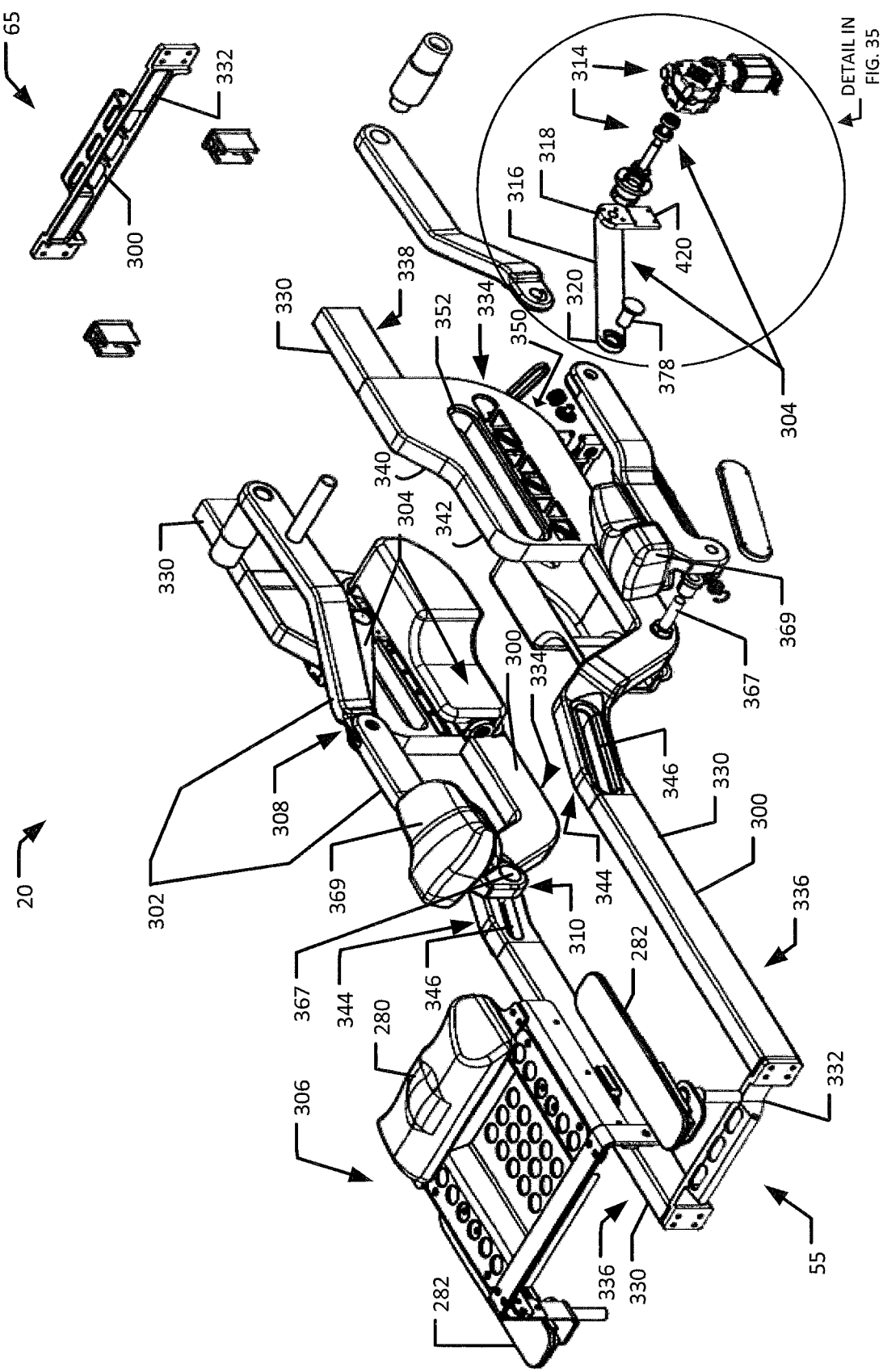
FIG. 29 is the same view of the patient support depicted in FIG. 28, except shown exploded.
Figure 30:
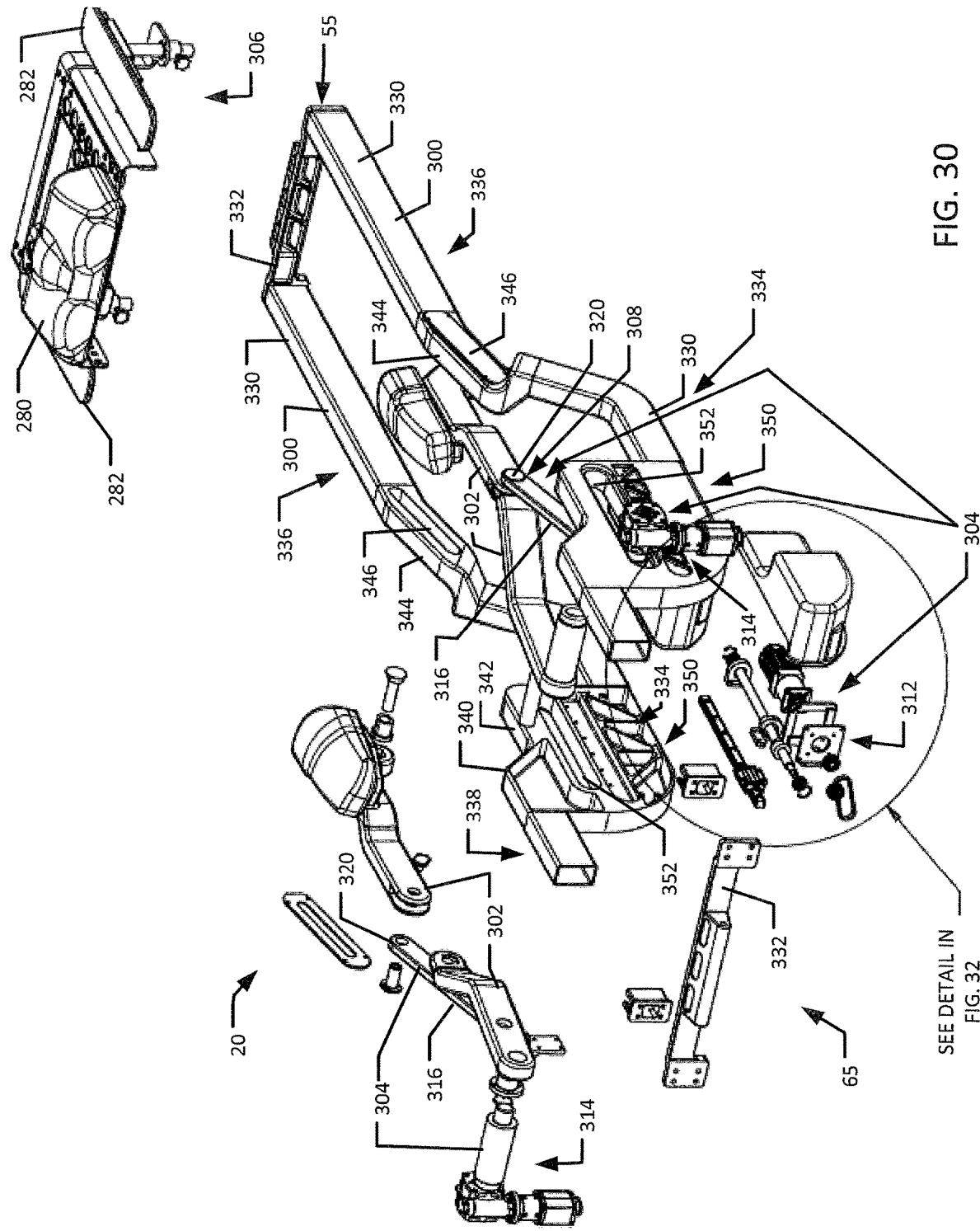
FIG. 30 is an exploded isometric view from a right side and foot end perspective of the patient support of FIG. 28.

FIGS. 28 and 29 are, respectively an isometric view and an exploded isometric view from a left side and head end perspective of the patient support 20, wherein the inner frame 302 is in a neutral position relative to the outer frame 300. FIG. 30 is also an exploded isometric view of the patient support 20, except from a right side and foot end perspective of the patient support 20. As can be understood from FIGS. 28-30 and described in greater detail below, the patient support 20 includes the outer frame 300, the inner frame 302, right and left inner frame drive assemblies 304, and a torso support assembly 306. The extreme opposed ends 55, 65 of the outer frame 300 are the respective head end 55 and foot end 65 of the patient support 20 discussed above with respect to FIGS. 1-4.

As shown in FIGS. 28-30, the torso support 306 is supported on a head end region of the outer frame 300. The torso support includes a chest pad 280 and right and left arm supports 282.

As indicated in FIGS. 1-4, the torso support 306 is configured to support the torso and arms of the patient 12 when in a prone position on the patient support 20. The torso support 306 does not displace along the outer frame 300 as a function of the inner frame 302 displacing relative to the outer frame 300. However, the torso support 306 is adjustable along the outer frame 300 to provide for proper placement of the chest pad 280 and arm pads 282 as need to accommodate the size of the patient 12.

As can be understood from FIGS. 28-30, the outer frame 300 defines a structure on which the inner frame 302, the drive assemblies 304 and the torso support assembly 306 are mounted. The outer frame 300 is rigid in that it does not change with respect to configuration or arrangement. In other words, the outer frame 300 does not have a joint along its length or width that allows the outer frame 300 to articulate relative to itself along its length, width or height.

In contrast to the outer frame 300, and as will be discussed in greater detail below, the inner frame 302 is not rigid, but has right and left articulation joints 308 along its length that allows the inner frame 302 to articulate relative to itself along its length and about the joint 308. Further, the inner frame 302 is movably coupled to the outer frame at right and left slider joints 310 to be both pivotally displaceable relative to the outer frame 300 and slidably displaceable relative to the outer frame 300.

The drive assemblies 304 act between the outer frame 300 and the articulation joints 308 to bring about the articulation of the inner frame 302 at the articulation joints 308 and the accompanying pivoting and sliding of the inner frame 302 relative to the outer frame 300 at the slider joints 310. As discussed in detail below, each drive assembly 304 includes a linear drive assembly 312, a rotation drive assembly 314, and a link arm 316 that transfers forces from the respective drive assembly 304 to the respective articulation joint 308 of the inner frame 302 to bring about displacement of the inner frame 302 relative to the outer frame 300 and to also bring about articulation of the inner frame 302 about itself at the articulation joints 308.

The outer frame 300 is rolled and pivoted via the head end pivot/roll assembly 130 and the foot end pivot/roll assembly 140 between which the outer frame 300 extends as a rigid frame work that does not change structural configuration and also does not articulate relative to or about itself. The inner frame 302 is coupled to the outer frame 300 to both pivot and slide relative to the outer frame 300 that serves as the unchanging base on which the inner frame 300 also articulates relative to and about itself. The drive assembly 314 brings about both the articulation of the inner frame 302 and the pivoting and sliding displacement of the inner frame 302 relative to the outer frame 300.

a. The Rigid Outer Frame

As indicated in FIGS. 28-30, the outer frame 300 of the patient platform 20 includes the head end 55, the foot end 65 opposite the head end 55, and right and left side structures 330 that extend between end members 332 at the head and foot ends 55, 65. The end members 332 join together the side structures 330 to form the generally rectangular outer frame 300.

Each side structure 330 includes a lower or depressed center region 334 approximately midway between a head end region 336 and a foot end region 338 that are higher than the depressed center region 334. To provide right-to-left clearance for the inner frame 302, the foot end region 338 is wider right-to-left than the head end region 334, and the transition in width occurs caudad of the head end region 336 and, in some instances, along at least a portion of the center region 334. Each depressed center region 334 includes a multi-tiered surface including a sloped surface 340 and a horizontal surface 342. The sloped surface 340 extends from the foot region 338 towards the head end 55, and the horizontal surface 342 extends from the sloped surface 340 towards the head end 55.

A slightly sloped transition region 344 between the head end region 336 and the depressed center region 334 transitions between these two regions and includes a slightly inclined slider slot 346 defined therein. Such slider slots 346 are part of a pivoting and sliding coupling between the outer frame 300 and the inner frame 302, as discussed below.

Each depressed center region 334 also includes a drive assembly support structure 350 that supports a drive assembly 304. The drive assembly support structure 350 includes a horizontal slot 352 along which the rotation drive assembly 314 and an end of the link arm 316 displaces.

b. The Displaceable and Articulating Inner Frame

Figure 31:
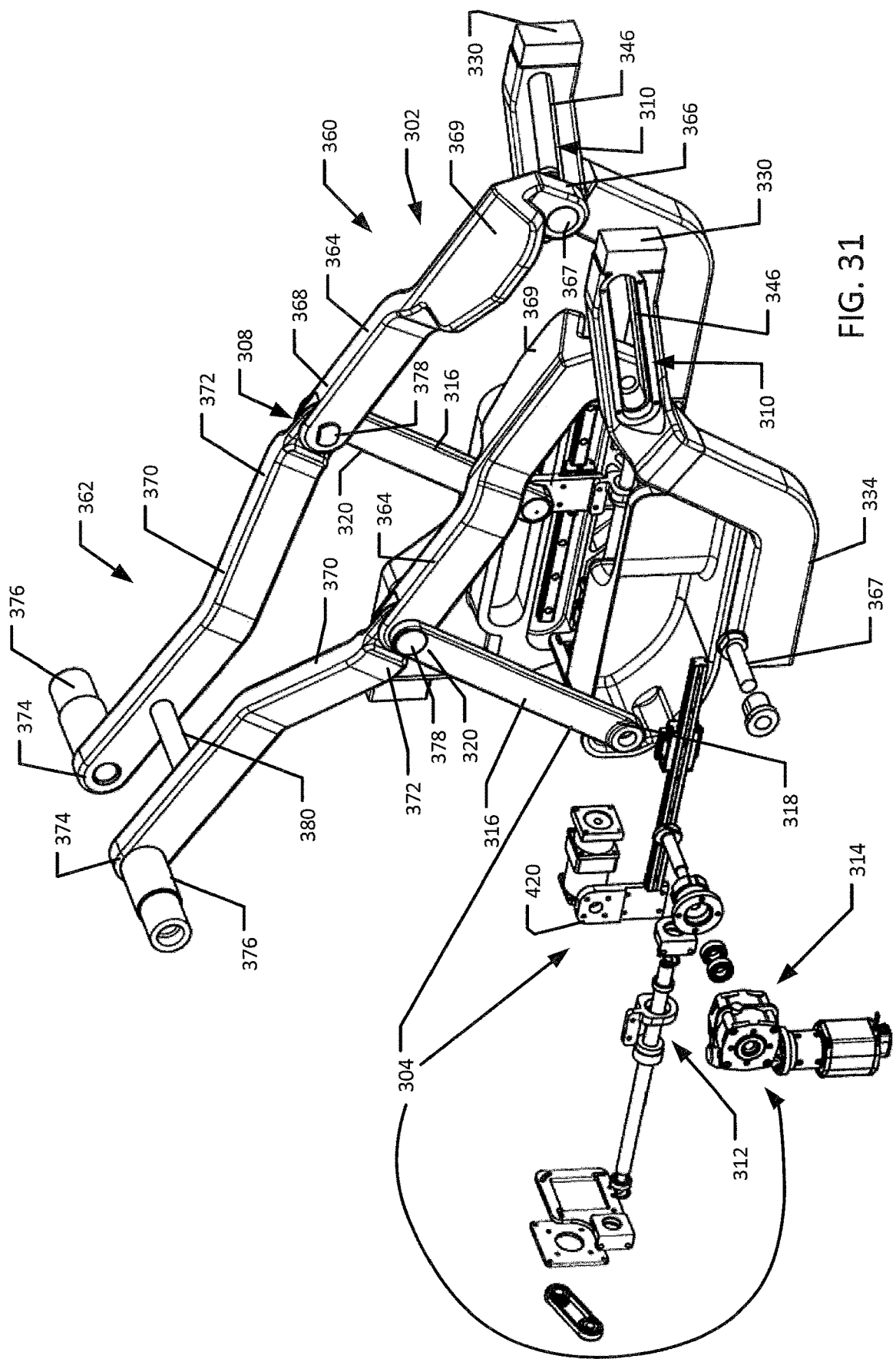
FIG. 31 is an exploded isometric view of the drive assemblies, inner frame and the depressed regions of the side structures of the outer frame as viewed from a right side and head end perspective, wherein the inner frame is in an elevated position relative to the outer frame.

FIG. 31 is an exploded isometric view of the drive assemblies 314, inner frame 302 and the depressed regions 334 of the side structures 330 of the outer frame 300 as viewed from a right side and head end perspective, wherein the inner frame 302 is in a neutral position relative to the outer frame 300. As shown in FIG. 31, the inner frame 302 includes a head end or upper leg member or region 360 and a foot end or lower leg member or region 362. The head end region 360 includes right and left first members 364, each such member including a slider end 366 and an articulation joint end 368. A hip pad 369 is located on each first member 364 adjacent the slider end 366. A slider pin 367 couples each slider end 366 to its respective slider slot 346 defined in the side structures 330 of the outer frame 300 resulting in a sliding and pivoting coupling relationship with the respective slider slot 346 to form the respective slider joint 310.

The foot end region 362 includes right and left second members 370, each such member including an articulation joint end 372 and a free end 374. Contact members 376 extend horizontally and perpendicularly from the free ends 374 in a pivotal coupling arrangement. A cross member 380 extends between the pair of second members 370 near the free ends 374.

The articulation joint ends 368, 372 are pivotally coupled to each other via an articulation joint pin 378 to form the articulation joints 308 of the inner frame 302, and as will be discussed below, the link arms 316 are also pinned to the articulation joints 308 via the pins 378. Thus, actuation of the drive assemblies 304 cause the link arms 316 to act against the articulation joints 308, bringing about displacement of the inner frame 302 relative to the outer frame 300 and also causing the foot end region 362 of the inner frame 302 to articulate relative to the head end region 360 of the inner frame 302 about the articulation joints 308.

Figure 42A:
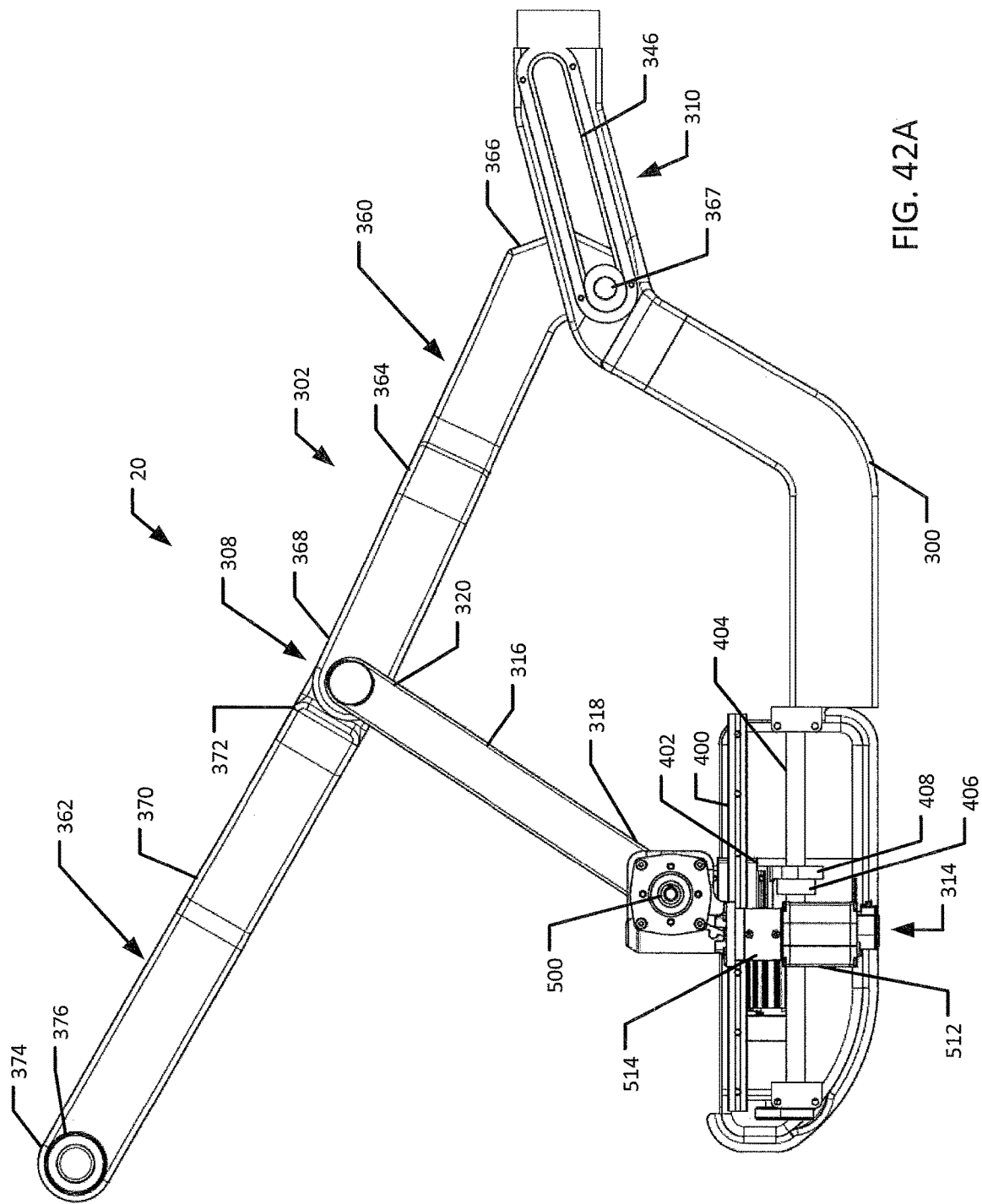
FIGS. 42A-42C are right side elevation views of the right recessed region of the outer frame and corresponding right drive assembly, link arm, and inner frame components, the inner frame depicted in the elevated position, the neutral position and the lower position, respectively.
Figure 42B:
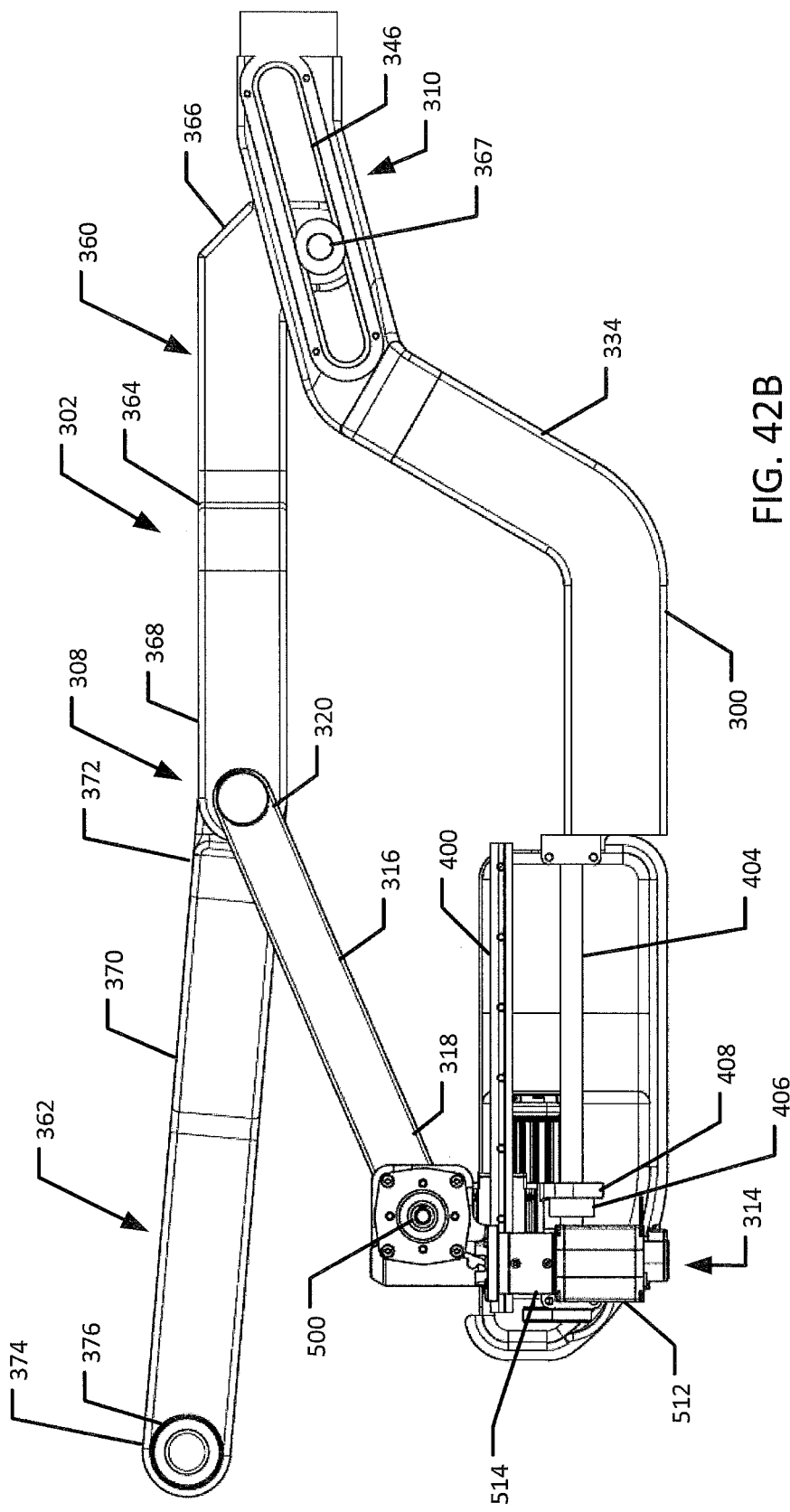
Figure 42C:
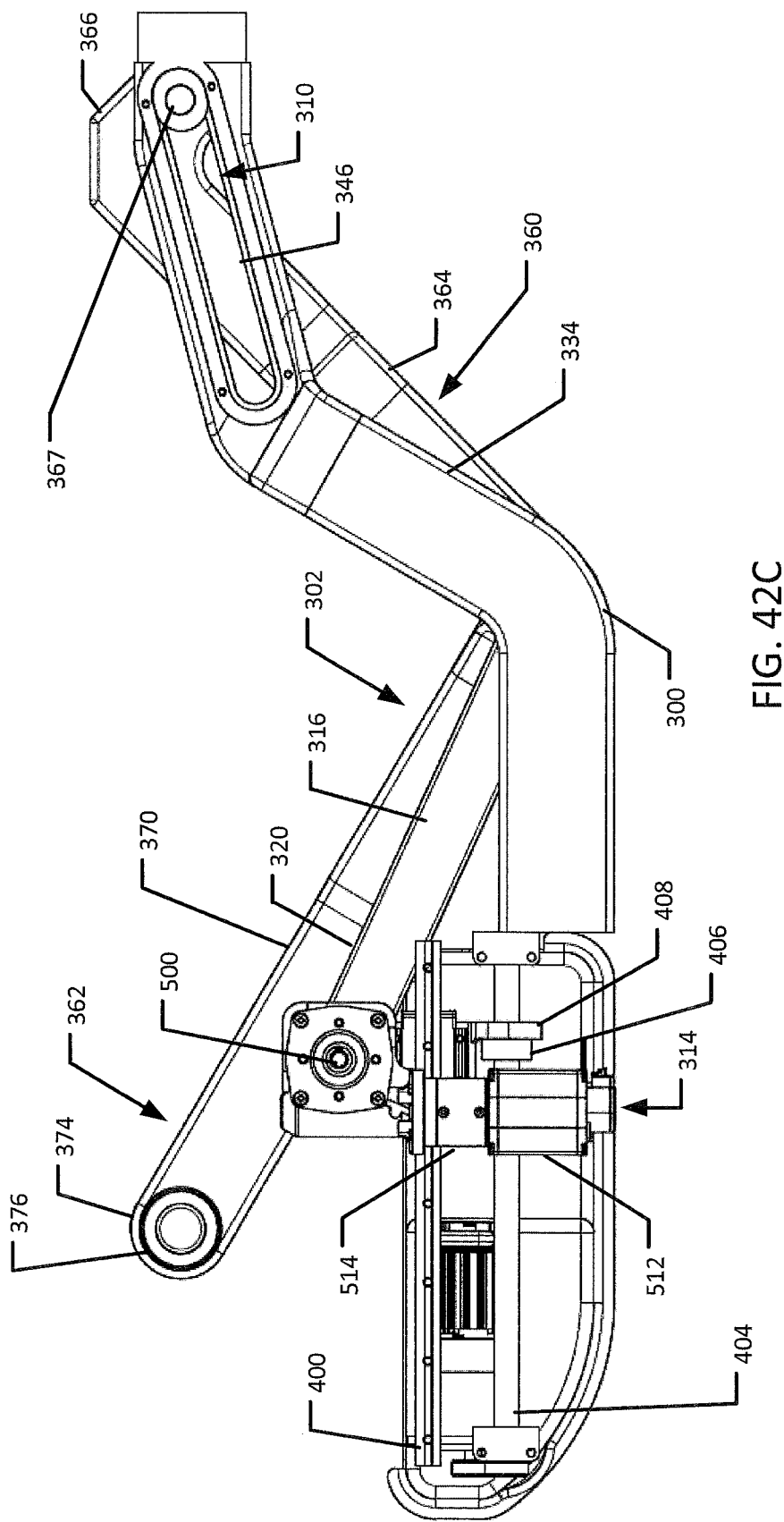
Figure 43B:
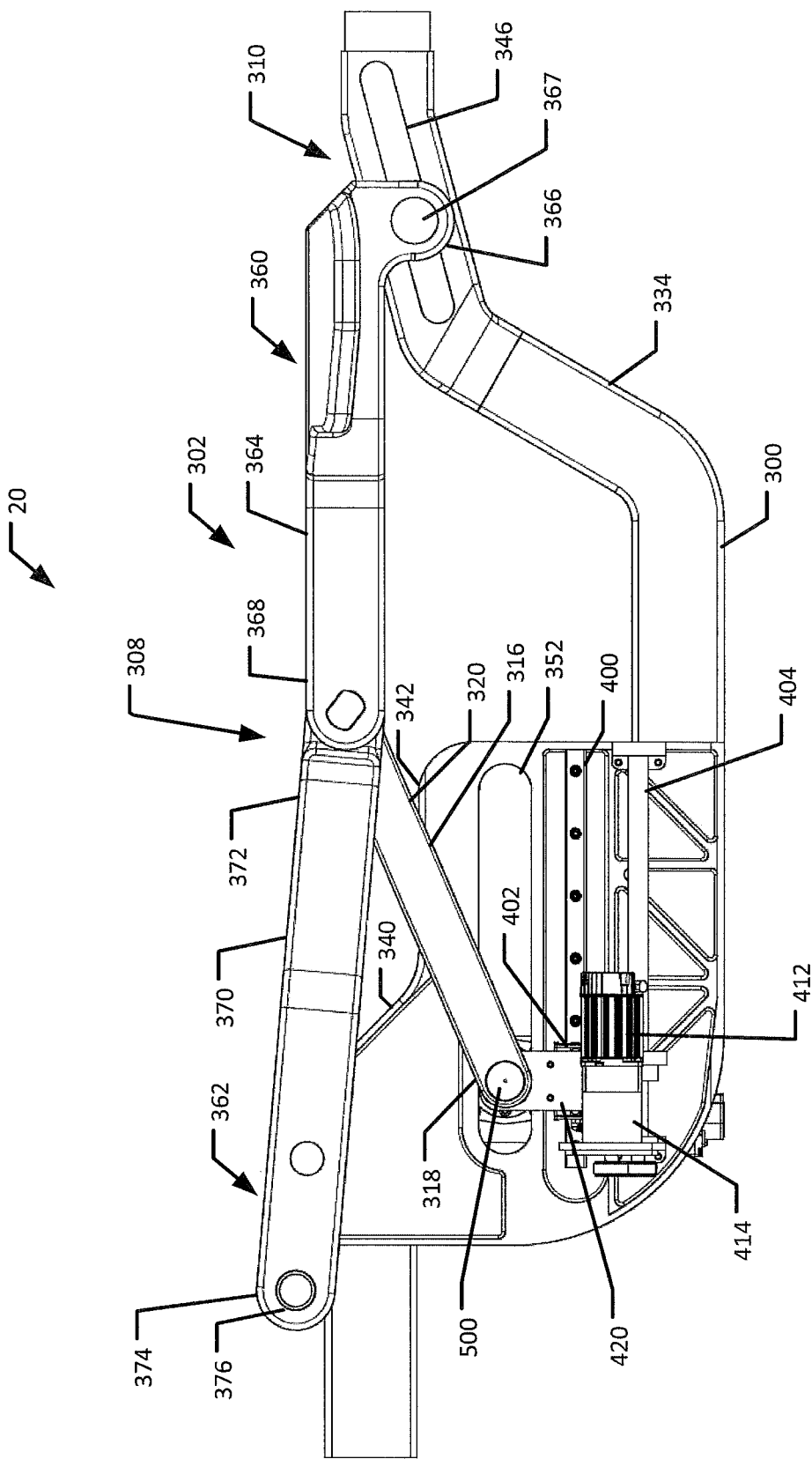
Figure 43C:
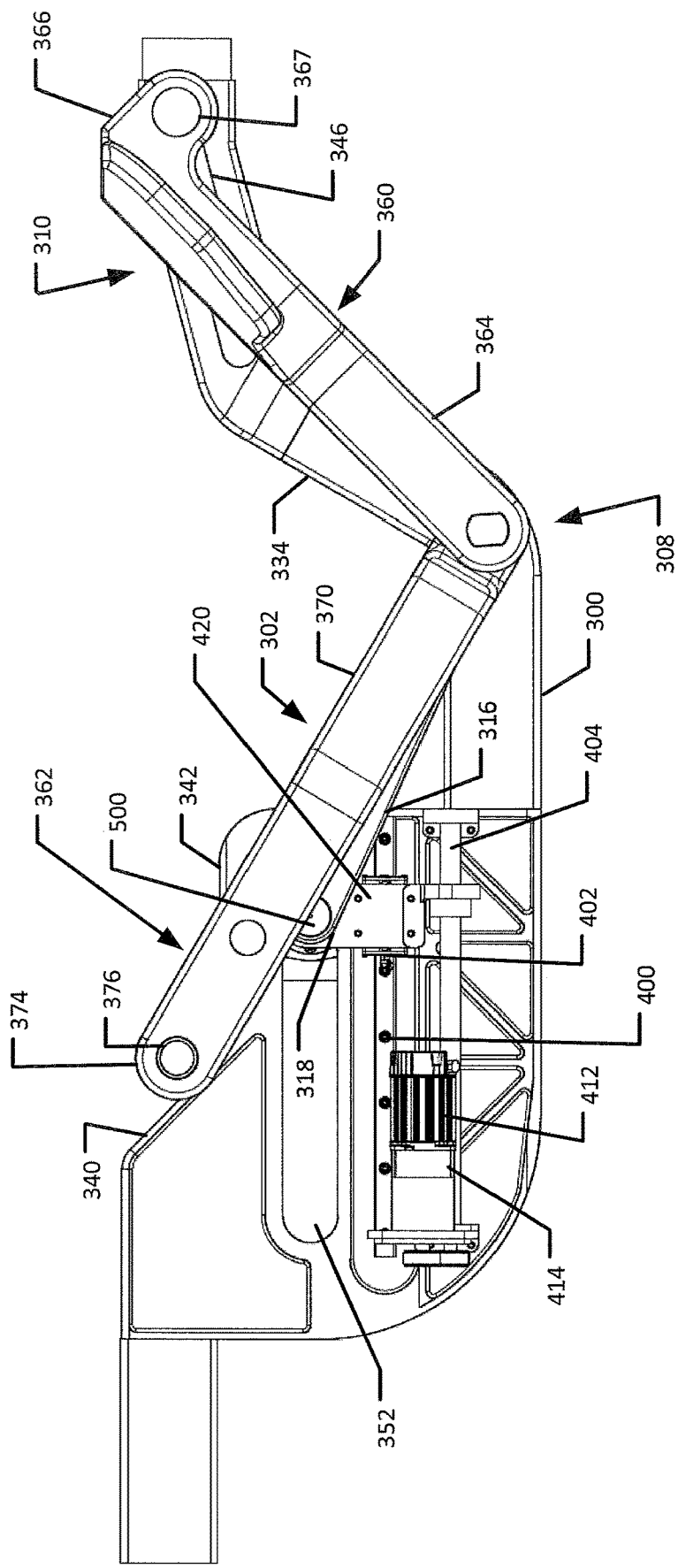

As can be understood from FIGS. 42A-43C, the mechanical arrangement of the articulation joint 308 formed by the articulation joint ends 368, 372 is such that the free end 374 can pivot upwardly relative to the articulation joint 308, as is the case when the inner frame 302 assumes the lower position indicated in FIGS. 42C and 43C. However, on account of an interlocking mechanical arrangement between the articulation joint ends 368, 372 of the first and second members 364, 370 at the articulation joint 308, the free end 374 is prevented from rotating downward relative to the articulation joint 308 to any degree lower than the articulation joint 308. Thus, as indicated in FIGS. 42A-42B and 43A-43B, the result is the first and second members 364, 370 form a straight line when the free end 374 reaches its greatest downward extent relative to the articulation joint 308, as is the case when the inner frame is in the elevated position (see FIGS. 42A and 43A) or when the inner frame is in the neutral position (see FIGS. 42B and 43B).

c. The Inner Frame Drive Assemblies

As can be understood from FIGS. 28, 30 and 31, the drive assemblies 304 act between the outer frame 300 and the articulation joints 308 to bring about the articulation of the inner frame 302 at the articulation joints 308 and the accompanying pivoting and sliding of the inner frame 302 relative to the outer frame 300 at the slider joints 310. Each drive assembly 304 includes a linear drive assembly 312, a rotation drive assembly 314, and a link arm 316 including a lower end 318 and an upper end 320.

As can be understood from FIGS. 28-31, each link arm upper end 320 is coupled via the articulation joint pin 378 to a respective articulation joint 308 of the inner frame 302, and each link arm lower end 318 is coupled to, and pivotally driven by, a respective rotation drive assembly 314. Each rotation drive assembly 314 acts between a respective linear drive assembly 312 and respective link arm 316 to cause the link arm 316 to pivot in a plane extending lengthwise along the length of the rigid frame 300 and perpendicular to a right-to-left width of the rigid frame, thereby bringing about displacement and articulation of the respective articulation joint 308 and sliding at the respective slider joint 310.

Each linear drive assembly 312 acts between the outer frame 302 and a respective rotation drive assembly 314 to linearly displace the rotation drive assembly 314 relative to the outer frame 300, thereby adding to the articulation of the respective articulation joint 308 and sliding at the respective slider joint 310.

Electrical power to the inner frame drive assemblies can be routed through one or both ladder attachment assemblies 198, as seen in FIG. 22, or even one or both of the shafts 196, through the outer frame 300 and to the motors of the respective drives of the inner frame drive assemblies.

1. The Linear Drive Assemblies

Figure 32:
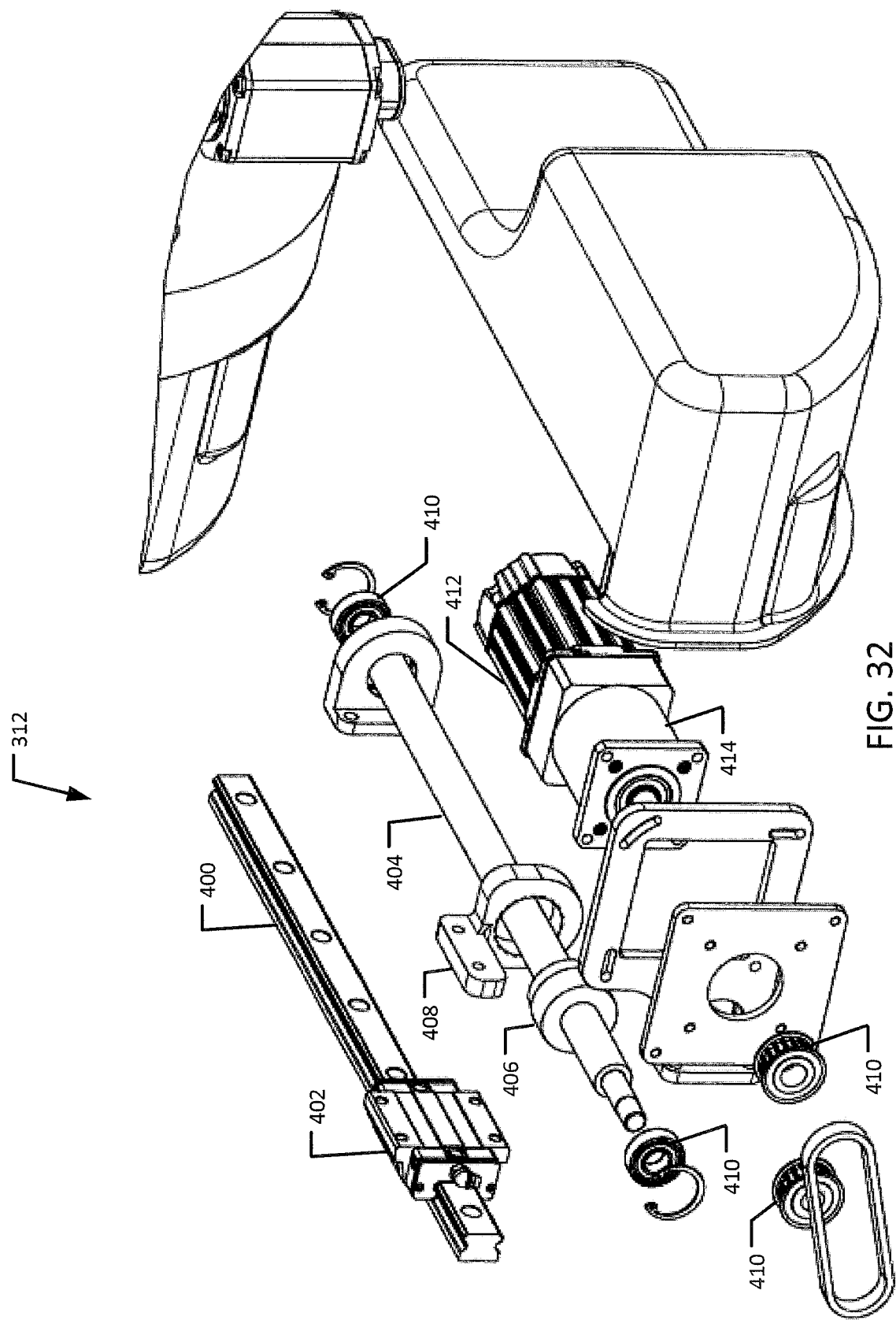
FIG. 32 is an exploded isometric view of the linear drive assembly as viewed from a right side and foot end perspective.

FIG. 32 is an enlarged view of the exploded linear drive assembly 312 illustrated in FIG. 30. As shown in FIG. 32, the linear drive assembly 312 includes a linear guide rail 400, a slider block 402, a lead screw 404, a lead screw nut 406 with its mount 408, various bearing rings 410, and a drive motor 412 with its gear box 414. A bearing block 420 may also be considered part of the linear drive assembly 312, and is depicted in FIG. 31.

Figure 33B:
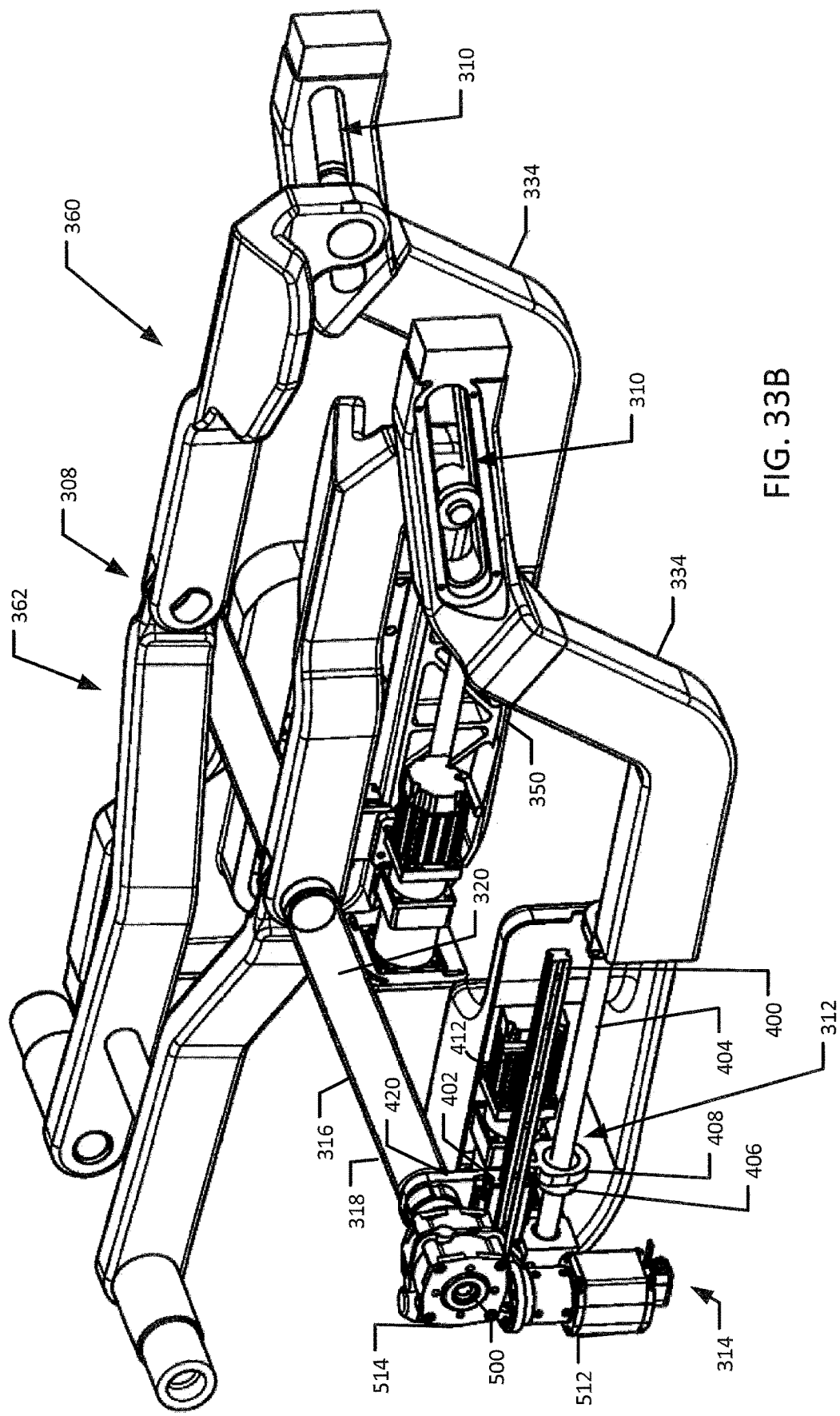
FIGS. 33B-33C are the same view as FIG. 33A, except illustrating the inner frame in neutral and lowered positions relative to the outer frame, respectively.
Figure 33C:
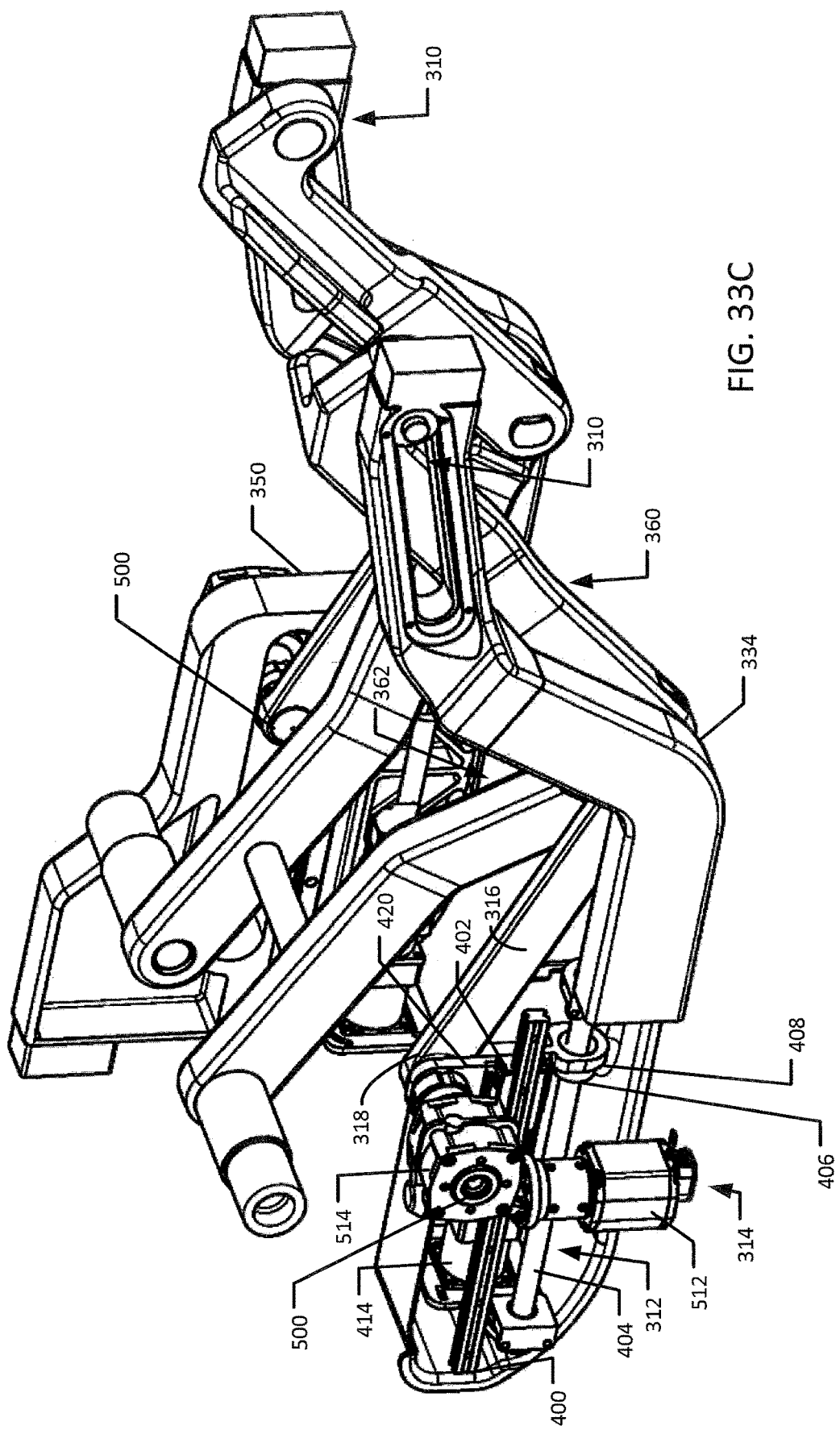
Figure 34B:
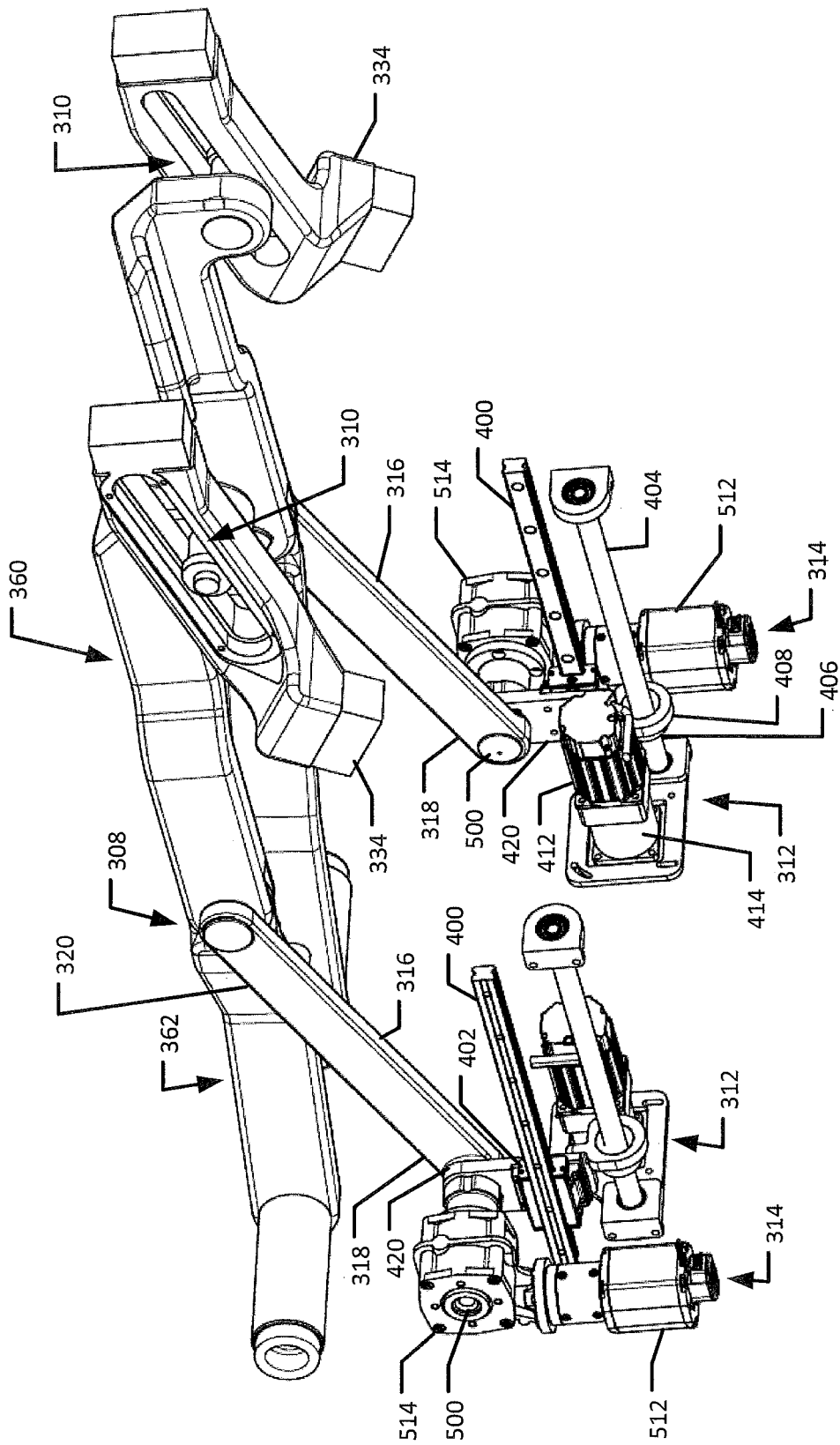
Figure 34C:
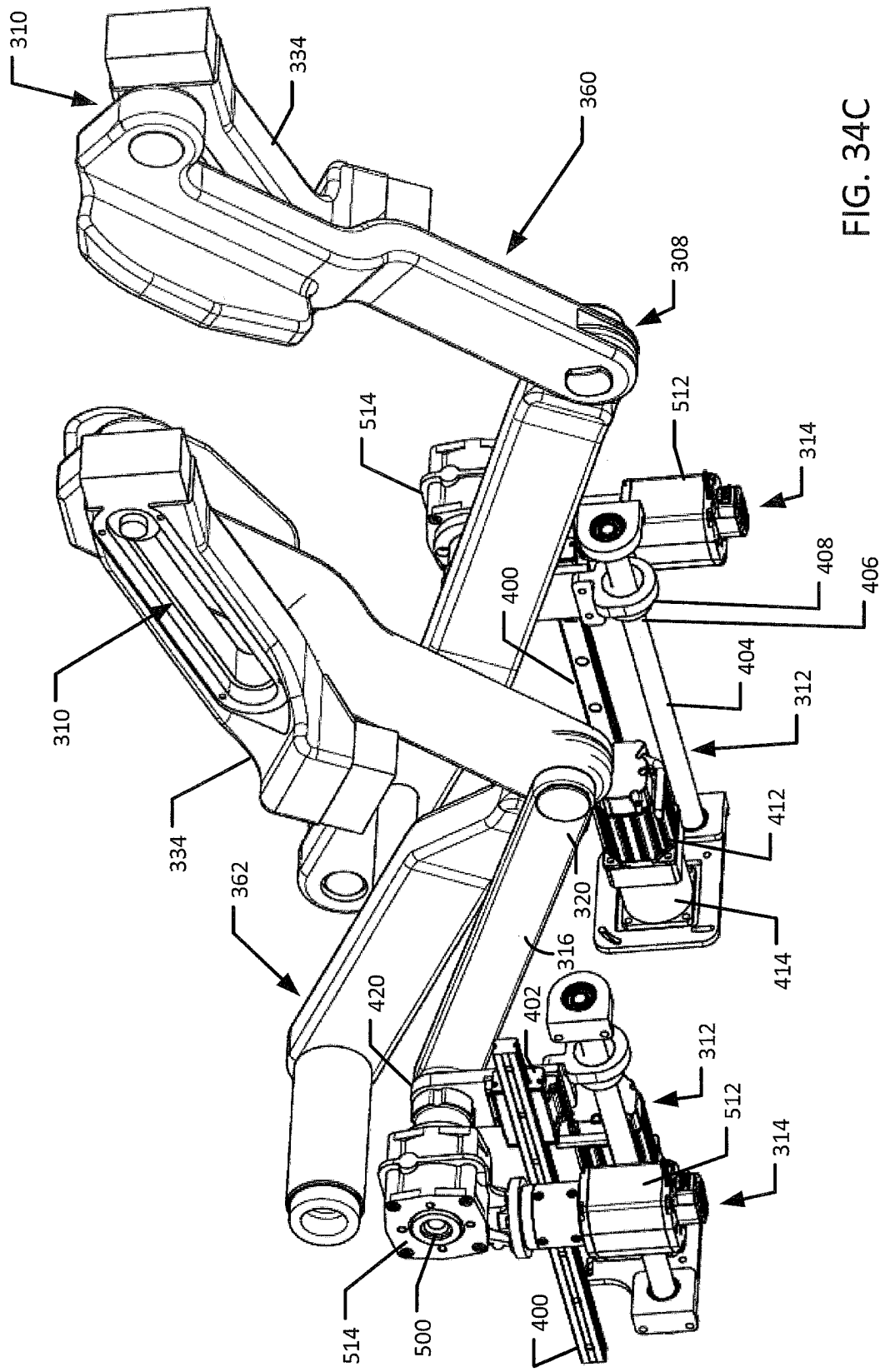

FIG. 33A is the same view as FIG. 31, except in an assembled state. FIGS. 33B-33C is the same view as FIG. 33A, except illustrating the inner frame 302 in a neutral and lowered positions relative to the outer frame, respectively. FIGS. 34A-34C illustrate same respective conditions and essentially the same components as FIGS. 33A-33C, except from a lower perspective. As shown in FIGS. 33A-34C, slider block 402 is mounted on the linear guide rail 400 in sliding engagement such that the slider block 402 can slide along the rail 400 back and forth in the directions of the head end and foot end of the patient platform 20. As indicated in FIGS. 33A-33C, the linear guide rail 400 is fixedly coupled to the drive assembly support structure 350 of the depressed center region 334 of the outer frame 300.

As depicted in FIGS. 33A-34C, the lead screw mount 408 couples the lead screw nut 406 to the slider block 402. The drive motor 412 is fixedly supported off of the drive assembly support structure 350 and, via its gear box 414, is configured to cause the lead screw 404 to rotate about its longitudinal axis. The lead screw 404 is pivotally supported off of the drive assembly support structure 350 in a parallel arrangement with the linear guide rail 400 and extends through the lead screw nut 406 in a threaded engagement. Thus, rotation of the lead screw 404 causes the coupled together lead screw nut 406 and its mount 408 to displace along the lead screw 404, thereby driving the slider block 402 along the linear guide rail 400. As the bearing block 420 couples the slider block 402 to the lower end 318 of the link arm 316, the linear displacement of the slider block 402 causes the lower end 318 of the link arm 316 to have the same linear displacement. Such linear displacement provides some articulation of the respective articulation joint 308 and sliding at the respective slider joint 310.

2. The Rotation Drive Assemblies

Figure 35:
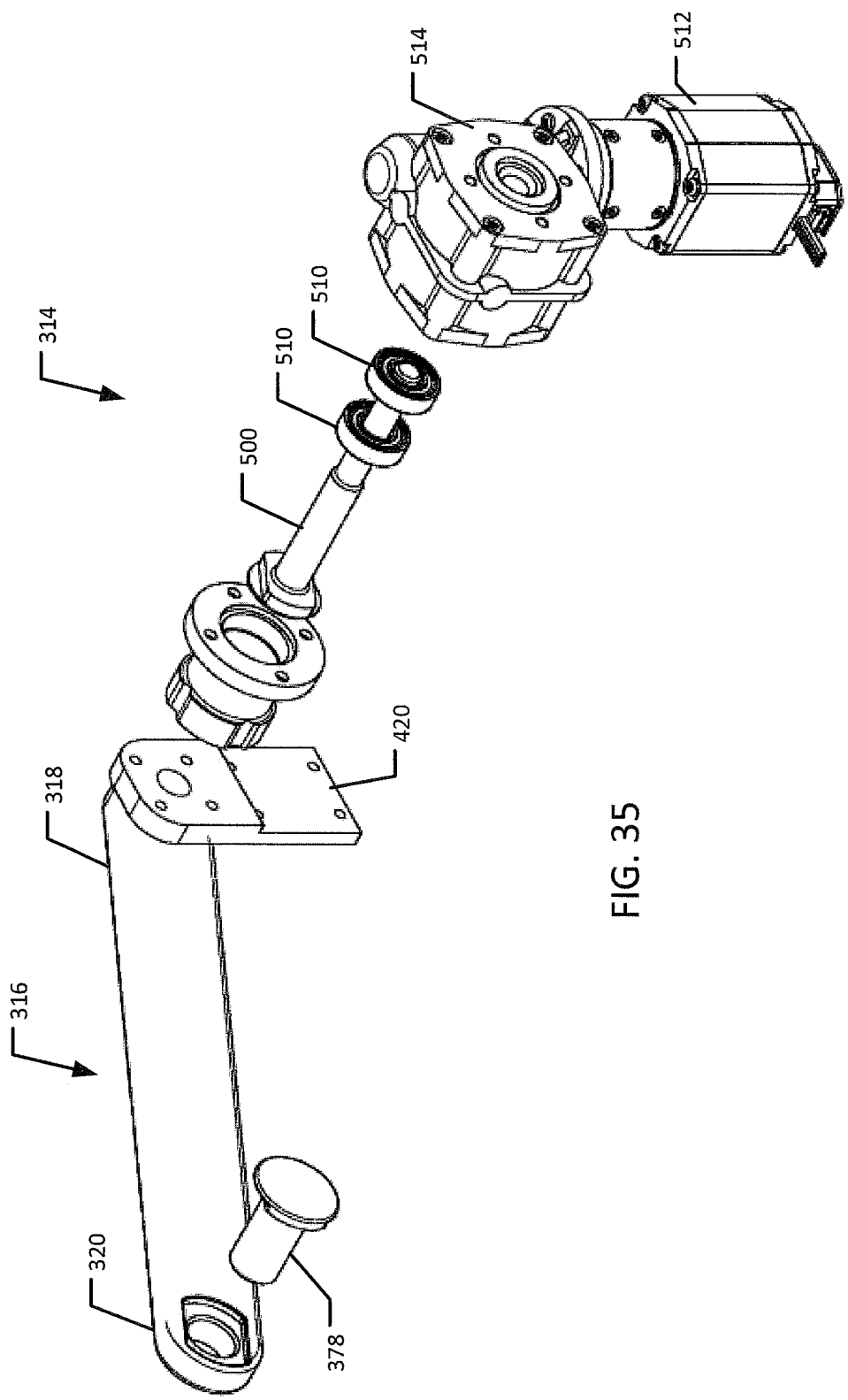
FIG. 35 is an enlarged view of the exploded rotation drive assembly illustrated in FIG. 29.
Figure 36A:
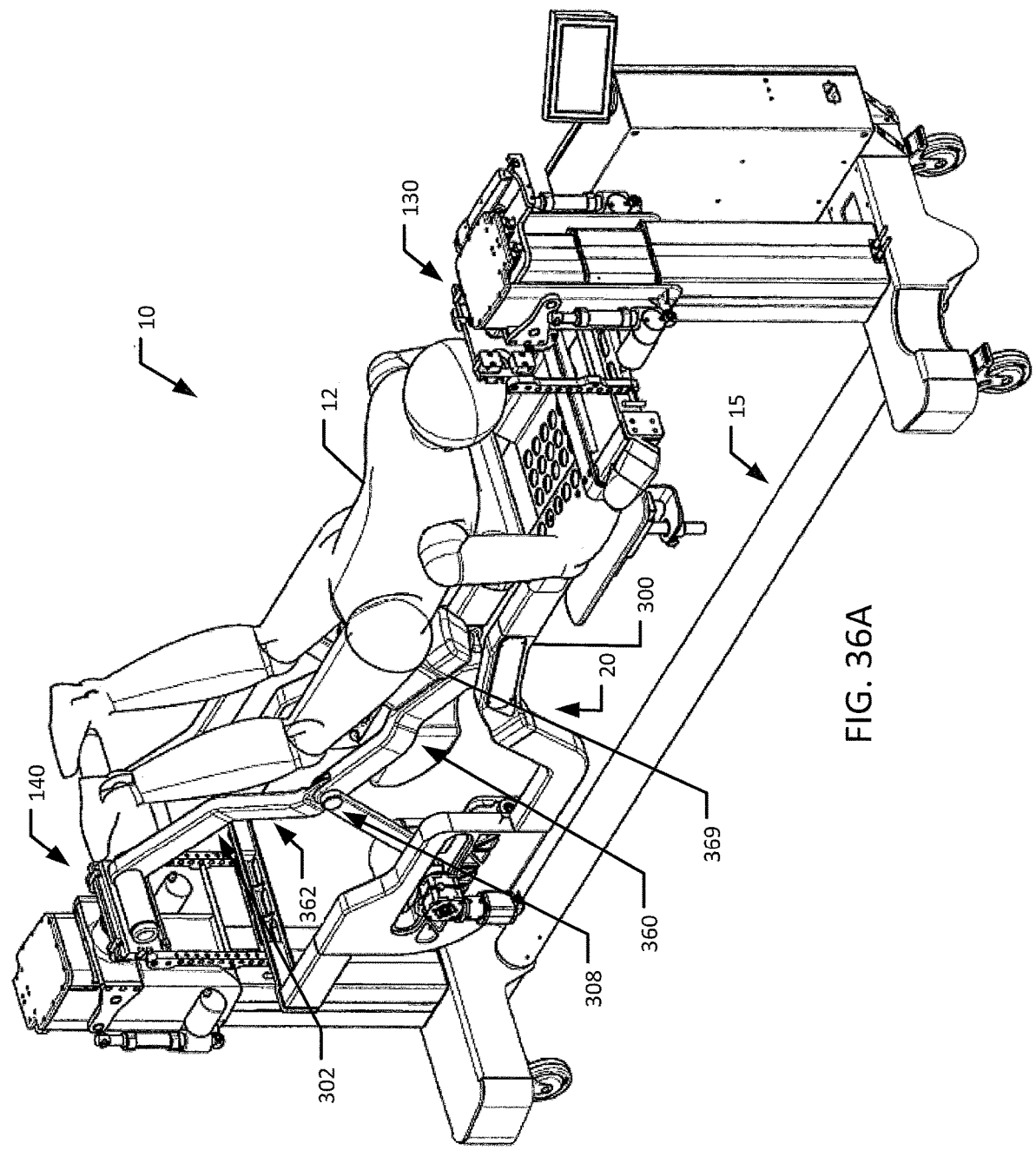
FIGS. 36A-36B are of the same view as FIG. 1, except, instead of the inner frame being in a neutral position as depicted in FIG. 1, the inner frame is in an elevated position and a lowered position, respectively.
Figure 36B:
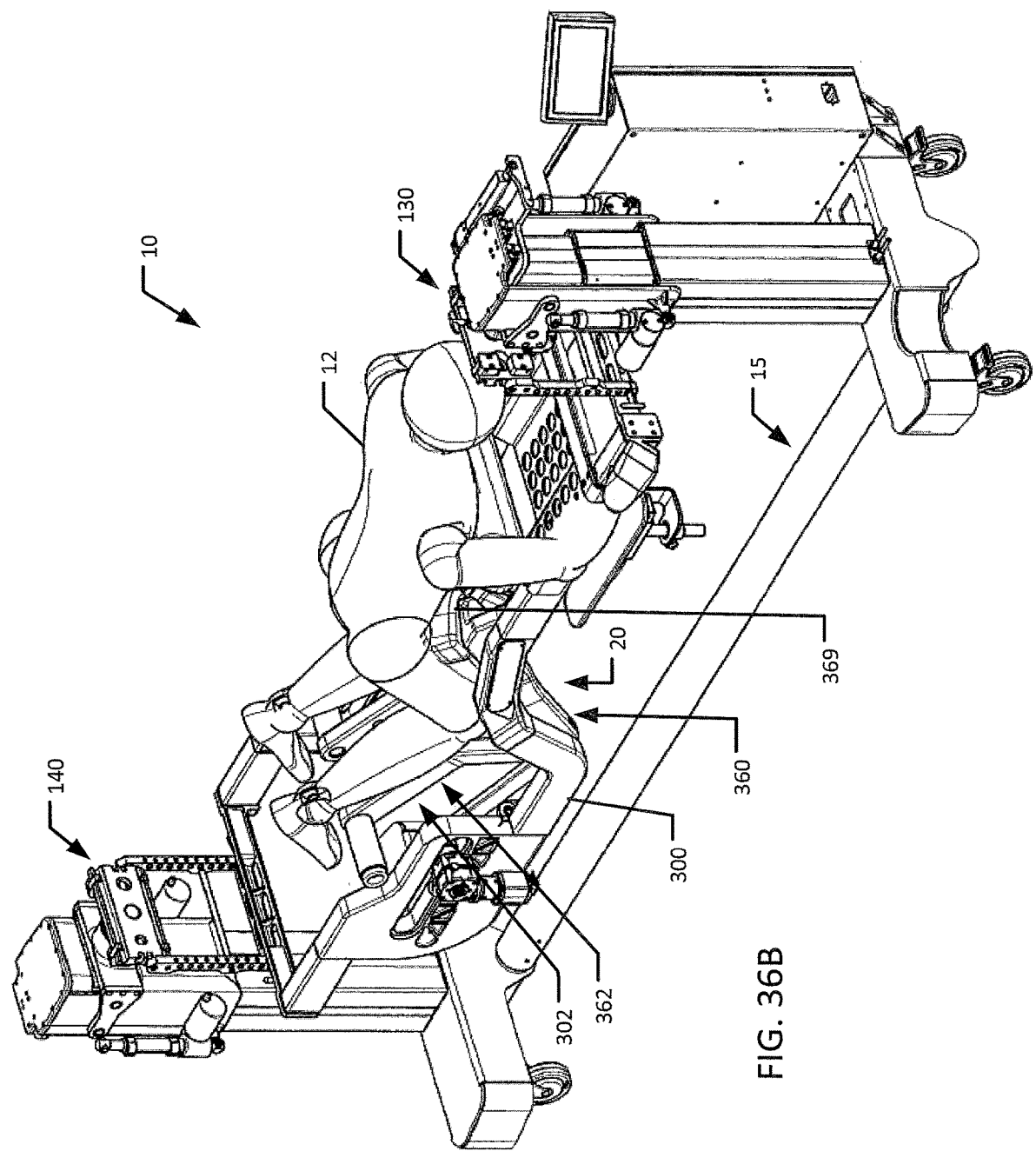
Figure 37A:
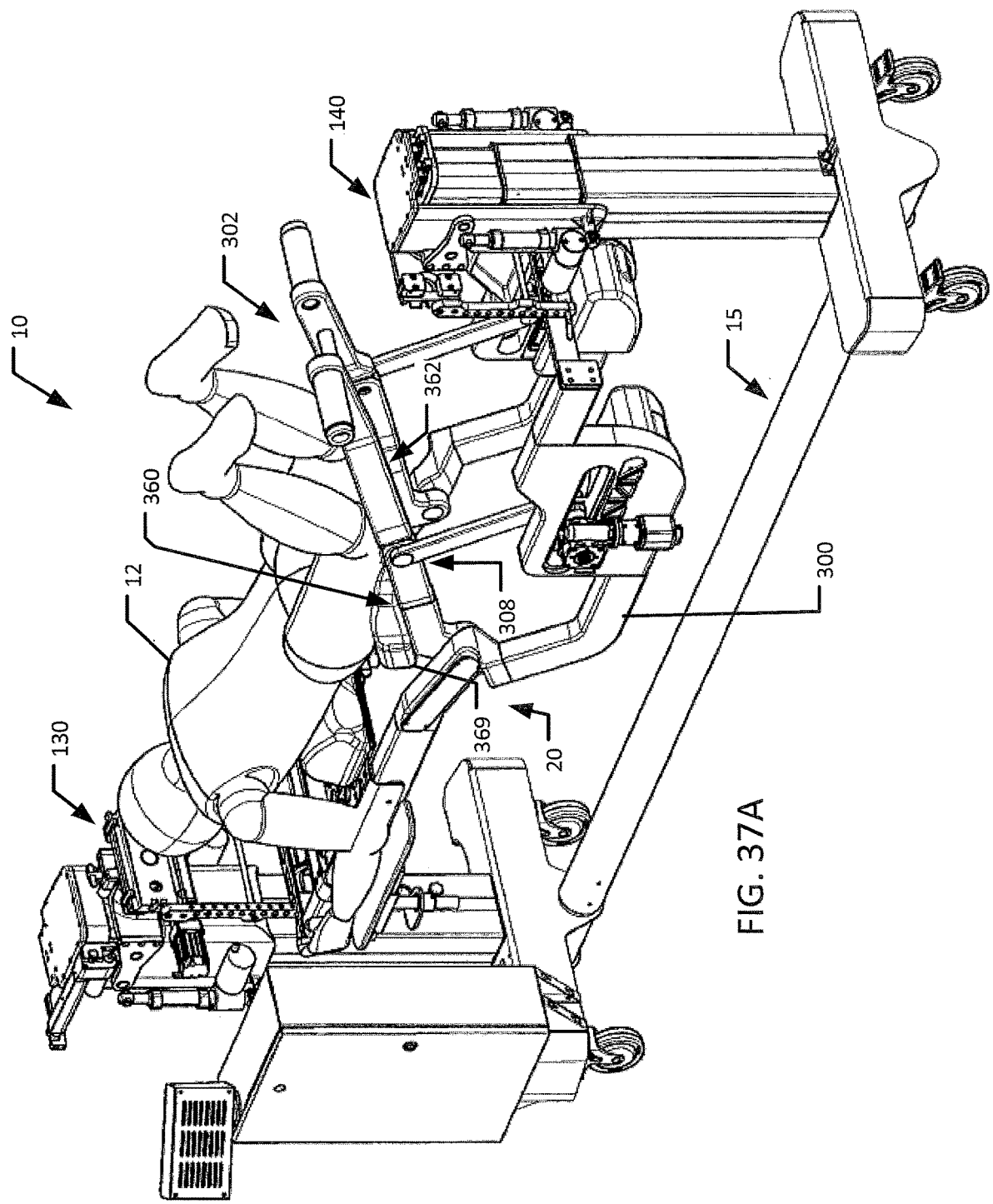
FIGS. 37A-37B are of the same view as FIG. 2, except, instead of the inner frame being in a neutral position as depicted in FIG. 2, the inner frame is in an elevated position and a lowered position, respectively.
Figure 37B:
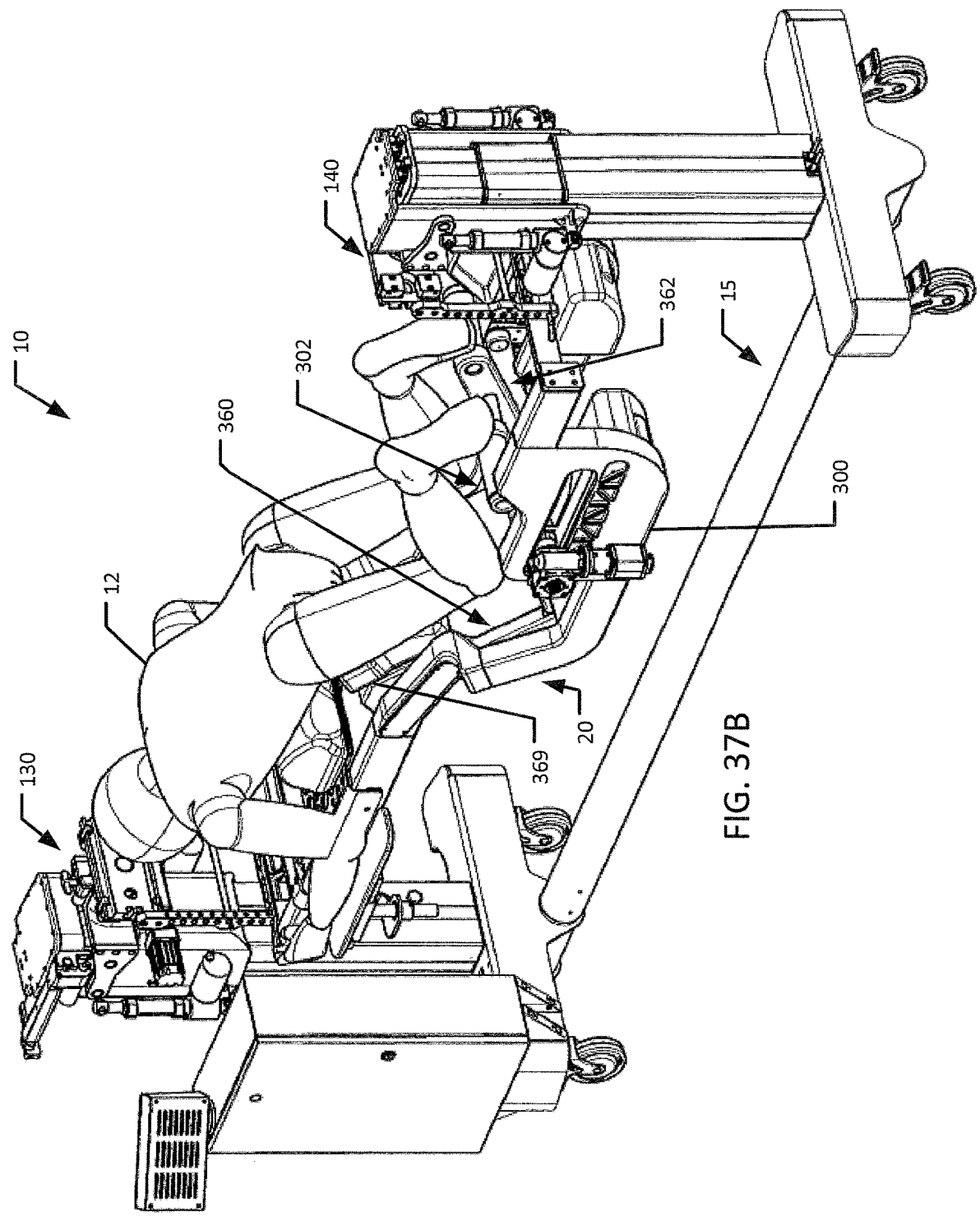
Figure 38A:
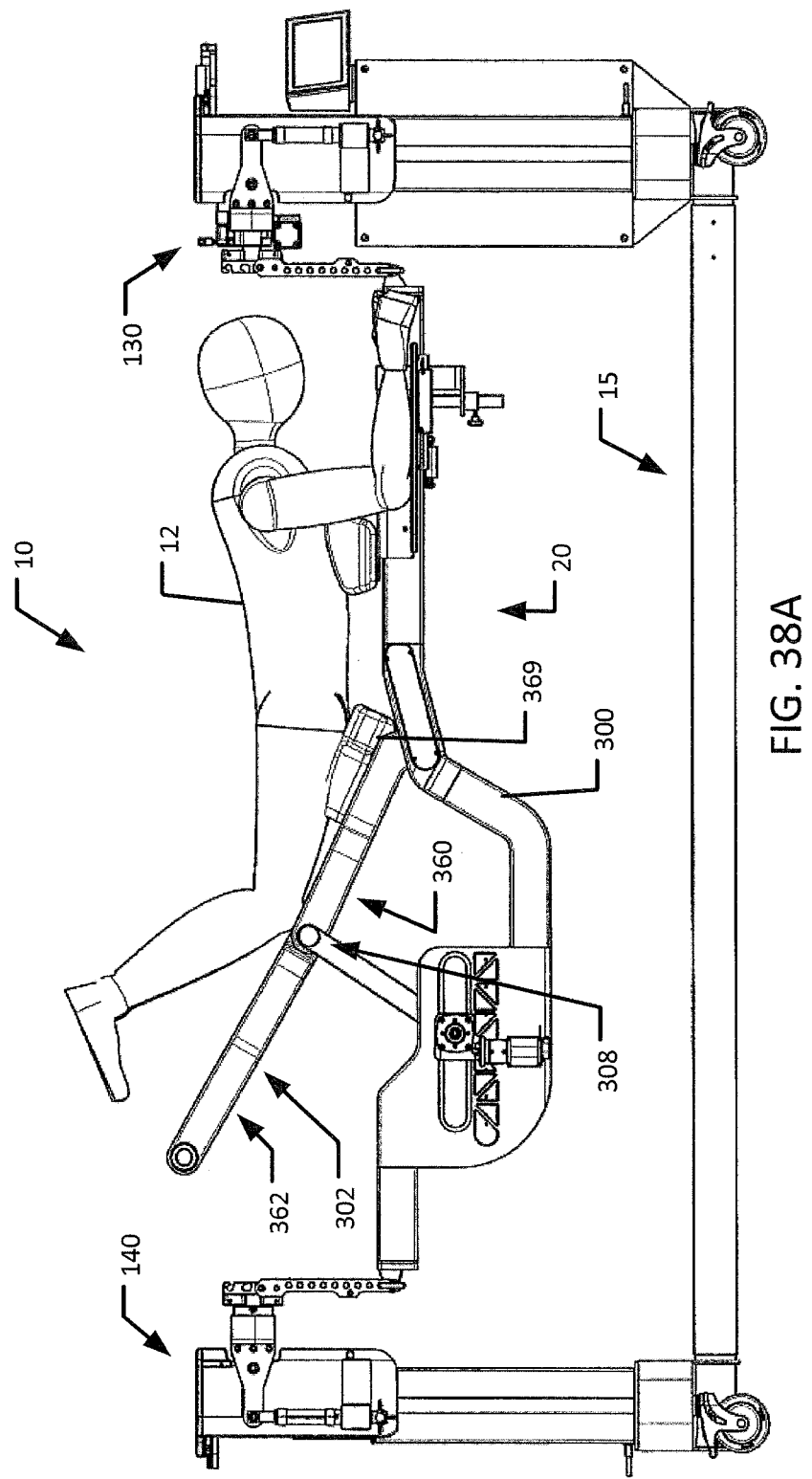
Figure 39A:
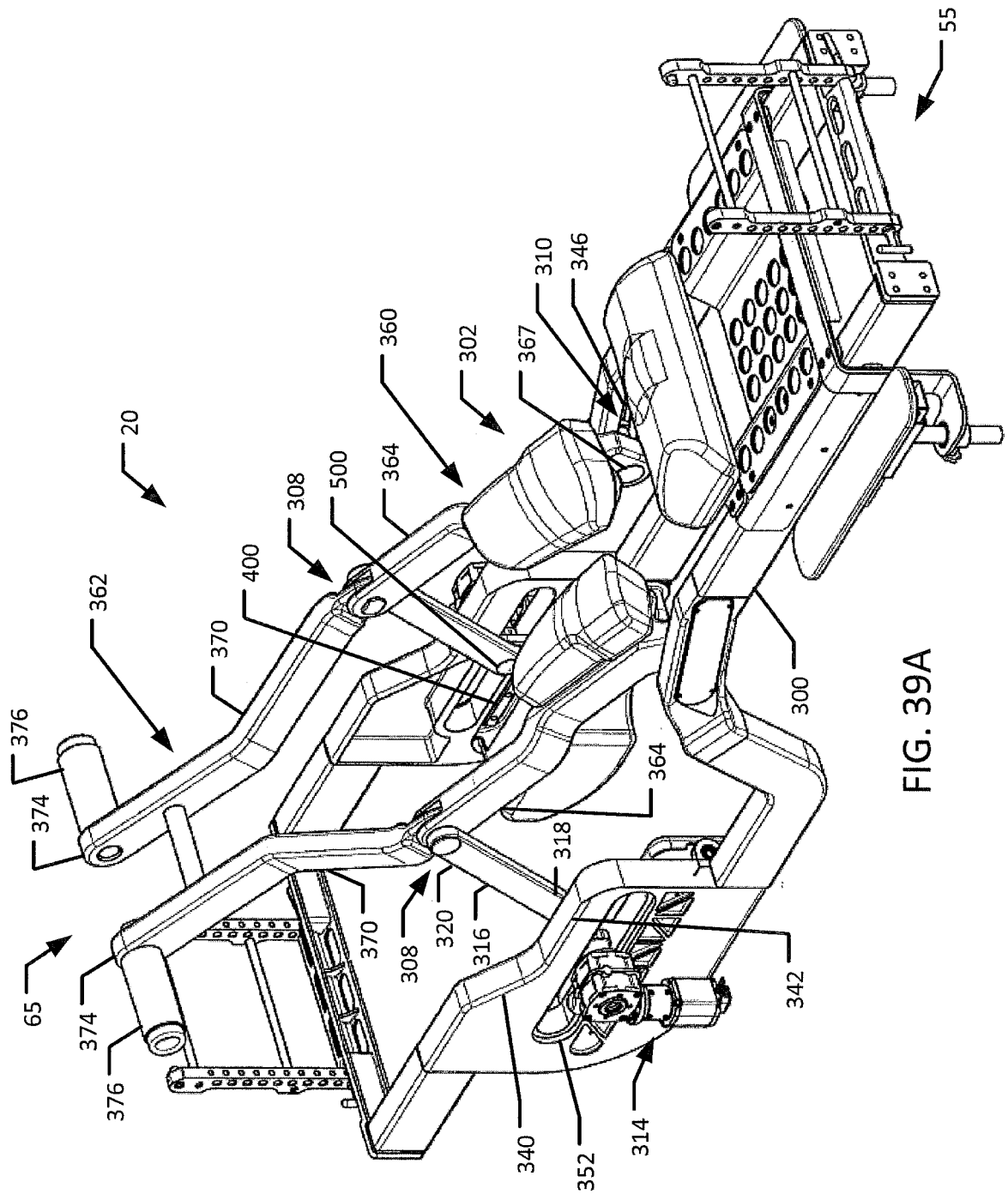
FIGS. 39A-39C are of the same view as FIG. 1, except only depicting the patient support and H-frames, with the inner frame shown in the elevated position, the neutral position and the lower position, respectively.
Figure 39B:
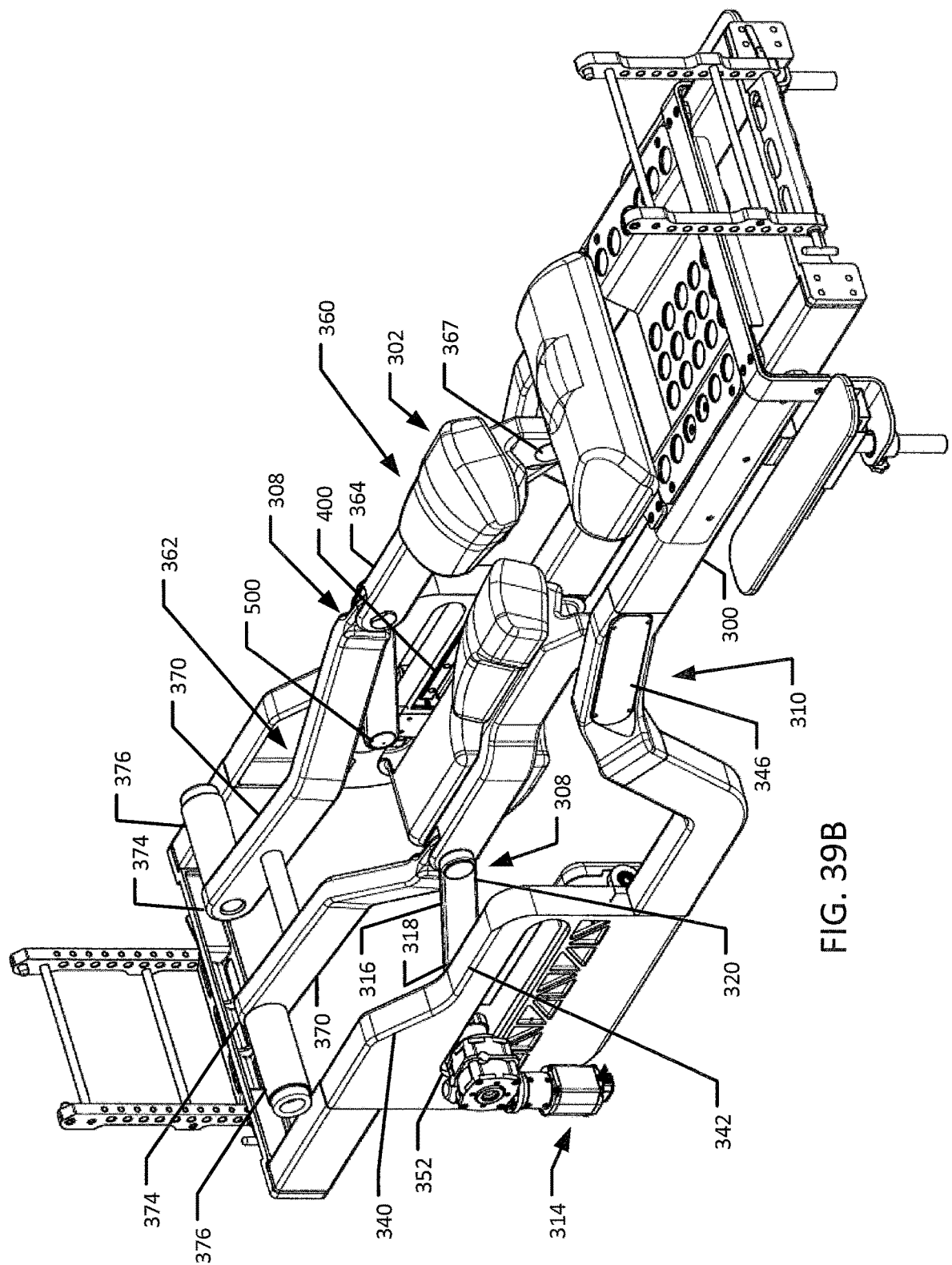
Figure 39C:
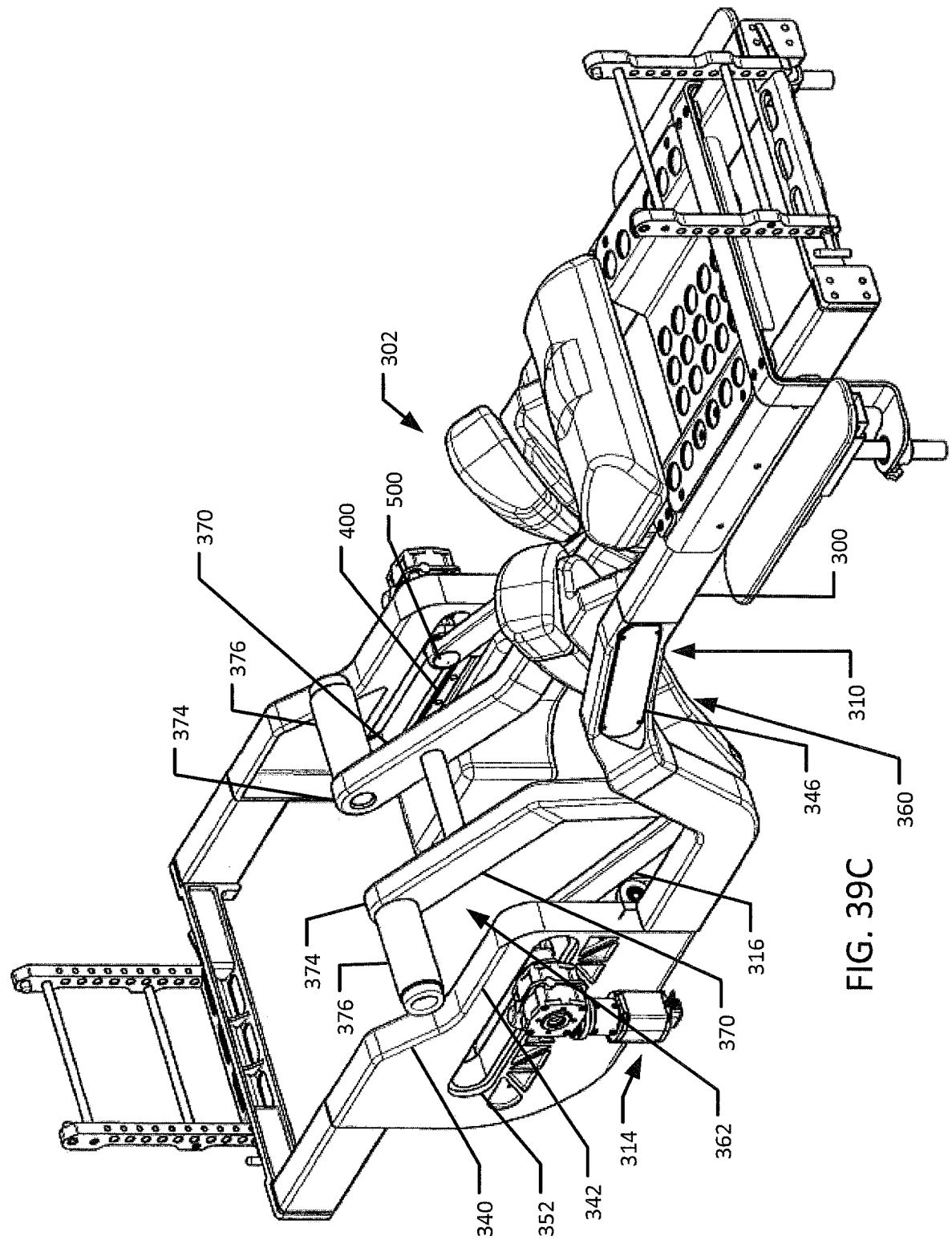
Figure 40A:
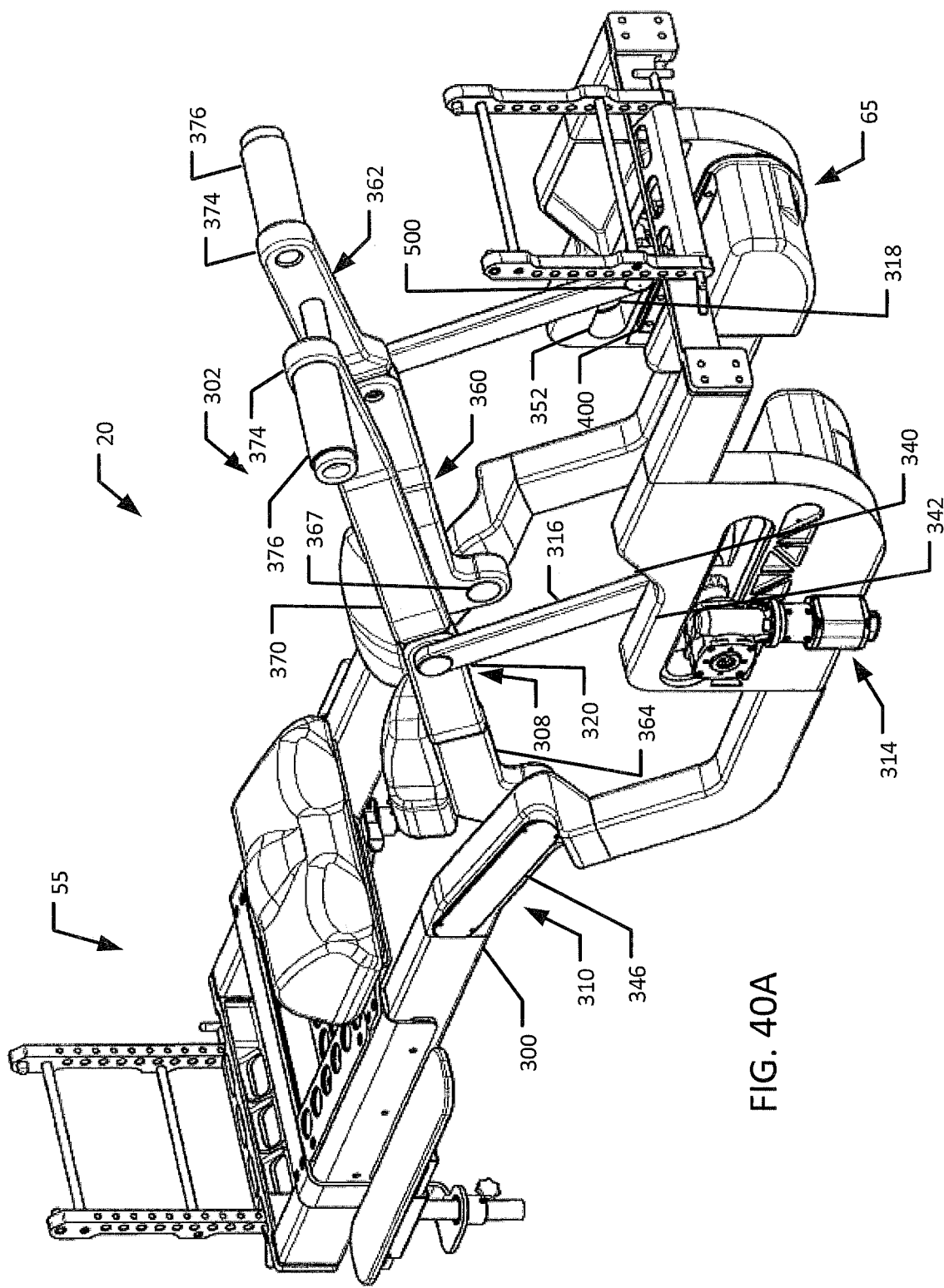
FIGS. 40A-40C are of the same view as FIG. 2, except only depicting the patient support and H-frames, with the inner frame shown in the elevated position, the neutral position and the lower position, respectively.
Figure 40B:
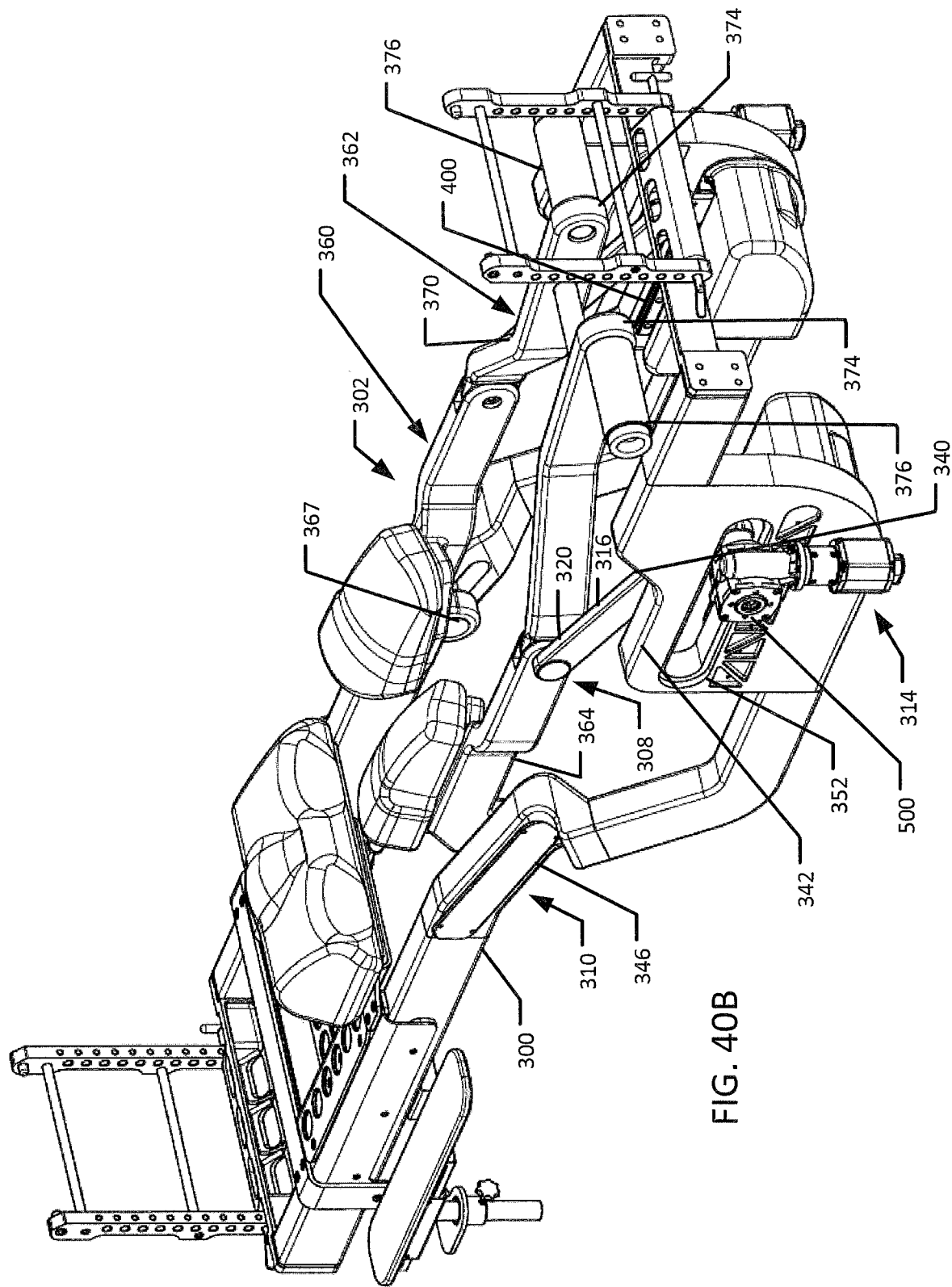
Figure 40C:
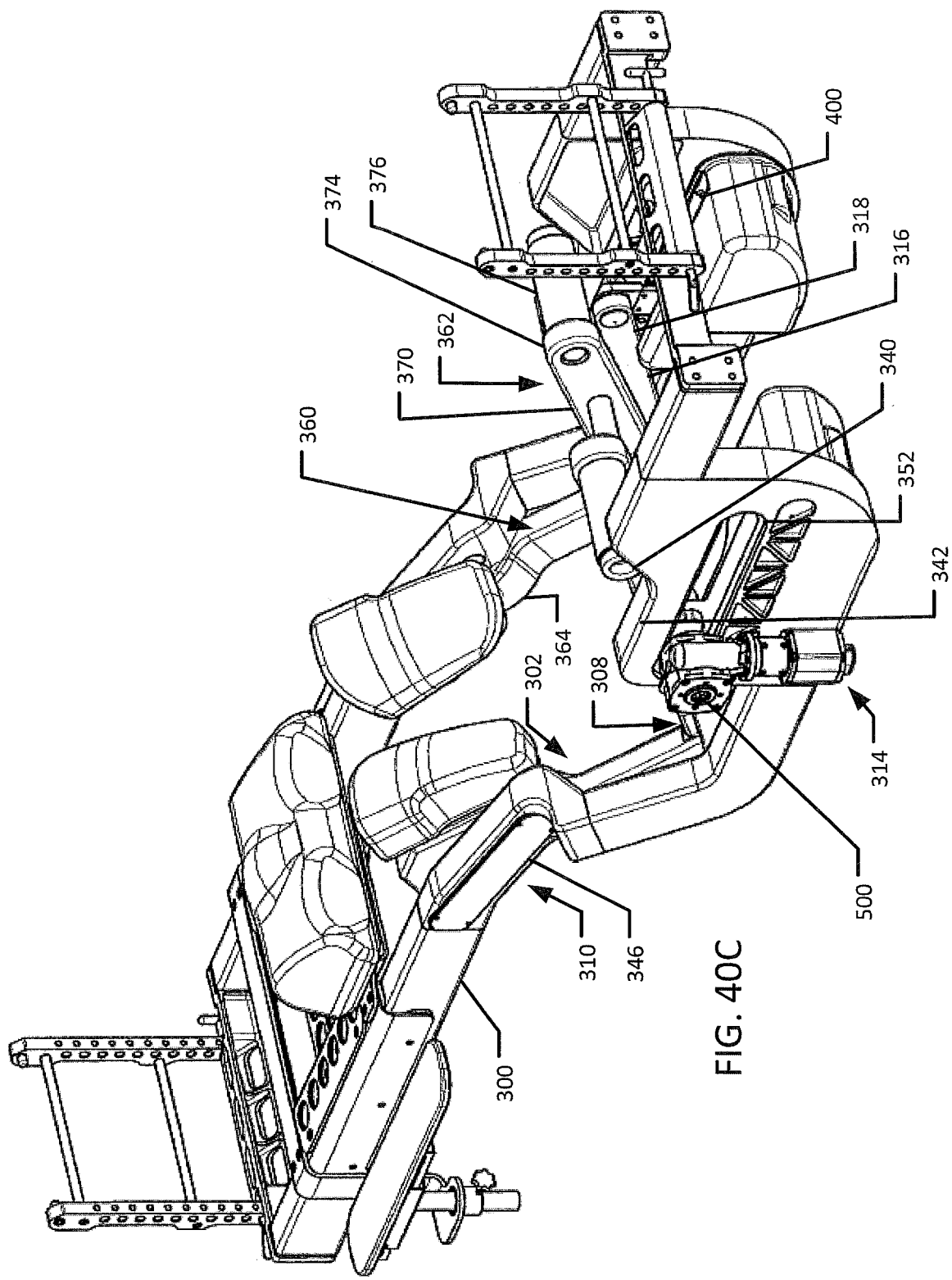
Figure 41A:
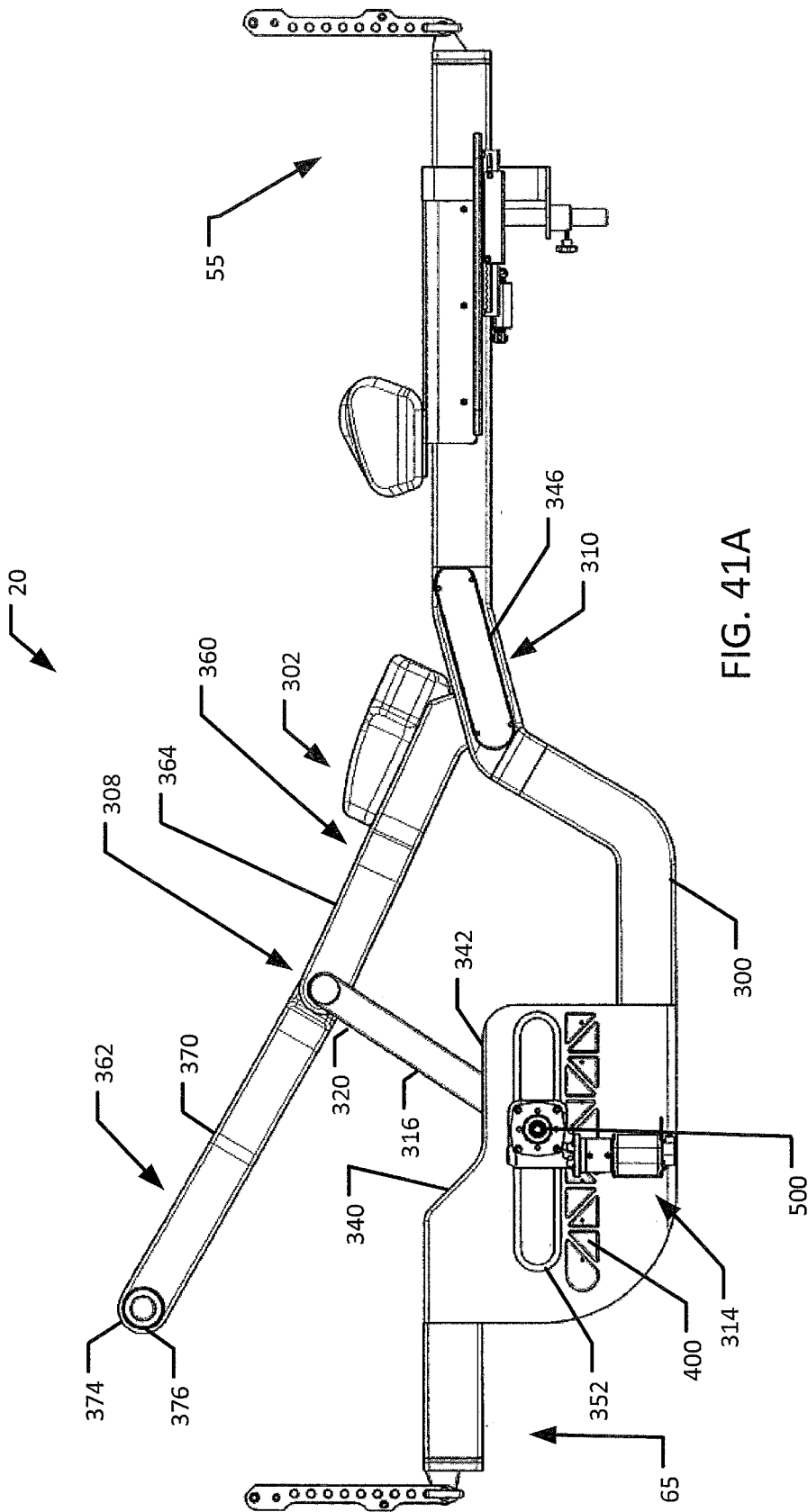
FIGS. 41A-41C are of the same view as FIG. 3, except only depicting the patient support and H-frames, with the inner frame shown in the elevated position, the neutral position and the lower position, respectively
Figure 41B:
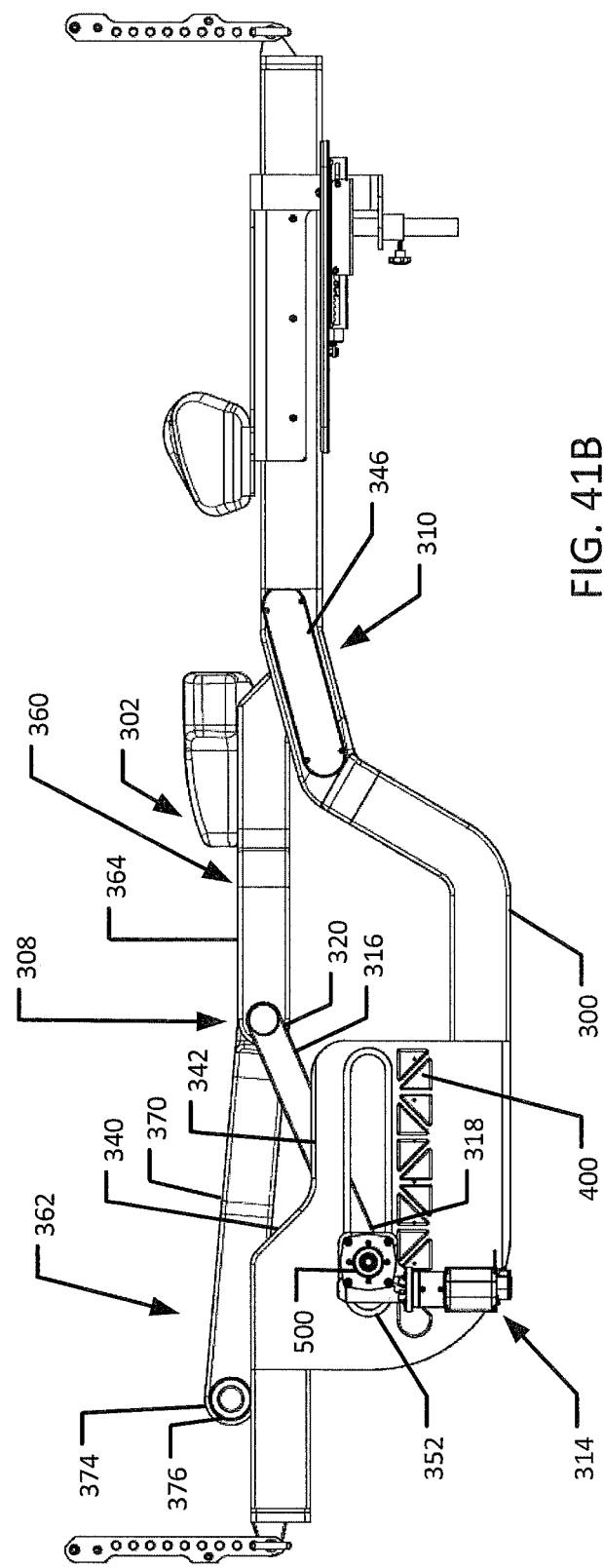
Figure 41C:
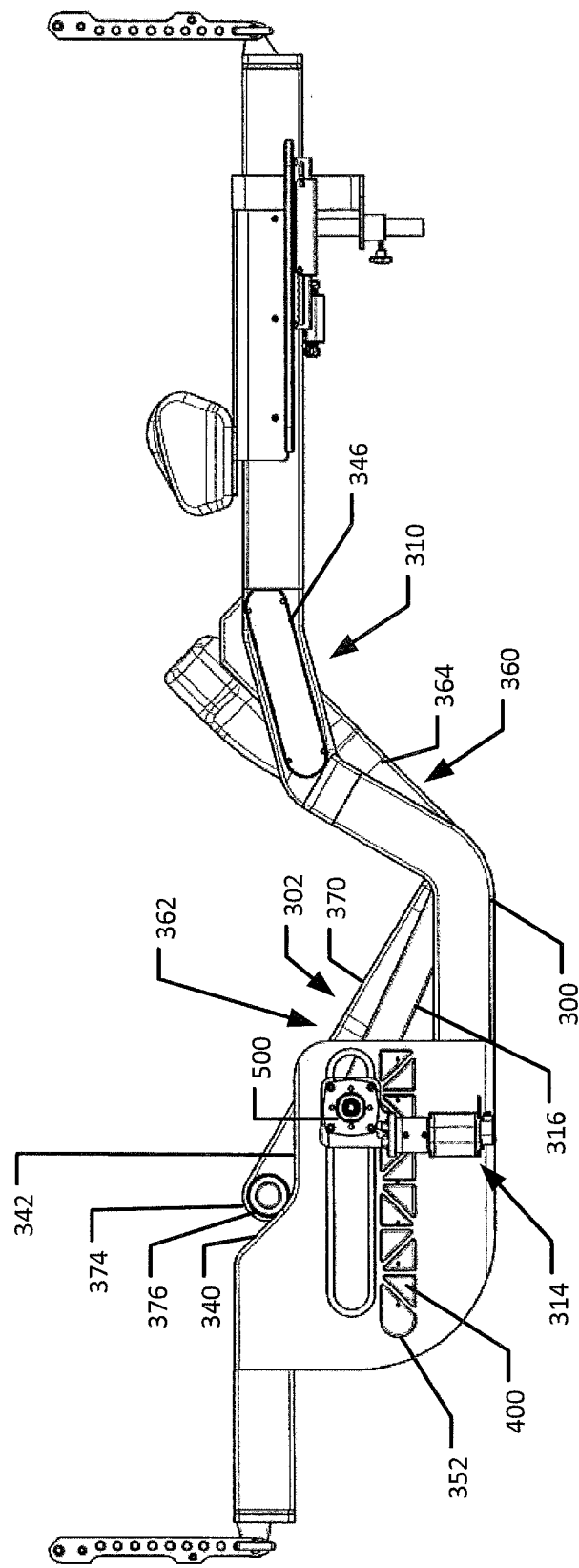

FIG. 35 is an enlarged view of the exploded rotation drive assembly 314 illustrated in FIG. 29. As shown in FIG. 29, the rotation drive assembly 314 includes a drive shaft 500, various bearing rings 510, and a drive motor 512 with its gear box 514. As can be understood from FIGS. 33A-34C, the bearing block 420 couples the drive motor 512 and its gear box 514 to the slider block 402 such that the rotation drive assembly 314 linearly displaces with slider block 402 when the slider block 402 is caused to linearly displace along the linear guide rail 400 of the linear drive assembly 312.

The drive shaft 500 pivotally extends thorough the bearing block 420 to fixedly connect with the lower end 318 of the link arm 316. Thus, when the drive motor 512 via its gear box 514 causes the drive shaft 500 to rotate about is longitudinal axis relative to the bearing block 420, the link arm 316 is caused to pivot about the longitudinal axis of the drive shaft 500 in a plane extending lengthwise along the length of the rigid frame 300 and perpendicular to a right-to-left width of the rigid frame, thereby bringing about displacement and articulation of the respective articulation joint 308 and sliding at the respective slider joint 310.

The linear drive assembly 312 acts between the outer frame 302 and its respective rotation drive assembly 314 to linearly displace the rotation drive assembly 314 relative to the outer frame 300. This linear displacement of the rotation drive assembly 314 and the lower end 318 of the link arm 316 adds to the articulation of the respective articulation joint 308 and sliding at the respective slider joint 310 provided by the respective rotation drive assembly 314.

d. The Displacement of the Inner Frame Assembly

For a discussion of the movement of the components of the drive assembly 304 and the inner frame 302 relative to the outer frame 300, reference is first made to FIGS. 39A, 40A, 41A, 42A and 43A where the inner frame 302 is shown in the elevated position. In the following discussion, the term caudad is used to indicate that something is moving, facing, located or oriented in the direction of the foot end 65 of the patient platform 20. Similarly, the term cephalad is used to indicate that something is moving, facing or oriented in the direction of the head end 55 of the patient platform 20.

As indicated in FIGS. 39A, 40A, 41A, 42A and 43A, among others, the first and second members 364, 370 form a straight line when the free ends 374 reach their respective greatest downward extent relative to the respective articulation joints 308. The slider block 402, bearing block 420 and rotation drive 314 are located approximately at the midpoint of the length of the linear guide rail 400 and the screw drive shaft 404. The lower end of the link arm and the drive axel 500 of the rotation assembly 314 are likewise at the midpoint of the length of the slot 352 in the drive assembly support structure in the recessed region of the outer frame 300. The link arm 316 extends at approximately a 30 degree (plus or minus approximately 15 degrees) angle from vertical from the drive axel 500 of the rotation assembly 314. The slider pin 367 is at the lowest and most caudad end of the slider slot 346 of the slider joint 310. The slider slot 346 can be seen to have an incline relative to horizontal of approximately 30 degrees, plus or minus approximately 15 degrees.

FIGS. 39B, 40B, 41B, 42B and 43B illustrate the inner frame 302 in the neutral position. As indicated in these figures, the first and second members 364, 370 form a straight line when the free ends 374 reach their respective greatest downward extent relative to the respective articulation joints 308. Also, the contact members 376 at the free ends 374 rest on the flat upper surface of the foot end region of the outer frame 300 (see FIGS. 39B, 40B and 41B). The slider block 402, bearing block 420 and rotation drive 314 are located approximately at the most caudad end of the linear guide rail 400 and the screw drive shaft 404. The lower end of the link arm and the drive axel 500 of the rotation assembly 314 are likewise at the most caudad end of the length of the slot 352 in the drive assembly support structure in the recessed region of the outer frame 300. The link arm 316 extends at approximately a 60 degree (plus or minus approximately 15 degrees) angle from vertical from the drive axel 500 of the rotation assembly 314. The slider pin 367 is at slightly caudad of the midpoint of the slider slot 346 of the slider joint 310.

FIGS. 39C, 40C, 41C, 42C and 43C illustrate the inner frame 302 in the lower position. As indicated in these figures, the first and second members 364, 370 form approximately a 90 degree angle (plus or minus 15 degrees) at the articulation joints 308. Also, the contact members 376 at the free ends 374 rest on the transition between the sloped surface 340 and the flat surface 342 of the recessed region of the outer frame 300 (see FIGS. 39C, 40C and 41C). The slider block 402, bearing block 420 and rotation drive 314 are located approximately at the most cephalad end of the linear guide rail 400 and the screw drive shaft 404. The lower end of the link arm and the drive axel 500 of the rotation assembly 314 are likewise at the most cephalad end of the length of the slot 352 in the drive assembly support structure in the recessed region of the outer frame 300. The link arm 316 extends at approximately a 30 degree (plus or minus approximately 15 degrees) angle downward from horizontal from the drive axel 500 of the rotation assembly 314. The slider pin 367 is at the highest and most cephalad end of the slider slot 346 of the slider joint 310.

As can be understood from FIGS. 39A-43C, when drive assembly 304 causes the inner frame 302 to transition from of the elevated position depicted in FIGS. 39A, 40A, 41A, 42A and 43A to the neutral position of the FIGS. 39B, 40B, 41B, 42B and 43B, the drive axels 500 and the link arm lower ends 318 displace linearly caudad from approximately the midpoints of the screw drives 404 to approximately the most caudad points of the screw drives 404. At the same time, the drive axels 500 causes the link arm upper ends 320 to arc cephalad and downward from approximately 30 degrees cephalad of vertical until the link arms 316 are approximately 60 degrees cephalad of vertical. While all of this is occurring, the upper and lower segments 364, 370 of the inner frame 302 remain straight extending across the articulation joints 308, the contact members 376 at the free ends 374 go from being elevated above the outer frame 300 to coming into contact with the caudad region of the outer frame, and the slider pins 367 move cephaladly approximately one third of the total length of the slider slots 346 from the most caudad and lowest ends of the slider slots 346.

As can be understood from FIGS. 39A-43C, when drive assembly 304 causes the inner frame 302 to transition from of the neutral position depicted in FIGS. 39B, 40B, 41B, 42B and 43B to the lower position of the FIGS. 39C, 40C, 41C, 42C and 43C, the drive axels 500 and the link arm lower ends 318 displace linearly cephalad from approximately the most caudad points of the screw drives 404 to approximately the most cephalad points of the screw drives 404. At the same time, the drive axels 500 causes the link arm upper ends 320 to arc cephalad and downward from approximately 60 degrees cephalad of vertical until the link arms 316 are approximately 30 degrees below horizontal. While all of this is occurring, the upper and lower segments 364, 370 of the inner frame 302 transition from being straight extending across the articulation joints 308 to forming approximately a 90 degree angle at the articulation joints 308, the contact members 376 at the free ends 374 go from contacting the caudad region to rolling or sliding along the outer frame 300 and traveling down the inclined portions 340 of the recessed region of the outer frame to eventually come to rest at the transitions between the inclined portions 340 and the horizontal portions 342 of the recessed region of the outer frame 20. This contact between the contact members 376 and the components of the outer frame 300 facilitate deflecting the lower leg region 362 relative to the upper leg region 360 about the joint 308. At the same time, the slider pins 367 move cephaladly to the most cephalad and highest ends of the slider slots 346 from the spots that were approximately one third of the total lengths of the slider slots 346 from the most caudad and lowest ends of the slider slots 346.

To transition from the lowest position, through the neutral position, to the elevated position, the above-described directions and order of movements can simply be reversed.

These above-described transition processes can be automated by software stored on the computer, the software including instructions to the rotation and linear drive assembly motors that mimic the above-described directions and order of movements. Limit switches and various sensors can be provided in the components of the drive assembly and/or on the inner frame that indicate to the computer when any of the three above-described inner frame positions have been achieved, signaling the user of such a state and stopping the drive assembly from trying to further displace the inner frame until signaled by the user via the computer to transition to another inner frame position.

e. The Patient Interaction with the Inner Frame Assembly

For a discussion of the movement of the patient relative to the inner frame when the inner frame is displacing, reference is made to FIGS. 1-4 and FIGS. 36A-38B. As can be understood from these figures, but especially from FIGS. 3 and 38A-38B, when the upper leg support region 360 and lower leg support region 362 work together to flex the patient from neutral, the hip pads 369 angulate or rotate downward and, additionally, slide cephalad. When the upper leg support region 360 and lower leg support region 362 work together to extend the patient from neutral, the hip pads 369 angulate or rotate upward and, additionally, slide caudad. As can be understood from the figures discussed herein, the displacement of the hip pads 369, and the patient 12 resting therein on, is such that the spine of the patient 12 is not compressed or distracted as the patient is transitioned between extension, neutral, or flexion, vice versa or in any other order or sequence.

f. Positioning of the Patient Support Relative to the Base

As noted above, the outer frame 300 of the patient platform 20 is rolled and pitched via the head end pivot/roll assembly 130 and the foot end pivot/roll assembly 140 of the surgical table base 15. The outer frame 300 extends as a rigid frame work that does not change structural configuration and also does not articulate relative to or about itself, while the inner frame 302 displaces relative to the outer frame 300 and also articulates relative to itself.

Articulations of the patient are brought about by the displacement of the inner frame 302 relative to the outer frame 300. However, pitching and rolling of the patient are brought about by pitching or rolling the entire patient platform 20 relative to the based 15. Via the operation of the inner frame relative to the outer frame and the entire patient platform relative to the frame, the patient may be place in a variety of positions while the roll axes of the respective roll assemblies remain coaxial, as discussed above with respect to FIG. 7. Examples of patient positions includes, but are not limited to, prone positioning, supine positioning, lateral decubitis positioning, seated positioning, etc.

With respect to prone positioning, the patient may be placed in neutral, flexion and extension positions. The patient support can have its chest and hip pads moved and or removed as needed for the procedure.

Supine positioning involves providing separate flat-top surfaces on the thigh regions of the inner frame 302 and on the head end region of the outer frame 300, these separate flat-top surfaces being positioned relative to the articulation joint 308 so as to articulate relative to each other. Additional pads or pillows can be positioned on the flat-top surfaces, as needed.

Lateral decubitis positioning flexes the patient with the thigh region of the inner frame 302 dependent in a declining orientation, wherein the foot end of the inner frame is close to the floor.

FIGS. 44-52 illustrate some of these sample positions of the patient platform of the surgical table. Positioning capabilities of the surgical table 10 disclosed herein should not be considered as being limited to those positions illustrated in the accompanying figures or as described herein, but are provided merely as examples. Those of skill in the art will readily understand from the drawings and description the wide range of positioning options provided via the surgical table.

Reference will initially be made to FIGS. 44-46, which are respective isometric head end, isometric foot end, and side views of an embodiment of the surgical table 10 with the patient support 20 positioned with flat-top pads 600 and a pad 602 to position a patient (not shown) in a seated and slightly reclined position. As seen in the figures, the patient support 20 is elevated at the head end 55 relative to the foot end 65 and the inner frame 302 is articulated at the articulation joint 368 such that the joint 368 is at an apex or high point relative to the upper and lower leg members 360, 362. In this orientation, the head end vertical support 100 is extended such that the intermediate segment 152 and the inner segment 154 are extended out from the outer segment 150. Opposite the head end vertical support 100, the foot end vertical support 100, coupled with the foot end 65 of the patient support, is in an un-extended position. The foot end vertical support 100 may, however, be somewhat extended in this position, as long as it is extended vertically less than the head end vertical support 100.

As seen and as discussed in reference to FIGS. 31, 33A, 36A, 37A, 38A, 39A, 40A, 41A, 42A, and 43A, among others, when the patient support 20 is in an extended position, the upper leg member 360 and the lower leg member 362 of the inner frame 302 are generally parallel to each other and angled upward relative to the outer frame 300. The upper and lower leg members 360, 362 remain parallel in this orientation, as opposed to flexing at the joint 368, is because the articulating joint 368 is configured so as to prohibit rotation of the upper and lower leg members 360, 362 past the point of being parallel or one hundred eighty degrees relative to each other. There may, for example, be a pull-pin (not shown) at the location of the articulating joint 368 that prevents the lower leg member 362 from rotating past one hundred eighty degrees relative to the upper leg member 360. The pull-pin may, however, allow rotation of the upper and lower leg members 360, 362 to rotate into flexion, as seen and described in reference to FIGS. 34C, 36B, 37B, 38B, 39C, 40C, 41C, 42C, and 43C, among others. That is, rotation (i.e., passive or active) of the upper and lower leg members 360, 362 of less than one hundred eighty degrees is unrestricted. The pull-pin may function to lock or otherwise not allow rotation past one hundred eighty degrees.

Referring back to FIGS. 44-46, to facilitate the inner frame 302 of the patient support 20 flexing at the articulating joint 368 such that the joint 368 is at an apex (i.e., the upper and lower leg members 360, 362 rotation past or beyond one hundred eighty degrees relative to each other), the pull-pin may be removed or disengaged with the articulating joint 368 such that the joint 368 is able to freely rotate into the seated position. The pull-pin may be re-engaged or reinserted into the articulating joint 368 to lock the joint 368 into a desired position (e.g., at an apex such that the patient support 20 is in the seated position). Other mechanisms are possible to accomplish these functions; the pull-pin is just one possible mechanism. The other mechanisms are contemplated within the present disclosure.

As most clearly seen in FIG. 46, the foot end 65 of the patient support 20 is coupled with the H-frame 206 at a through hole near the low end of the H-frame 206. The head end 55 of the patient support 20, on the other hand, is coupled with the H-frame 206 near the top end of the H-frame 206. Also as seen in FIG. 46, the pitch assemblies 172 are actuated to maintain the roll assemblies 174 in coaxially alignment. That is, the pitch assembly 172 on the foot end vertical support 100 is angled upward and the pitch assembly 172 on the head end vertical support 100 is angled downward relative to each other such that the roll assemblies 174 are actively maintained in coaxially alignment with each other.

Figure 47:
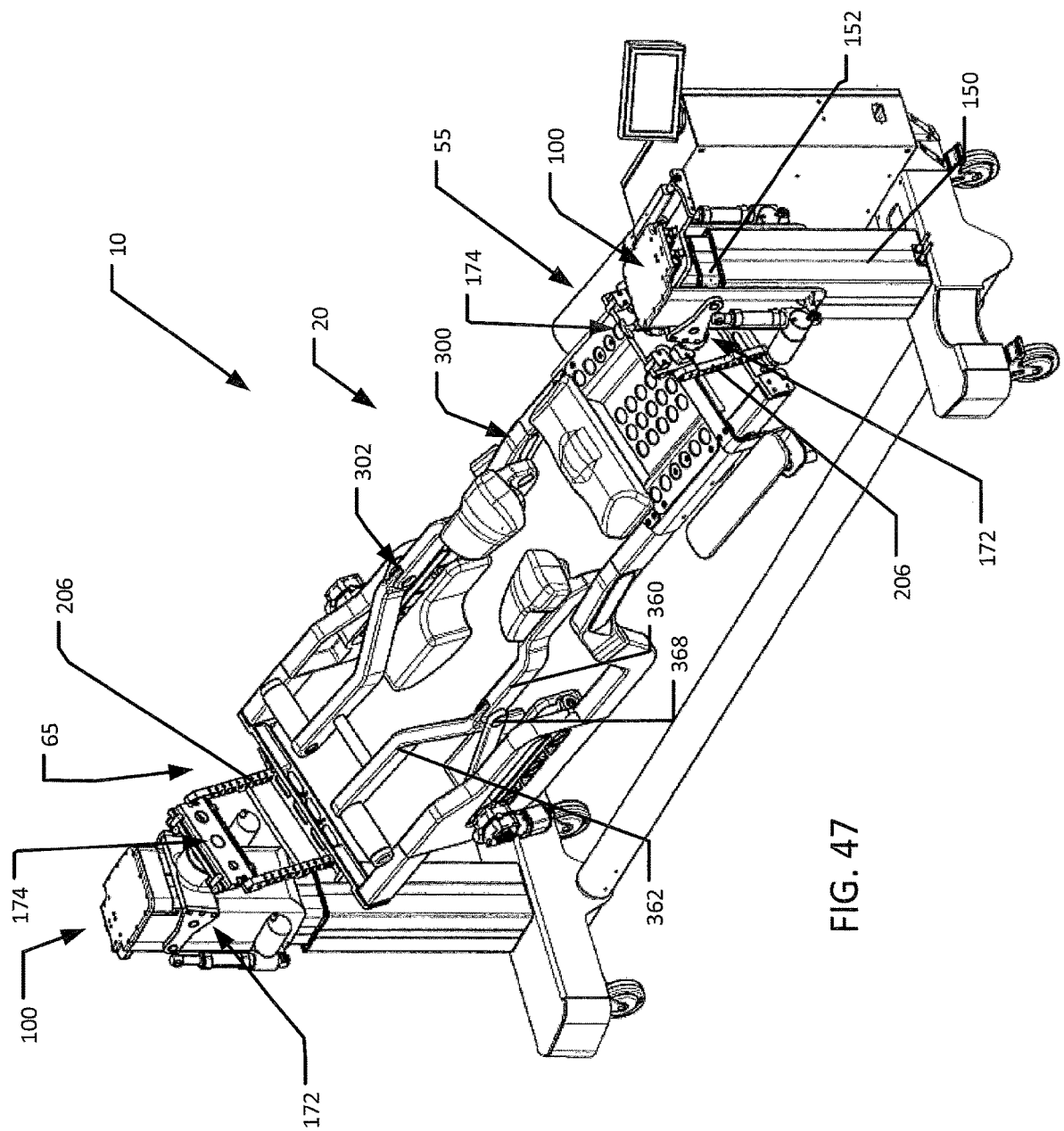
FIG. 47 is an isometric view from a right side and a head end perspective of an embodiment of the surgical table with the patient support in Trendelenburg with a partial roll around a longitudinal axis of the patient support.
Figure 48:
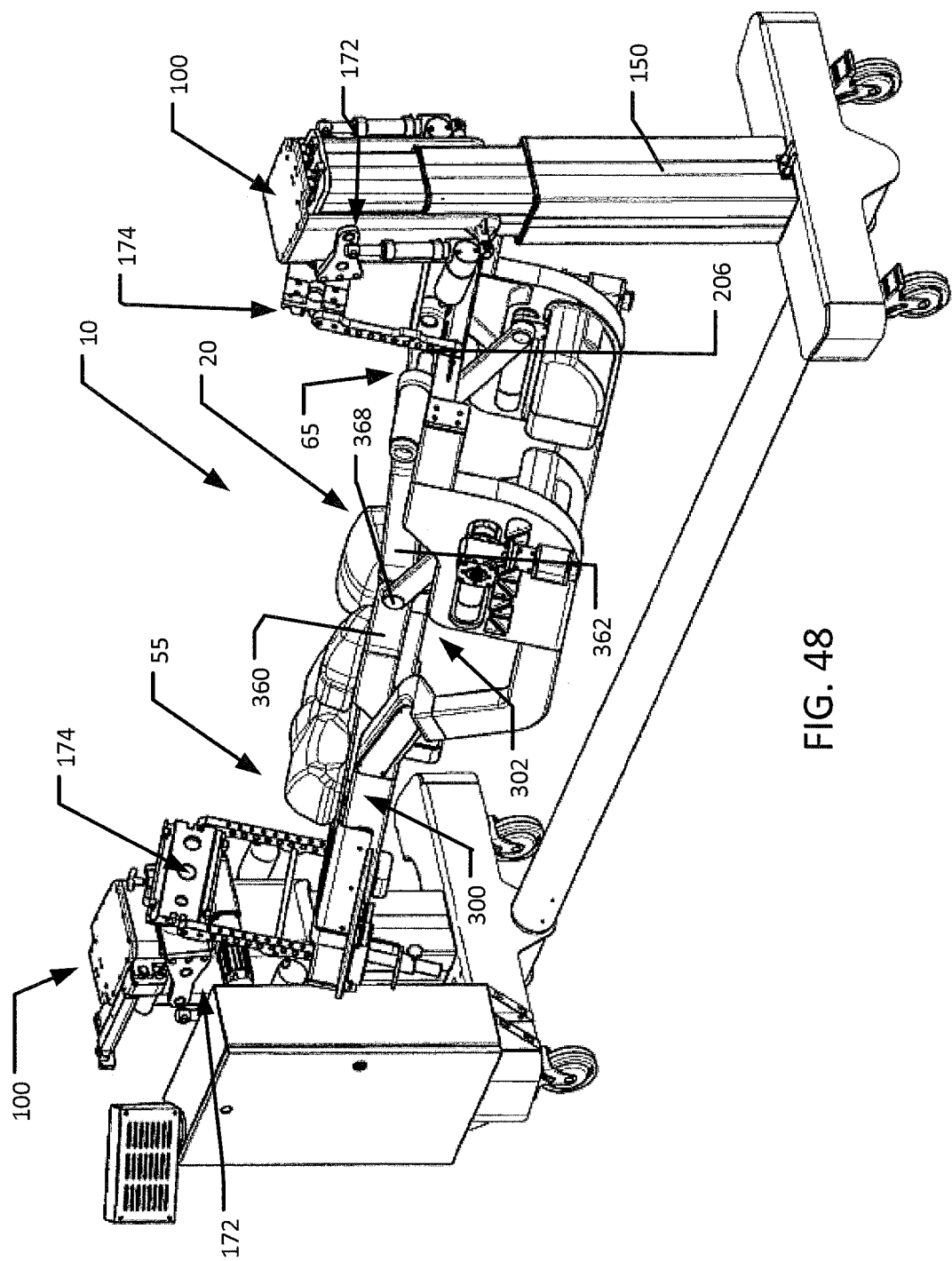
FIG. 48 is an isometric view from a left side and foot end perspective of the surgical table as shown in FIG. 47.
Figure 49:
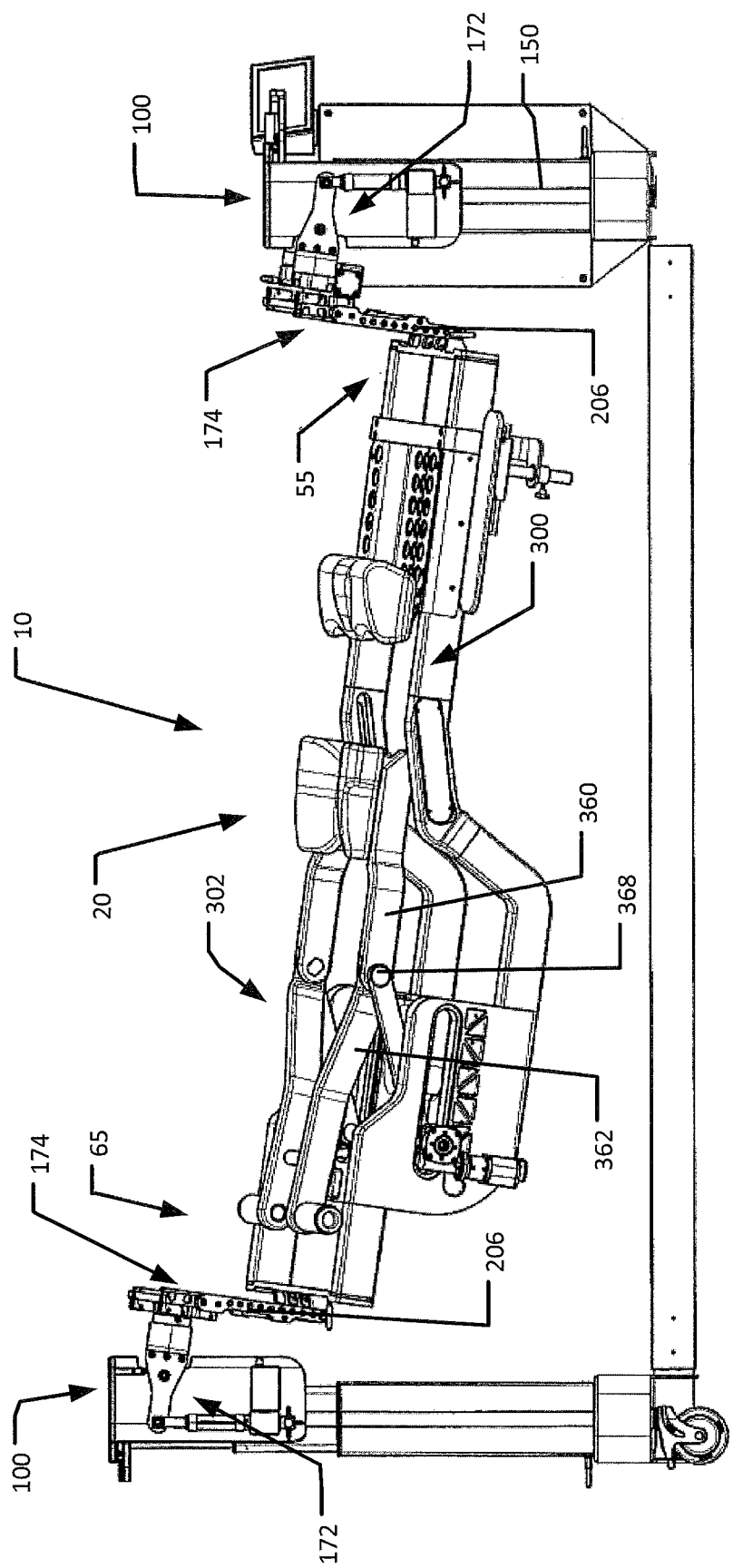
FIG. 49 is a right side view of the surgical table as shown in FIG. 47.

Reference is now made to FIGS. 47-49, which are, respective, head end isometric, foot end isometric, and side views of an embodiment of the surgical table 10 with the patient support 20 in Trendelenburg with a partial roll around a longitudinal axis of the patient support 20. In this position, the head end vertical support 100 is unextended or vertically extended less than the foot end vertical support 100 such that the head end 55 of the patient support 20 is positioned lower than the foot end 65 of the patient support 20. In addition to the head end 55 of the patient support 20 being positioned lower than the foot end 65 of the patient support 20, the patient support 20 is also pivoted, rolled, or rotated about a longitudinal axis of the patient support 20 via the roll assemblies 174.

As seen in the FIG. 49, the ladder attachment assemblies 198 and, in particular, the H-frames 206 are substantially parallel to each other. And, the roll assemblies 174 are in-line such that the axels 196 of the roll assemblies 174 are substantially coaxially aligned. To facilitate the roll assemblies 174 being coaxially aligned, the pitch assembly 172 on the foot end vertical support 100 is angled downward and the pitch assembly 172 on the head end vertical support 100 is angled upward relative to each other.

Figure 50:
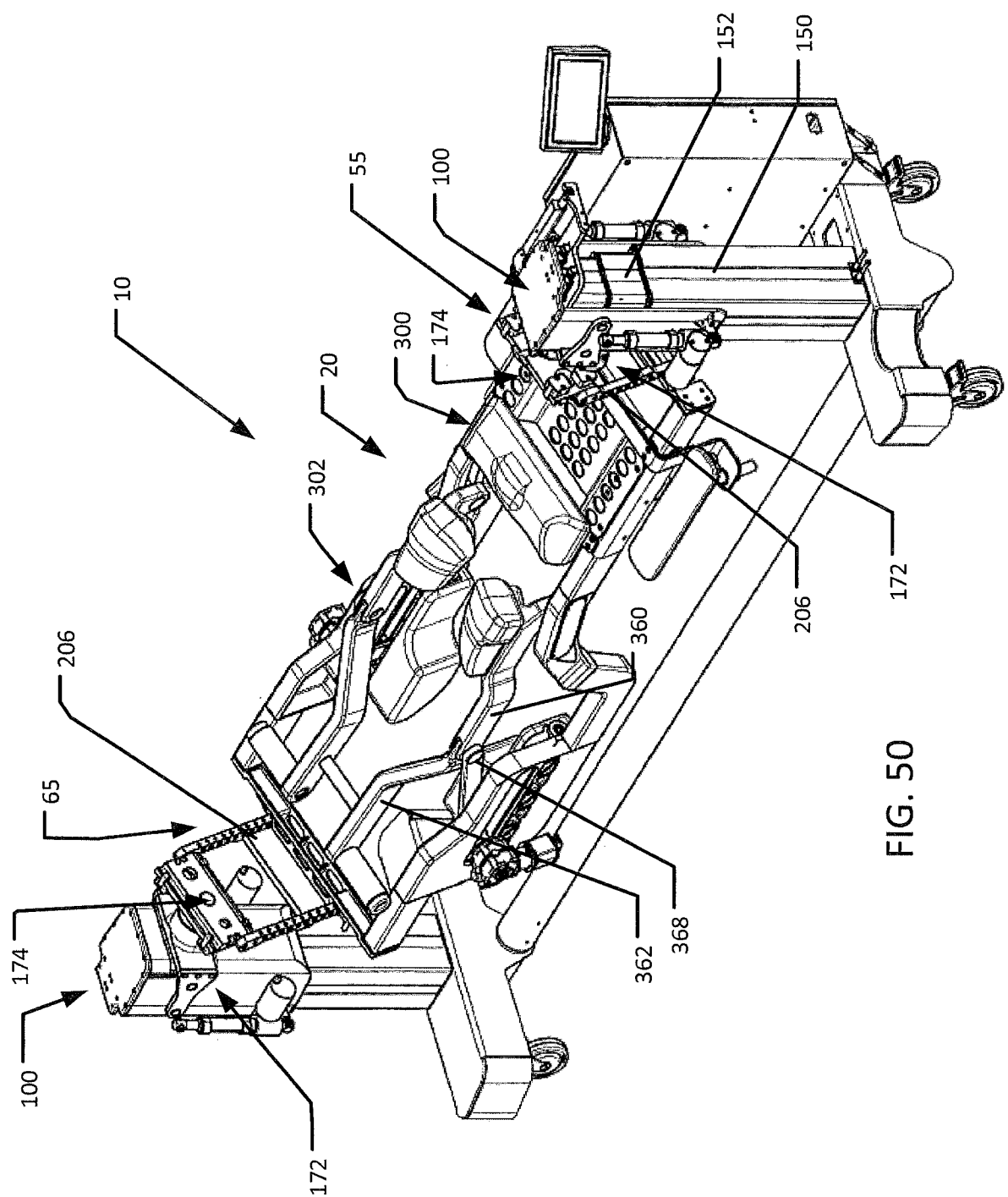
FIG. 50 is an isometric view from a right side and a head end perspective of an embodiment of the surgical table with the patient support in a partial rolled position.
Figure 51:
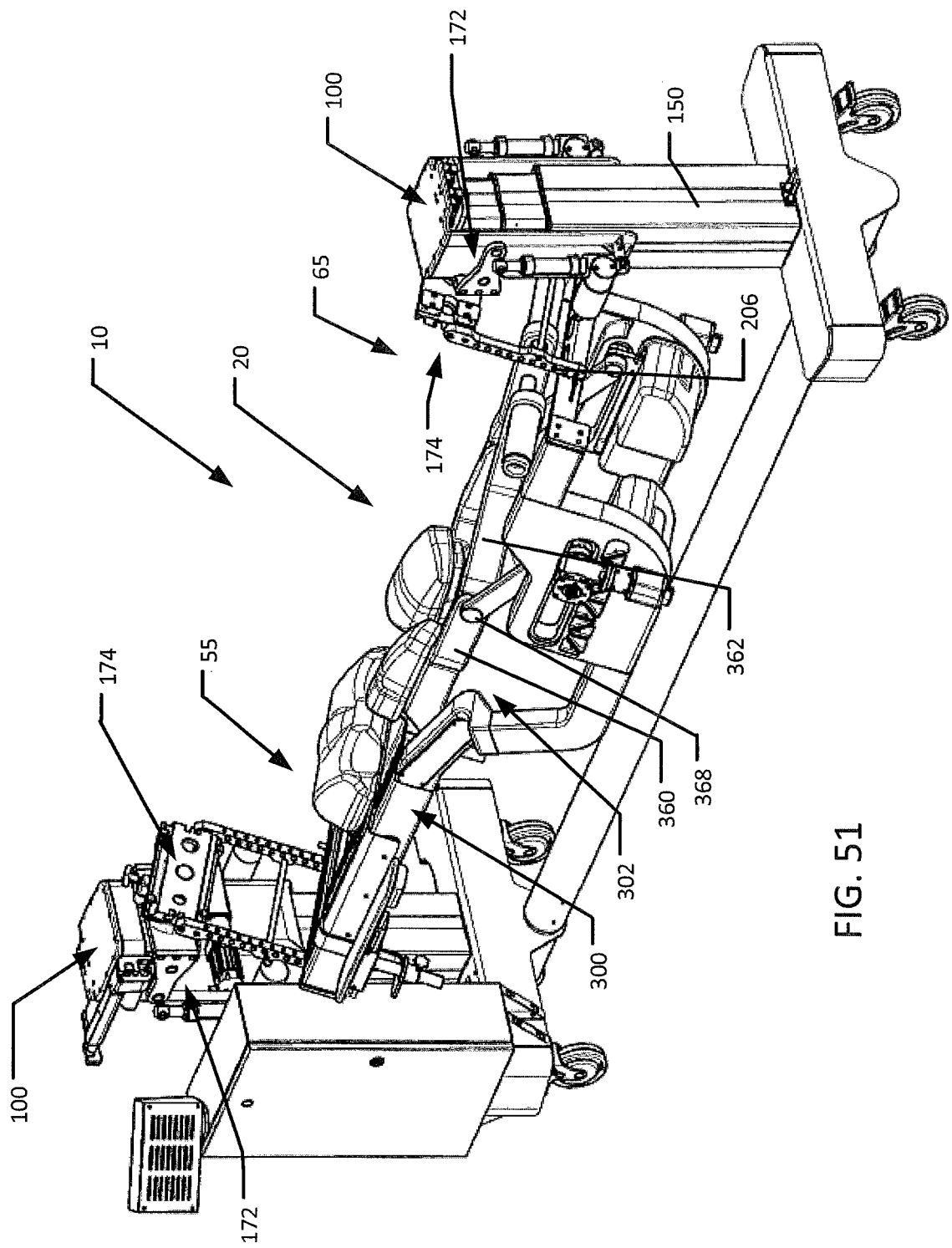
FIG. 51 is a left side view of the surgical table as shown in FIG. 50.
Figure 52:
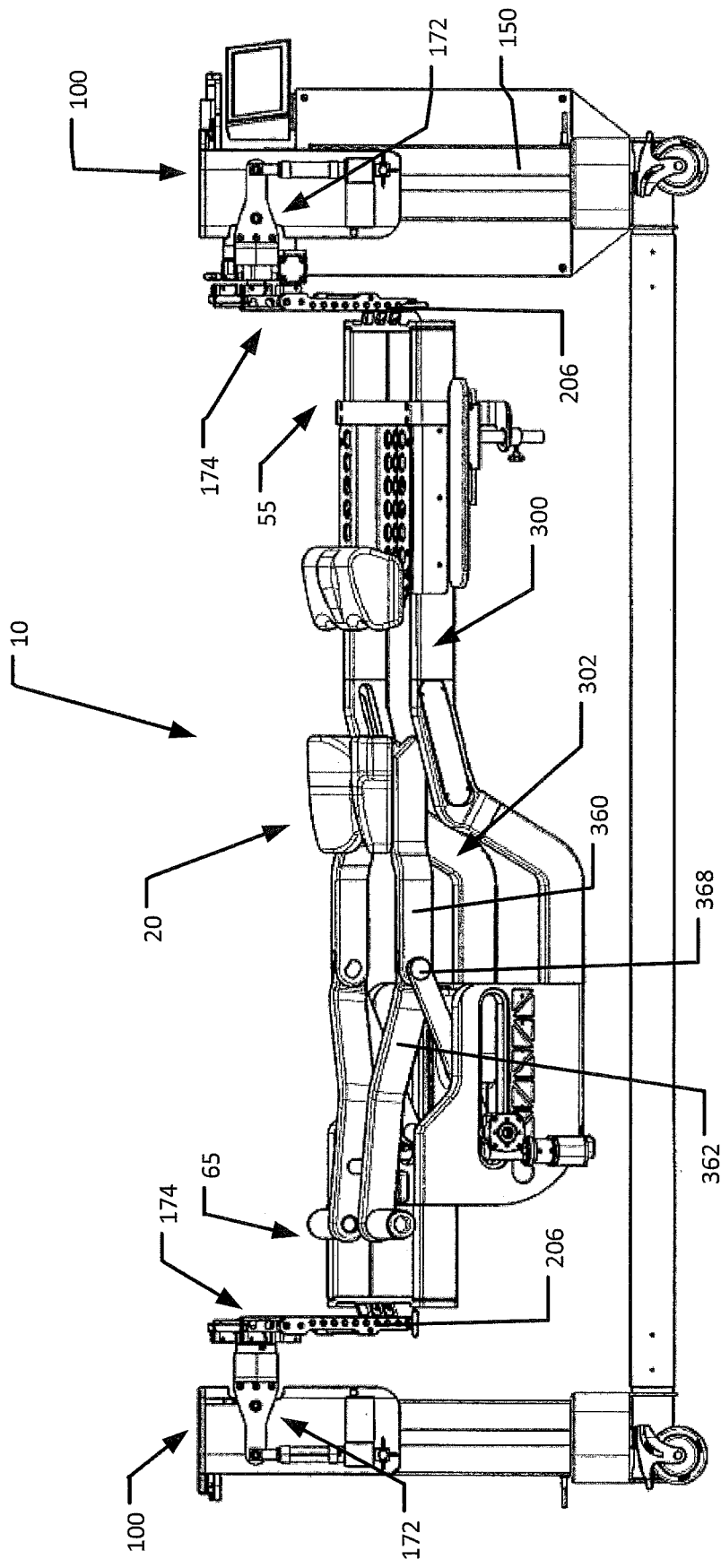
FIG. 52 is right side view of the surgical table as shown in FIG. 50.

Reference is now made to FIGS. 50-52, which are, respective, head end isometric, foot end isometric, and side views of an embodiment of the surgical table 10 with the patient support 20 in a partial roll around a longitudinal axis of the patient support 20. In this orientation, the patient support 20 is generally parallel with the floor and generally perpendicular with the end supports 100. This position is similar to the neutral position, except the roll assemblies 174 are rotated about the longitudinal axis of the patient support 20. As seen in the figures, the H-frame 206 and the ladder attachment assemblies 198 are substantially parallel to each other, despite the patient support 20 being rolled about the longitudinal axis. And, the pitch assemblies 172 are similarly positioned such that the roll assemblies 174 and, in particular, the axels 196 of the roll assemblies 174 are coaxially aligned.

III. Software Operations of Table and Associated Hardware

Figure 53:
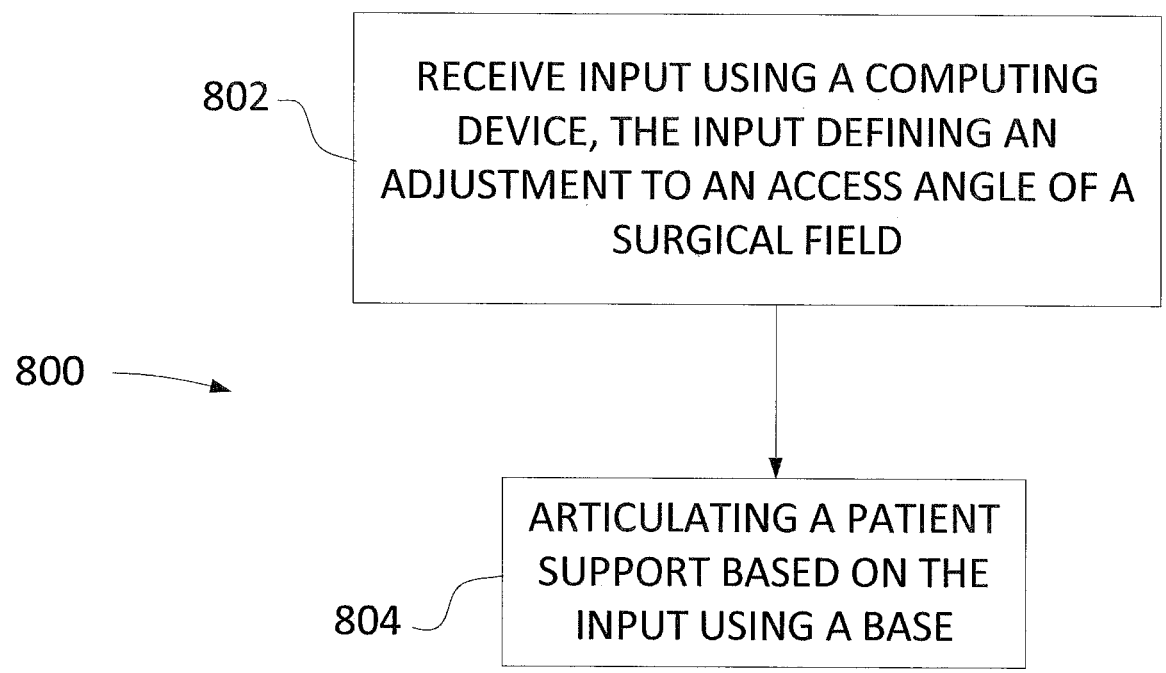
FIG. 53 illustrates a computer operation.

FIG. 53 illustrates example operations 800 for articulating a patient support 20 in a surgical table 10, as shown in FIG. 1. In one implementation, an operation 802 receives input from a user, such as medical personnel, using a computing device 115, which may be a user device generating a graphical user interface on a screen 145 as can be understood from FIG. 5 and others discussed above. The input defines an adjustment to an access angle of a surgical field. An operation 804 articulates the patient support 20 based on the input using the inner frame 302 on the outer frame 300, the inner frame 302 displaced via the drive assembly 304 as discussed above. The operation 804 may also displace the patient support 20 by displacing the rigid frame 300 of the patient support 20 relative to the base 15 of a surgical table 10, as seen in FIG. 1. The motors of the drive and displacement assemblies of the patient support 20 and the base 15 of the table 10 may be servo-motors with software synchronization and sensors that all run together and independently as directed to maintain the positioning of the surgical site relative to the floor during the articulation and displacement of the patient via the surgical table 10 of FIG. 1.

The articulation displacement may include various motions, as detailed herein, such as: moving the patient platform outer frame 300 about one or more pitch axes to and from a neutral position, an extension position, or a flexion position; moving the patient platform outer frame 300 about one or more roll or vertical axes; translating the patient platform outer frame 300 cephalad, caudad, patient left or patient right; or causing the patient platform inner frame 302 to displace relative to the patient platform outer frame 300 to articulate the patient platform or patient between extension, neutral and flexion positions. During these articulations and displacements, the operations 800 may be such that the surgical field (e.g., the lumbar spine) is kept stable in relation to the floor such that the surgical field does not move up or down or cephalad or caudad in relation to the floor during the articulations or displacements unless the operator purposely intends the surgical field to move up or down or cephalad or caudad in relation to the floor during the articulations or displacements. The mechanical arrangements of the inner frame 302 and outer frame 300, the movements of the inner frame 302 relative to outer frame 300, and the coordination of these movements via the operations 800 are such that the articulations through the extension, neutral, and flexion positions, and vice versa, do not cause compression of distraction of the spine of the patient 12.

Figure 54:
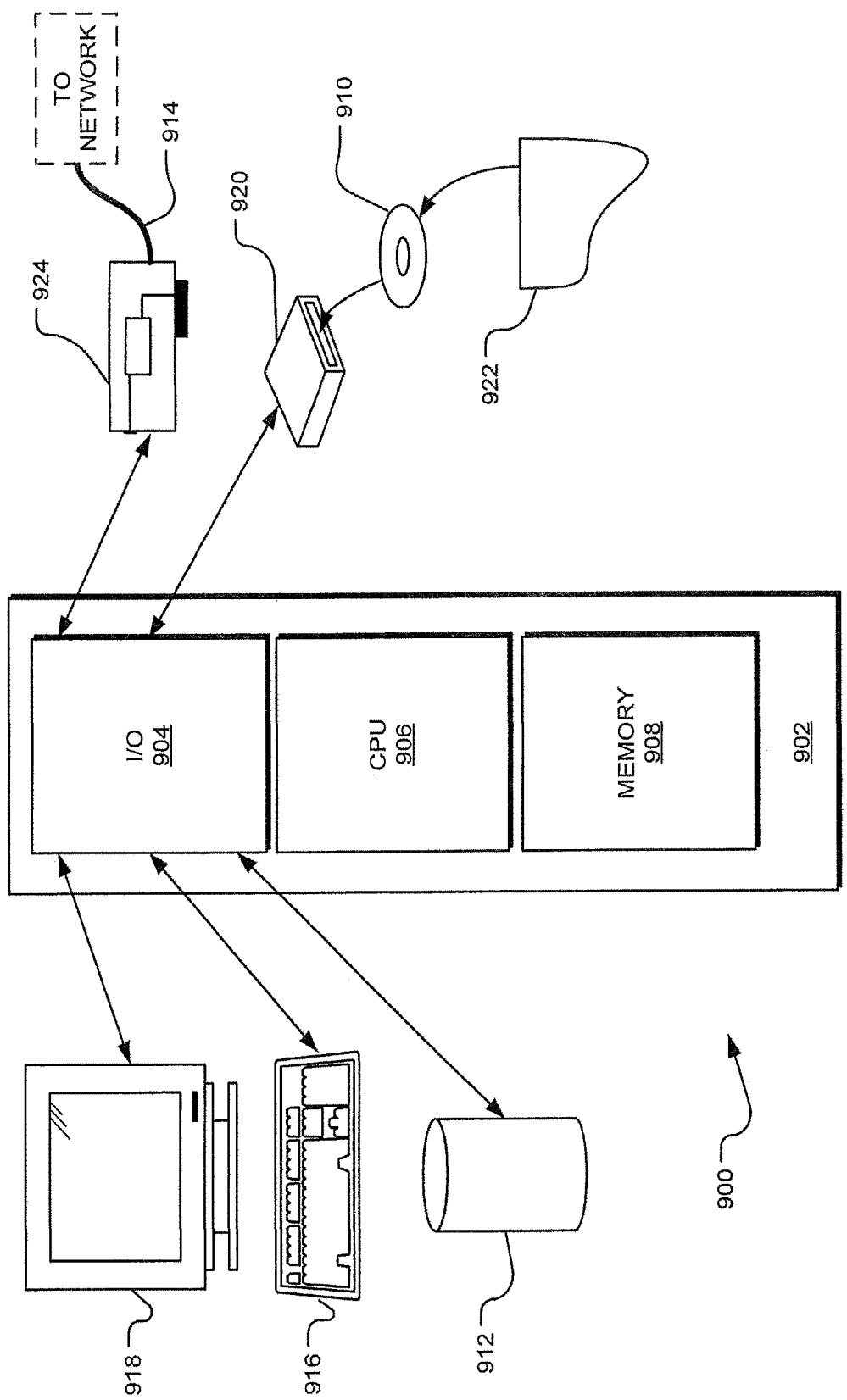
FIG. 54 illustrates a diagrammatic depiction of a computer system for implementing the computer operation of FIG. 53.

FIG. 54 is a diagrammatic depiction of an example computing system 900 wherein the computing system 900 may have one or more computing units that may implement various systems and methods discussed herein. Depending on the embodiment, the computing system 900 may be applicable to the user device 115 of FIG. 5 and others, a server in communication with a network, and/or other computing devices. It will be appreciated that specific implementations of these devices may be of differing possible specific computing architectures not all of which are specifically discussed herein but will be understood by those of ordinary skill in the art.

The computer system 900 may be a general computing system is capable of executing a computer program product to perform a computer process. Data and program files may be input to the computer system 900, which reads the files and executes the programs therein.

Some of the elements of a general purpose computer system 900 are shown in FIG. 54 wherein a processor 902 is shown having an input/output (I/O) section 904, a Central Processing Unit (CPU) 906, and a memory section 908. There may be one or more processors 902, such that the processor 902 of the computer system 900 comprises a single central-processing unit 906, or a plurality of processing units, commonly referred to as a parallel processing environment. The computer system 900 may be a conventional computer, a distributed computer, or any other type of computer, such as one or more external computers made available via a cloud computing architecture. The presently described technology is optionally implemented in software devices loaded in memory 908, stored on a configured DVD/CD-ROM 910 or storage unit 912, and/or communicated via a wired or wireless network link 914, thereby transforming the computer system 900 in FIG. 54 to a special purpose machine for implementing the described operations.

The I/O section 904 is connected to one or more user-interface devices (e.g., a keyboard 916 and a display unit 918), a disc storage unit 912, and a disc drive unit 920. In the case of a tablet, a smart phone device, or similar computing device, there may not be a physical keyboard but rather a touch screen with a computer generated touch screen keyboard. Generally, the disc drive unit 920 is a DVD/CD-ROM drive unit capable of reading the DVD/CD-ROM medium 910, which typically contains programs and data 922. Computer program products containing mechanisms to effectuate the systems and methods in accordance with the presently described technology may reside in the memory section 904, on a disc storage unit 912, on the DVD/CD-ROM medium 910 of the computer system 900, or on external storage devices made available via a cloud computing architecture with such computer program products, including one or more database management products, web server products, application server products, and/or other additional software components. Alternatively, a disc drive unit 920 may be replaced or supplemented by an optical drive unit, a flash drive unit, magnetic drive unit, or other storage medium drive unit. Similarly, the disc drive unit 920 may be replaced or supplemented with random access memory (RAM), magnetic memory, optical memory, and/or various other possible forms of semiconductor based memories.

The network adapter 924 is capable of connecting the computer system 900 to a network via the network link 914, through which the computer system can receive instructions and data. Examples of such systems include personal computers, Intel or PowerPC-based computing systems, AMD-based computing systems and other systems running a Windows-based, a UNIX-based, or other operating system. It should be understood that computing systems may also embody devices such as terminals, workstations, personal computers, mobile phones, tablets or slates, multimedia consoles, gaming consoles, set top boxes, etc.

When used in a LAN-networking environment, the computer system 900 is connected (by wired connection or wirelessly) to a local network through the network interface or adapter 924, which is one type of communications device. When used in a WAN-networking environment, the computer system 900 typically includes a modem, a network adapter, or any other type of communications device for establishing communications over the wide area network. In a networked environment, program modules depicted relative to the computer system 900 or portions thereof, may be stored in a remote memory storage device. It is appreciated that the network connections shown are examples of communications devices for and other means of establishing a communications link between the computers may be used.

In an example implementation, table articulation data, imaging data, patient data, a plurality of internal and external databases, source databases, and/or cached data on servers are stored as the memory 908 or other storage systems, such as the disk storage unit 912 or the DVD/CD-ROM medium 910, and/or other external storage devices made available and accessible via a network architecture. Table articulation software, imaging software, and other modules and services may be embodied by instructions stored on such storage systems and executed by the processor 902.

Some or all of the operations described herein may be performed by the processor 902. Further, local computing systems, remote data sources and/or services, and other associated logic represent firmware, hardware, and/or software configured to control operations of the table 10 of FIG. 1, the user device 115 of FIG. 5, and/or other computing units or components in communication with the table 10 and/or the user device 115. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 902 and a user may interact with a Graphical User Interface (GUI) using one or more user-interface devices (e.g., the keyboard 916, the display unit 918, and the user device 115). The system set forth in FIG. 54 is but one possible example of a computer system that may employ or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic instructions.

The description above includes example systems, methods, techniques, instruction sequences, and/or computer program products that embody techniques of the present disclosure. However, it is understood that the described disclosure may be practiced without these specific details.

Although various representative implementations have been described above with a certain degree of particularity, those skilled in the art could make numerous alterations to the disclosed embodiments without departing from the spirit or scope of the inventive subject matter set forth in the specification. All directional references (e.g., distal, proximal, front, back, side, top, bottom, fore, aft, right, left, etc.) are only used for identification purposes to aid the reader's understanding of the implementations, and do not create limitations, particularly as to the position, orientation, or use of the invention unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A surgical table for supporting and positioning a patient above a floor, the surgical table comprising:
    a base supported on the floor and comprising a first end support with a first elevation above the floor and a second end support opposite the first end support with a second elevation above the floor;
    a patient support comprising an elongated rigid structure with first and second outer ends, the first outer end coupled to the first end support via a releasable first pivoting connection, the second outer end operably coupled to the second end support via a releasable second pivoting connection, the elongated rigid structure having a first portion with a first flat surface to support the patient, the first flat surface having a first width, the elongated rigid structure pivotally coupled to a second portion that articulates relative to the first flat surface, the second portion having a second flat surface to support the patient, the second flat surface of the second portion having a second width equal to the first width, wherein one of the first pivoting connection or the second pivoting connection is configured to move away from the first end support or the second end support to which it is respectively coupled when the first and second end supports change elevation relative to each other; and
    a slider joint comprising a slider pin, the slider pin being configured to pivot and translate when the second portion articulates relative to the elongated rigid structure.

2. The surgical table of claim 1, wherein the slider joint further comprises a slot configured to receive and guide the slider pin as the slider pin pivots and translates.

3. The surgical table of claim 2, wherein the slot is defined in elongated rigid structure and the slider pin is coupled to the second portion.

4. The surgical table of claim 1, wherein the second portion comprises an upper leg member and a lower leg member coupled together at an articulating joint, the upper and lower leg members being articulable relative to each other at the articulating joint.

5. The surgical table of claim 4, further comprising a drive assembly configured to: displace the second portion relative to the elongated rigid structure about the slider joint, and articulate the upper leg member relative to the lower leg member about the articulating joint.

6. The surgical table of claim 5, wherein the drive assembly comprises at least one motor coupled to a link arm coupled to the second portion, wherein the link arm is configured to transfer forces from the motor to the second portion to bring about displacement of the second portion relative to the rigid structure and to bring about articulation of the upper leg member relative to the lower leg member about the articulating joint.

7. The surgical table of claim 6, wherein the at least one motor comprises a first motor and a second motor, the first motor coupled to the link arm and configured to rotate the link arm, the second motor operably coupled with the first motor and configured to translate the first motor along a linear path.

8. The surgical table of claim 1, further comprising position and limit-stop sensors for the first and second end supports.

9. The surgical table of claim 8, wherein the base is controlled by software driving servomotors for a plurality of mechanical arrangements of the patient support structure, the servomotors being synchronized and linked with the position and limit-stop sensors.

10. The surgical table of claim 1, wherein the first flat surface of the first portion of the elongated rigid structure is a patient-facing surface of first flat-top pads, and the second flat surface of the second portion is a patient-facing surface of second flat-top pads.

11. A surgical table for supporting and positioning a patient above a floor, the surgical table comprising:
   a base supported on the floor and comprising a first end support and a second end support opposite the first end support;
   a patient support comprising a longitudinal axis, an outer frame, an inner frame moveably coupled with the outer frame at a slider joint having an axis of rotation that is transverse to the longitudinal axis, and a drive assembly, the outer frame comprising a first end operably coupled with the first end support and a second end operably coupled with the second end support, the inner frame comprising an upper leg member coupled with a lower leg member at an articulating joint, the drive assembly comprising at least one motor configured to displace the inner frame relative to the outer frame and articulate the upper leg member relative to the lower leg member.

12. The surgical table of claim 11, wherein the drive assembly further comprises a link arm operably coupled between the at least one motor and the inner frame member.

13. The surgical table of claim 12, wherein movement of the link arm causes the inner frame to displace relative to the outer frame and the upper leg member to articulate relative to the lower leg member.

14. The surgical table of claim 12, wherein the at least one motor comprises a first motor and a second motor, the first motor coupled to the link arm and configured to rotate the link arm, the second motor operably coupled to the first motor and configured to translate the first motor along a linear path.

15. The surgical table of claim 11, wherein, when the inner frame articulates relative to the outer frame, the axis of rotation of the slider joint being configured to displace between the first end and the second end of the outer frame.

16. The surgical table of claim 11, wherein the slider joint comprises a pin configured to pivot and translate between the first end and the second end of the outer frame when the inner frame articulates relative to the outer frame.

17. The surgical table of claim 16, wherein the slider joint further comprises a slot configured to receive and guide the pin as the pin pivots and translates.

18. The surgical table of claim 17, wherein the slot is defined within the outer frame and the inner frame comprises the pin.

19. The surgical table of claim 11, wherein the drive assembly is coupled to the outer frame in between the first and second ends of the outer frame.

20. The surgical table of claim 11, wherein the lower leg member is guided by a portion of the outer frame when the upper and lower leg members articulate relative to each other about the articulating joint.

21. The surgical table of claim 20, wherein the portion of the outer frame is a multi-tiered surface near the second end of the outer frame.

22. A surgical table for supporting and positioning a patient above a floor, the surgical table comprising:
   a base supported on the floor and comprising a first end support with a first elevation above the floor and a second end support opposite the first end support with a second elevation above the floor;
   a patient support comprising an elongated rigid structure with first and second outer ends, the first outer end coupled to the first end support via a releasable first pivoting connection, the second outer end operably coupled to the second end support via a releasable second pivoting connection, the elongated rigid structure having a first portion with a first flat surface to support the patient, the first flat surface having a first width, the elongated rigid structure pivotally coupled to a second portion that articulates relative to the first flat surface, the second portion having a second flat surface to support the patient, the second flat surface of the second portion having a second width equal to the first width, wherein one of the first pivoting connection or the second pivoting connection is configured to move away from the first end support or the second end support to which it is respectively coupled when the first and second end supports change elevation relative to each other,
   wherein the second portion comprises an upper leg member and a lower leg member coupled together at an articulating joint, the upper and lower leg members being articulable relative to each other at the articulating joint,
   wherein the surgical table further comprises a drive assembly configured to displace the second portion relative to the elongated rigid structure about a slider joint and articulate the upper leg member relative to the lower leg member about the articulating joint.

23. The surgical table of claim 22, wherein the drive assembly comprises at least one motor coupled to a link arm coupled to the second portion, wherein the link arm is configured to transfer forces from the motor to the second portion to bring about displacement of the second portion relative to the rigid structure and to bring about articulation of the upper leg member relative to the lower leg member about the articulating joint.

* * * * *